United States Patent
Sauvageau et al.

(10) Patent No.: US 9,757,378 B2
(45) Date of Patent: Sep. 12, 2017

(54) METHODS TO MODULATE ACUTE MYELOID LEUKEMIA STEM/PROGENITOR CELL EXPANSION AND/OR DIFFERENTIATION

(71) Applicants: UNIVERSITE DE MONTREAL, Montreal (CA); RSEM LIMITED PARTNERSHIP, Montreal (CA)

(72) Inventors: Guy Sauvageau, Montreal (CA); Josee Hebert, Ville Mont-Royal (CA); Caroline Pabst, Montreal (CA)

(73) Assignees: UNIVERSITE DE MONTREAL, Montréal (CA); RSEM, LIMITED PARTNERSHIP, Montréal (CA)

( * ) Notice: Subject to any disclaimer, the term of this patent is extended or adjusted under 35 U.S.C. 154(b) by 0 days.

(21) Appl. No.: 14/245,062

(22) Filed: Apr. 4, 2014

(65) Prior Publication Data
US 2014/0343051 A1  Nov. 20, 2014

Related U.S. Application Data

(60) Provisional application No. 61/824,734, filed on May 17, 2013.

(51) Int. Cl.
*A61K 31/519* (2006.01)
*A61K 45/06* (2006.01)
(Continued)

(52) U.S. Cl.
CPC .......... *A61K 31/519* (2013.01); *A61K 31/522* (2013.01); *A61K 31/5377* (2013.01); *A61K 45/06* (2013.01); *G01N 33/5073* (2013.01)

(58) Field of Classification Search
CPC .. A61K 31/519; A61K 45/06; A61K 31/5377; A61K 31/522
See application file for complete search history.

(56) References Cited

U.S. PATENT DOCUMENTS

| | | | | |
|---|---|---|---|---|
| 2006/0252073 A1* | 11/2006 | Yilmaz | ............ | G01N 33/5011 435/6.11 |
| 2010/0183564 A1* | 7/2010 | Boitano | ............ | C07D 473/34 424/93.7 |

FOREIGN PATENT DOCUMENTS

| | | | |
|---|---|---|---|
| EP | WO2004/058764 | * | 7/2004 |
| GB | WO 2009/004329 | * | 1/2009 |
| WO | WO2013110198 | | 8/2013 |

OTHER PUBLICATIONS

Schuringa et al (Leukemia, Methods in Molecular Biology, vol. 538 (2009)).*

(Continued)

*Primary Examiner* — Savitha Rao
*Assistant Examiner* — Angela Brown-Pettigrew
(74) *Attorney, Agent, or Firm* — Norton Rose Fulbright Canada LLP

(57) ABSTRACT

Novel methods for modulating acute myeloid leukemia stem/progenitor cell expansion and/or differentiation are disclosed. These methods are based on the use of aryl hydrocarbon receptor (AhR) modulators and/or compounds of formula I or II (Continued)

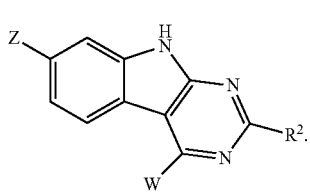

Screening assays to identify compounds that may be useful for inhibiting and/or eliminating AML initiating cells using AhR modulators and/or the compounds of formula I or II are also disclosed. The use of pharmaceutically acceptable agonists of the AhR for preventing or inhibiting minimal residual disease (MRD) in an AML patient is also disclosed.

10 Claims, 30 Drawing Sheets

(51) Int. Cl.
 *A61K 31/5377* (2006.01)
 *G01N 33/50* (2006.01)
 *A61K 31/522* (2006.01)

(56) References Cited

OTHER PUBLICATIONS

Bunaciu et al (Cancer Res. Mar. 15, 2011; 71(6): 2371-2380).*
Wolff, Manfred E., Burger's Medicinal Chemistry and Drug Discovery, Fifth Ed., vol. 1: Principles and Practice, John Wiley & Sons, 1995, 975.*
Banker, Gilbert S. et al., Modem Pharmaceutics, Marcel Dekker, New York, 1996.*
Carrassa et al (Cell. Mol. Life Sci. (2010) 67:1713-1722).*
Barabe et al., Modeling the initiation and progression of human acute leukemia in mice. Science 316, 600-604 (2007).
Bhakta et al., Regulation of cytochrome P4501A1 expression by hyperoxia in human lung cell lines: Implications for hyperoxic lung injury. Toxicology and applied pharmacology 233, 169-178 (2008).
Boitano et al., Aryl hydrocarbon receptor antagonists promote the expansion of human hematopoietic stem cells. Science 329, 1345-1348 (2010).
Bone et al., A novel chemically directed route for the generation of definitive endoderm from human embryonic stem cells based on inhibition of GSK-3. Journal of cell science 124, 1992-2000 (2011).
Borowiak et al., Small molecules efficiently direct endodermal differentiation of mouse and human embryonic stem cells. Cell stem cell 4, 348-358 (2009).
Bouchez et al., Small-molecule regulators of human stem cell self-renewal. Chembiochem : a European journal of chemical biology 12, 854-857 (2011).
Burnett et al., Therapeutic advances in acute myeloid leukemia. Journal of clinical oncology : official journal of the American Society of Clinical Oncology 29, 487-494 (2011).
Casado et al., Aryl hydrocarbon receptor activation in hematopoietic stem/progenitor cells alters cell function and pathway-specific gene modulation reflecting changes in cellular trafficking and migration. Molecular Pharmacology, vol. 80, No. 4 pp. 673-682 (2011).
Choi et al., Design of small molecules that target metal-Aβ species and regulate metal-induced Aβ aggregation and neurotoxicity. Proceedings of the National Academy of Sciences of the United States of America 107, 21990-21995 (2010).
Csaszar et al., Rapid expansion of human hematopoietic stem cells by automated control of inhibitory feedback signaling. Cell stem cell 10, 218-229 (2012).

Denison et al., Activation of the aryl hydrocarbon receptor by structurally diverse exogenous and endogenous chemicals. Annual review of pharmacology and toxicology 43, 309-334 (2003).
Denison et al., Exactly the same but different: promiscuity and diversity in the molecular mechanisms of action of the aryl hydrocarbon (dioxin) receptor. Toxicological sciences : an official journal of the Society of Toxicology 124, 1-22 (2011).
Dick et al. Biology of normal and acute myeloid leukemia stem cells. International journal of hematology 82, 389-396 (2005).
Eppert et al., Stem cell gene expression programs influence clinical outcome in human leukemia. Nature medicine 17, 1086-1093 (2011).
Feng et al., Molecules that promote or enhance reprogramming of somatic cells to induced pluripotent stem cells. Cell stem cell 4, 301-312 (2009).
Gentles et al., Association of a leukemic stem cell gene expression signature with clinical outcomes in acute myeloid leukemia. JAMA : the journal of the American Medical Association 304, 2706-2715 (2010).
Henry et al., Flavone antagonists bind competitively with 2,3,7,8-tetrachlorodibenzo-p-dioxin (TCDD) to the aryl hydrocarbon receptor but inhibit nuclear uptake and transformation. Molecular pharmacology 55, 716-725 (1999).
Heuser et al., MN1 overexpression induces acute myeloid leukemia in mice and predicts ATRA resistance in patients with AML. Blood 110, 1639-1647 (2007).
Hope et al., Acute myeloid leukemia originates from a hierarchy of leukemic stem cell classes that differ in self-renewal capacity. Nature immunology 5, 738-743 (2004).
Knockaert et al., Independent actions on cyclin-dependent kinases and aryl hydrocarbon receptor mediate the antiproliferative effects of indirubins. Oncogene 23, 4400-4412 (2004).
Krüger et al., Plastic components affect the activation of the aryl hydrocarbon and the androgen receptor. Toxicology 246, 112-123 (2008).
Lapidot et al., A cell initiating human acute myeloid leukaemia after transplantation into SCID mice. Nature 367, 645-648 (1994).
Magnusson et al., Expansion on stromal cells preserves the undifferentiated state of human hematopoietic stem cells despite compromised reconstitution ability. PLoS One 8, e53912 (2013).
Mayani et al., In vitro biology of human myeloid leukemia. Leukemia research 33, 624-637 (2009).
NTP. Report on Carcinogens, Twelfth Edition. Research Triangle Park, NC: U.S. Department of Health and Human Services, Public Health Service, National Toxicology Program. 499 pp. (2011).
Opitz et al., An endogenous tumour-promoting ligand of the human aryl hydrocarbon receptor. Nature 478, 197-203 (2011).
Pearce et al., AML engraftment in the NOD/SCID assay reflects the outcome of AML: implications for our understanding of the heterogeneity of AML. Blood 107, 1166-1173 (2006).
Prud'homme et al., Breast cancer stem-like cells are inhibited by a non-toxic aryl hydrocarbon receptor agonist. PLoS One 5, e13831 (2010).
Swanson et al., DNA binding and protein interactions of the AHR/ARNT heterodimer that facilitate gene activation. Chemico-biological interactions 141, 63-76 (2002).
Taussig et al., Leukemia-initiating cells from some acute myeloid leukemia patients with mutated nucleophosmin reside in the CD34(−) fraction. Blood 115, 1976-1984 (2010).
Woiterski et al., Engraftment of low numbers of pediatric acute lymphoid and myeloid leukemias into NOD/SCID/IL2Rγnull mice reflects individual leukemogenecity and highly correlates with clinical outcome. International Journal of Cancer 133, 1547-1556 (2013).
Xiao et al., Indirubin and meisoindigo in the treatment of chronic myelogenous leukemia in China. Leukemia & lymphoma 43, 1763-1768 (2002).

* cited by examiner

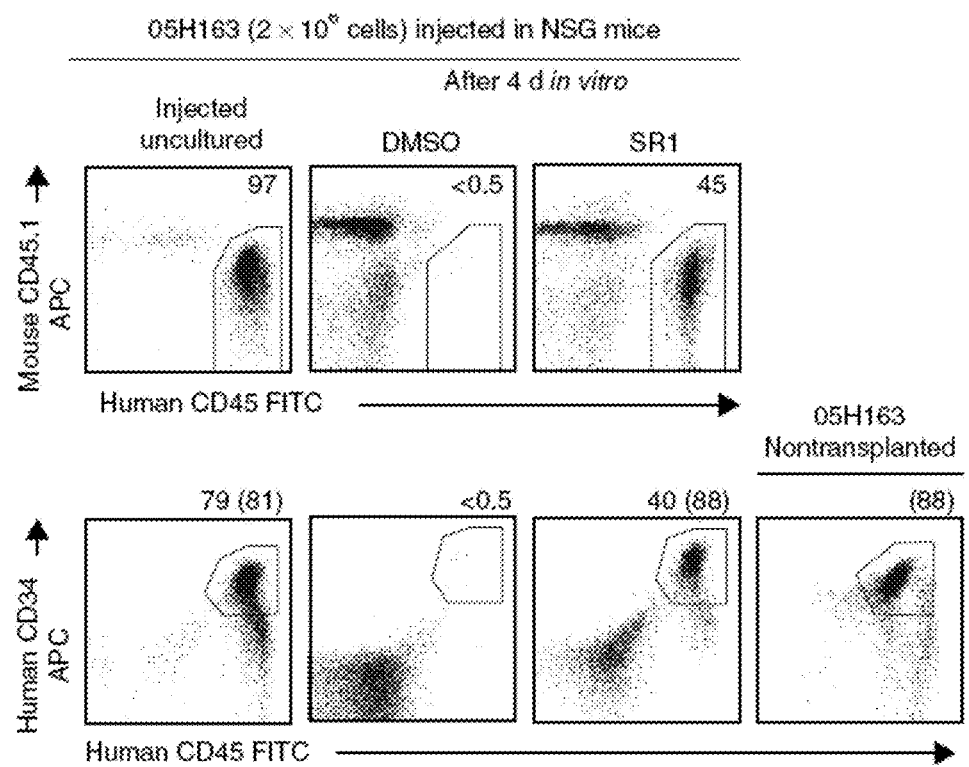
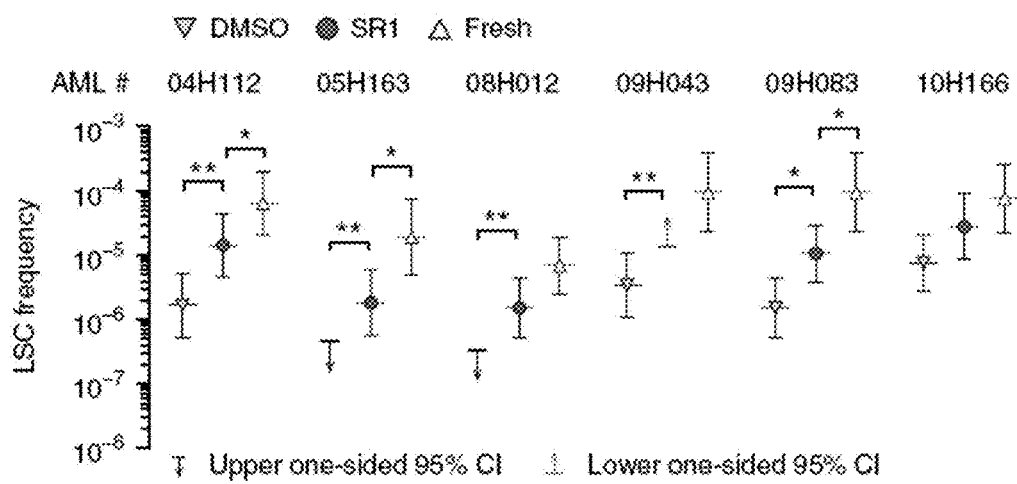
FIG. 4C
FIG. 4D

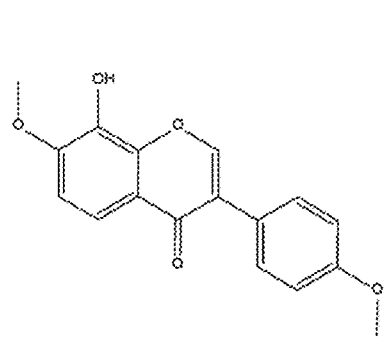
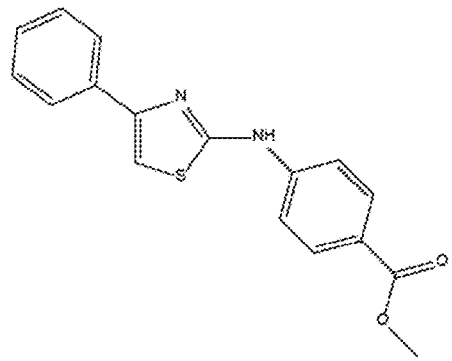
Retusin-7-methylether (C01)    UM0125464 (C02)
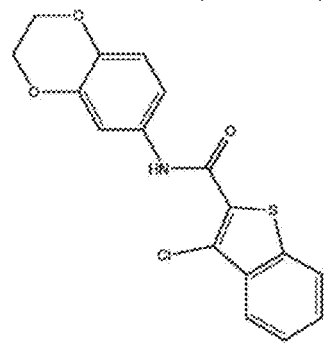
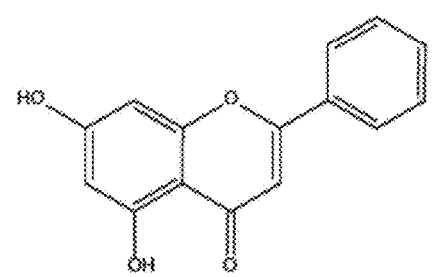
UM0045609 (C03)    Chrysin (C04)
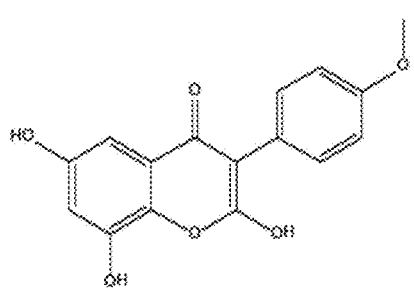
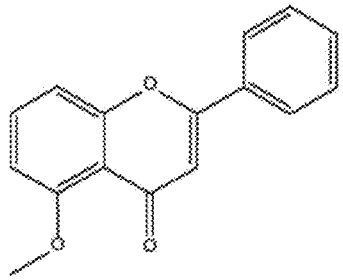
Kaempferide (C06)    5-Methoxyflavone (C08)
FIG. 6

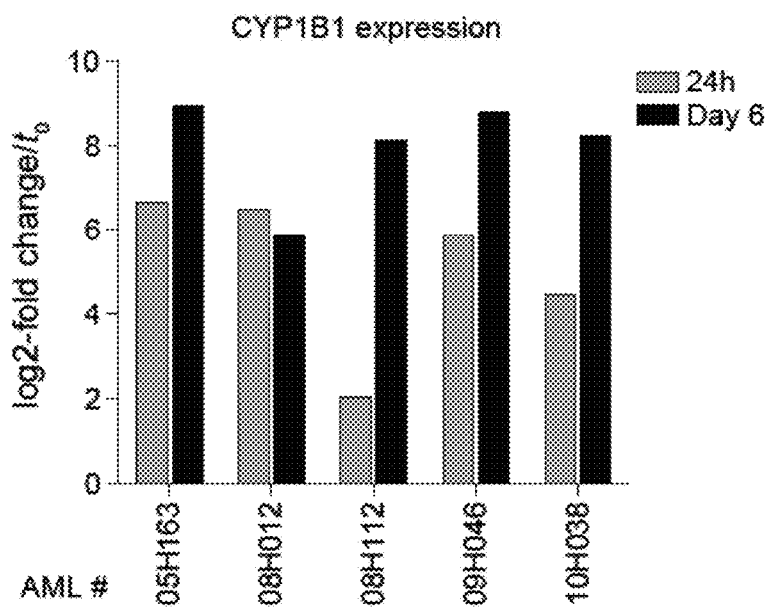
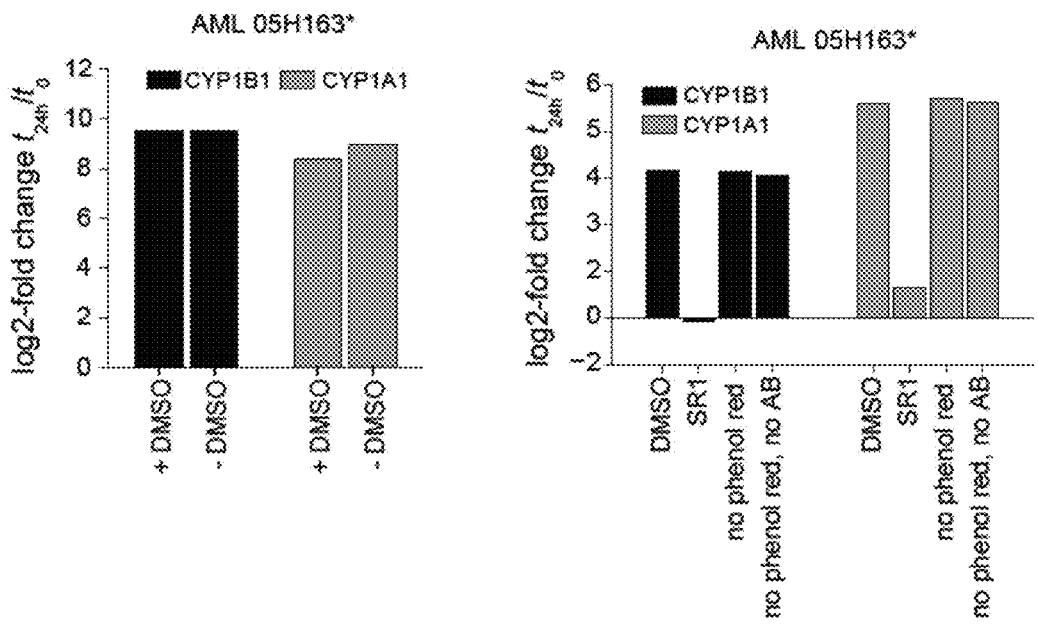
FIG. 7A
FIG. 7B

```
  1 mnsssanity asrkrrkpvq ktvkpipaeg iksnpskrhr drlnteldrl asllpfpqdv
 61 inkldklsvl rlsvsylrak sffdvalkss pternggqdn craanfregl nlqegefllq
121 alngfvlvvt tdalvfyass tiqdylgfqq sdvihqsvye lihtedraef qrqlhwalnp
181 sqctesgqgi eeatglpqtv vcynpdqipp ensplmercf lcrlrclldn ssgflamnfq
241 gklkylhgqk kkgkdgsilp pqlalfaiat plqppsilei rtknfifrtk hkldftpigc
301 dakgrivlgy teaelctrgs gyqfihaadm lycaeshirm iktgesqmiv frlltknnrw
361 twvqsnarll ykngrpdyii vtqrpltdee gtehlrkrnt klpfmfttge avlyeatnpf
421 paimdplplr tkngtsgkds attstlskds lnpssllaam mqqdesiyly passtsstap
481 fennffnesm necrnwqdnt apmgndtilk heqidqpqdv nsfagghpgl fqdsknsdly
541 simknlgidf edirhmqnek ffrndfsgev dfrdidltde iltyvqdsls kspfipsdyq
601 qqqslalnss cmvqehlhle qqqqhhqkqv vvepqqqlcq kmkhmqvngm fenwnsnqfv
661 pfncpqqdpq qynvftdlhg isqefpykse mdsmpytqnf iscnqpvlpq hskcteldyp
721 mgsfepspyp ttssledfvt clqlpenqkh glnpqsaiit pqtcyagavs myqcqpepqh
781 thvgqmqynp vlpgqqafln kfqngvlnet ypaelnninn tqttthlqpl hhpsearpfp
841 dltssgfl
```

FIG. 14A

```
   1 agtggctggg gagtcccgtc gacgctctgt tccgagagcg tgcccggac cgccagctca
  61 gaacaggggc agccgtgtag ccgaacgaa gctgggagca gccgggactg gtggccgcg
 121 cccgagctcc gcaggcggga agcaccctgg atttaggaag tcccgggagc agcgcggcgg
 181 cacctcctc acccaagggg ccgcggcgac ggtcacgggg cgcggcgcca ccgtgagcga
 241 cccaggccag gattctaaat agacggccca ggctcctcct ccgcccggcc cgcctcacct
 301 gcgggcattg ccgcgcgcc tcgccggtg tagacggcac ctgcgccgcc ttgctcgcgg
 361 gtctccgccc ctcgcccacc ctcactgcgc caggcccagg cagctcacct gtactggcgc
 421 gggctgcgga agcctgcgtg agccgaggcg ttgaggcgcg gcgcccacgc cactgtcccg
 481 agaggacgca ggtggagcgg gcgcggcttc gcgaagcccg gcgccggccg ccgcagtggt
 541 cccagcctac accgggttcc ggggaccccgg ccgccagtgc ccggggagta gccgccgccg
 601 tcggctgggc accatgaaca gcagcagcgc caacatcacc tacgccagtc gcaagcggcg
 661 gaagccggtg cagaaaacag taaagccaat cccagctgaa ggaatcaagt caaatccttc
 721 caagcggcat agagaccgac ttaatacaga gttggaccgt ttggctagcc tgctgccttt
 781 cccacaagat gttattaata agttggacaa actttcagtt cttaggctca gcgtcagtta
 841 cctgagagcc aagagcttct ttgatgttgc attaaaatcc tccctactg aaagaaacgg
 901 aggccaggat aactgtagag cagcaaattt cagagaagc ctgaacttac aagaaggaga
 961 attcttatta caggctctga atggctttgt attagttgtc actacagatg ctttggtctt
1021 ttatgcttct tctactatac aagattatct agggtttcag cagtctgatg tcatacatca
1081 gagtgtatat gaacttatcc ataccgaaga ccgagctgaa tttcagcgtc agctacactg
1141 ggcattaaat ccttctcagt gtacagagtc tggacaagga attgaagaag ccactggtct
1201 cccccagaca gtagtctgtt ataacccaga ccagattcct ccagaaaact ctcctttaat
1261 ggagaggtgc ttcatatgtc gtctaaggtg tctgctggat aattcatctg gttttctggc
1321 aatgaatttc caagggaagt taaagtatct tcatggacag aaaaagaaag ggaaagatgg
1381 atcagtactt ccacctcagt tggctttgtt tgcgatagct actccactc agccaccatc
1441 catacttgaa atccggacca aaaattttat ctttagaacc aaacacaaac tagactttcac
1501 acctattggt tgtgatgcca aggaagaat tgttttagga tatactgaag cagagctgtg
1561 cacgagaggc tcaggttatc agtttattca tgcagctgat atgctttatt gtgccagtc
1621 ccatatccga atgattaaga ctgagaaag tggcatgata gttttccggc ttcttacaaa
1681 aaacaaccga tggacttggg tccagtctaa tgcacgcctg ctttataaaa atggaagacc
1741 agattatatc attgtaactc agagaccact aacagatgag gaaggaacag agcatttacg
1801 aaaacgaaat acgaagttgc cttttatgtt taccactgga gaagctgtgt tgtatgaggc
1861 aaccaaccct tttcctgcca taatgatcc cttaccacta aggactaaaa atggcactag
1921 tggaaaagac tctgctacca catccactct aagcaaggac tctctcaatc ctagttccct
1981 cctggctgcc atgatgcaac aagatgagtc tatttatctc tatcctgctt caagtacttc
2041 aagtactgca ccttttgaaa acaactttt caacgaatct atgaatgaat gcagaaattg
2101 gcaagataat actgcaccga tgggaaatga tactatcctg aaacatgagc aaattgacca
2161 gcctcaggat gtgaactcat ttgctggagg tcaccagggg ctctttcaag atagtaaaaa
2221 cagtgacttg tacagcataa tgaaaacct aggcattgat tttgaagaca tcagacacat
2281 gcagaatgaa aaattttca gaaatgactt ttctgactga gttgacttca gagacattga
2341 cttaacggat gaaatcctga cgtatgtcca agattcttta agtaagtctc ccttcatacc
2401 ttcagattat caacagcaac agtccttggc tctgaactca agctgtatgg tacaggaaca
2461 cctacatcta gaacagcaac agcaacatca ccaaaagcaa gtagtagtgg agccacagca
2521 acagctgtgt cagaagatga agcacatgca agtaatggc atgtttgaaa attggaactc
2581 taaccaattc gtgcctttca attgtccaca gcaagaccca caacaatata tgtcttttac
2641 agacttacat gggatcagtc aagagttccc ctacaaatct gaaatggatt ctatgcctta
2701 tacacagaac tttatttcct gtaatcagcc tgtattacca caacattcca aatgtacaga
2761 gctggactac cctatgggga gttttgaacc atccccatac cccactactt ctagtttaga
2821 agattttgtc acttgtttac aacttcctga aaaccaaaag catggattaa atccacagtc
2881 agccataata actcctcaga catgttatgc tgggcgcgtt tcgatgtatc agtgccagcc
2941 agaacctcag cacacccacg tgggtcagat gcagtacaat ccagtactgc caggccaaca
3001 ggcatttta aacaagttc agaatggagt tttaaatgaa acatatccag ctgaattaaa
3061 taacataaat aacactcaga ctaccacaca tcttcagcca cttcatcatc cgtcagaagc
3121 cagacctttt cctgatttga catccagtgg attcctgtaa ttccaagccc aatttgacc
3181 ctggtttttg gattaaatta gtttgtgaag gattatgaa aatataaact gtcactgttg
3241 gacgtcagca agttcacatg gaggcattga tgcatgctat tcacaattat tccaaaccaa
3301 atttaatttt ttgcttttag aaaagggagt ttaaaatgg tatcaaaatt acatatacta
```

FIG. 14B

```
3361 cagtcaagat agaaagggtg ctgccacgga gtggtgaggt accgtctaca tttcacatta
3421 ttctgggcac cacaaaatat acaaaacttt atcaggaaaa ctaagattct tttaaattag
3481 aaaatattct ctatttgaat tatttctgtc acagtaaaaa taaaatactt tgagttttga
3541 gctactggat tcttattagt tccccaaata caaagttaga gaactaaact agttttcct
3601 atcatgttaa cctctgcttt tatctcagat gttaaaataa atggtttggt gcttttata
3661 aaaagataat ctcagtgctt tcctccttca ctgttcatc taagtgcctc acattttt
3721 ctacctataa cactctagga tgtatatttt atataaagta ttcttttct tttaaatt
3781 aatatcttc tgcacacaaa tattatttgt gtttcctaaa tccaaccatt tcattaatt
3841 caggcatatt taactccac tgcttaccta ctttcttcag gtaaagggca aataatgatc
3901 gaaaaaataa ttatttatta cataatttag ttgttctag actatasatg tgctatgtg
3961 ccttatgttg aaaaaattta aagtaaaat gtctttccaa attatttctt aattattata
4021 aaaatattaa gacaatagca cttaaattcc tcaacagtgt tttcagaaga aataaatata
4081 ccactcttta ccttattga tatctccatg atgatagttg aatgttgcaa tgtgaaaaat
4141 ctgctgttaa ctgcaacctt gttattaaa ttgcaagaag ctttatttct agcttttaa
4201 ttaagcaaag cacccattc aatgtgtata aattgtcttt aaaaactgtt tagacctat
4261 aatccttgat aatatatgt gttgactta taatttcgc ttcttagaac agtggaaact
4321 atgtgttttt ctcatatttg aggagtgtta agattgcaga tagcaaggtt tggtgcaaag
4381 tattgtaatg agtgaattga atggtgcatt gtatagatat aatgaacaaa attatttgta
4441 agatatttgc agtttttcat tttaaaaagt ccatacctta tatatgcact taattgttg
4501 gggctttaca tactttatca atgtgtcttt ctaagaaatc aagtaatgaa tccaactgct
4561 taaagttggt attaataaaa agacaaccac atagttcgtt taccttcaaa ctttaggttt
4621 ttttaatgat atactgatct tcattaccaa taggcaaatt aatcaccta ccaactttac
4681 tgtcctaaca tggtttaaaa gaaaaatga caccatcttt tattcttttt ttttttttt
4741 tttgagagag agtcttactc tgccgcccaa actggagtgc agtggcacaa tcttggctca
4801 ctgcaacctc tacctcctgg gttcaagtga ttctcttgcc tcagcctccc gagttgctgg
4861 gattacaggc atgtgccacc atgccagct aatttttgta ttttagtag aaacgggttt
4921 caccatgttg gccagactgg tctcaaactc ctgacctcag gtgagcctcc caccttggcc
4981 tcccaaagtg ctggattac aggcgtgagc cactgcattc agctcttctt ttcttagat
5041 atgagagctg aagagcttag acacatttg catgtattat ttgaaaatct gatggaatcc
5101 caaactgaga tgtattaaaa tacaattttt ggccgggtgc agtggctcac gcctgtaatc
5161 ccagcacttg ggaggggcga ggaggtgga tcacgaggtc aagagatgga gaccatcctg
5221 accaacatgg tgaaacctg tctctactaa aaatacagaa attagctggg catggtggcg
5281 tgagcctgta gtcctagcta ctcaggaggc tgaggcagga gaatagcctg aacctgggaa
5341 tcggaggttg cagagccaag atcgcccac tgcactccag cctggcaata gaccgagact
5401 ccgtctccaa aaaaaaaaaa aatacaattt ttatttcttt tacttttttt agtaagttaa
5461 tgtatataaa aatggcttcg gacaaatat ctctgagttc tgtgtatttt cagtcaaaac
5521 tttaaacctg tagaatcaat ttaagtgttg gaaaaattt gtctgaaaca tttcataatt
5581 tgtttccagc atgaggtatc taaggattta gaccagaggt ctagattaat actctatttt
5641 tacatttaaa ccttttatta taagtcttac ataaaccatt tttgttactc tcttccacat
5701 gttactggat aaattgttta gtggaaaata ggctttttaa tcatgaatat gatgacaatc
5761 agttatacag ttataaaatt aaaagtttga aaagcaatat tgtatatttt tatctatata
5821 aaataactaa aatgtatcta agaataataa aatcacgtta aaccaaatac acgtttgtct
5881 gtattgttaa gtgccaaaca aaggatactt agtgcactgc tacattgtgg gatttatttc
5941 tagatgatgt gcacatctaa ggatatggat gtgtctaatt tagtcttttc ctgtaccagg
6001 ttttcttac aatacctgaa gacttaccag tattctagtg tattatgaag ctttcaacat
6061 tactatgcac aaactagtgt ttttcgatgt tactaaattt taggtaaatg ctttcatggc
6121 ttttttcttc aaaatgttac tgcttacata tatcatgcat agattttgc ttaaagtatg
6181 atttataata tcctcattat caaagttgta tacaataata tataataaaa taacaaatat
6241 gaataat
```

FIG. 14C

| Sample ID | FAB | Karyotype | Age | Sex | Sampling time (at diagnosis/ relapse/ refractory) | Blasts in peripheral blood (%) | Blasts in bone marrow (%) | White blood cell count at diagnosis (x10⁹/l) | CD34 (%) | Tissue used for experiments | NPM-status | FLT3-ITD-status | sample used for indicated experiment(s) | | |
|---|---|---|---|---|---|---|---|---|---|---|---|---|---|---|---|
| | | | | | | | | | | | | | qPCR | in vitro validation | in vivo validation |
| 02H053 | M1 | 46,XY[20] | 60 | M | Diagnosis | NA | 96 | 99 | 0 | Bone marrow | mut | mut | X | | |
| 02H060 | M1 | 45,XY,-21[3]/46,XY[22] | 84 | M | Diagnosis | 92 | 92 | 99.2 | 90 | Blood | ND | ND | | X | |
| 04H001 | M1 | 47,XY,+13[13]/49,XY,+9,+13,+13[7]/46,XY[1] | 63 | M | Diagnosis | 91 | 85 | NA | 87 | Bone marrow | ND | ND | | X | |
| 04H112 | M1 | 46,XX[21] | 64 | F | Diagnosis | 90 | 91 | 361.2 | 36 | Bone marrow | mut | wt | | X | X |
| 05H149 | M1 | 46,XY[20] | 55 | M | Relapse | 80 | NA | 30.5 | 98 | Blood | wt | wt | | X | |
| 05H163 | M1 | 46,XY[22] | 20 | M | Diagnosis | 86 | 92 | 136 | 96 | Blood | wt | wt | X | X | X |
| 06H045 | M2 | 46,XX[22] | 30 | F | Diagnosis | 85 | 70 | 16.6 | 70 | Bone marrow | wt | wt | | X | |

FIG. 15A

| | | | | | | | | | | | |
|---|---|---|---|---|---|---|---|---|---|---|---|
| 06H135 | M0 | 35~42,XY,-5,-8,-9,add(10)(p11),add(11)(q22),-13,?der(13)add(13)(q34),-14,add(15)(p11),-16,-17,-17,-18,+19,-20,-21,+r,+mar1,+mar2,+mar3,+[cp10]/77~83,-X,-Y,-5,-5,-8,-8,-9,-9,?der(9)add(9)(q34),?der(9)add(9)(q34)x2,add(10)(p11),add(10)(p11)x2,-11,add(11)(q22),add(11)(q22)x2,-13,-13,-14,-14,add(15)(p11)x2,-16,-16,-17,-17,-20,-20,-21,+mar1x2,+mar2x2,+mar2x3,inc[cp13] | 65 | M | Diagnosis | 90 | NA | 46 | 98 | Blood | ND | ND | X |
| 07H062 | M1 | 46,XY[20] | 58 | M | Diagnosis | 90 | 94 | 105 | 28 | Blood | mut | mut | X |
| 07H069 | N.A. | 46,XY,inv(7)(q22q36)[20] | 55 | M | Diagnosis | 85 | NA | 80 | 49 | Blood | ND | ND | X | X |
| 08H012 | M1 | 47,XX,+11[21] | 63 | F | Refractory | 98 | NA | 82.6 | 64 | Blood | ND | ND | X | X |
| 08H112 | N.A. | 46,XY[20] | 52 | M | Diagnosis | 85 | 55 | 28.3 | 91(blood)/75(BM) | Blood/Bone Marrow | wt | wt | X |
| 08H118 | M0 | 42~45,X,-X,-3,del(5)(q15q33),del(7)(q22q32),- | 73 | F | Diagnosis | 87 | 67 | 45.9 | 93 | Blood | ND | ND | X |

FIG. 15B

| | | | | | | | | | | | |
|---|---|---|---|---|---|---|---|---|---|---|---|
| 09H054 | N.A. | 46~49,XX,add(5)(q 3?5),- 6,+8,+9,der(11)t(11; 12)(q21;q?15),-12,- 14,-16,-18,-20,- 21,+1-8mar,+2min[ cp22] | 54 | | Diagnosis | 63 | 58 | 80.3 | 87 | Blood | ND | ND | | X | |
| 09H083 | M1 | 46,XX[20] | 63 | F | Diagnosis | 94 | NA | 65.3 | 5 | Blood | mut | mut | | X | X |
| 09H113 | M1 | 46,XY[22] | 56 | M | Diagnosis | 90 | 95 | 68.7 | 97 | Blood | wt | wt | | | X |
| 10H038 | M0 | 46,XX[20] | 67 | F | Diagnosis | 91 | NA | 147.8 | 99 | Blood | wt | wt | | X | X |
| 10H166 | M4 | 46,XY[20] | 63 | M | Diagnosis | 89 | 88 | 226.2 | 1 | Blood | mut | mut | | X | |
| 11H058 | M1 | 46,XY[20] | 58 | M | Diagnosis | 88 | 90 | 1.6 | 1 | Bone marrow | mut | mut | | X | |
| 11H129 | M1 | 47,XY,+10[19]/46,X Y[1] | 62 | M | Diagnosis | 95 | NA | 322.5 | 91 | Blood | ND | ND | | | X |
| 11H192 | M5a | 45,XY,- 18[3]/46,XY[20] | 68 | M | Diagnosis | 48 | 84 | 17.4 | 78 | Bone marrow | wt | mut | | X | X |
| 12H030 | M0 | 46,XY[20] | 78 | M | Diagnosis | 93 | 92 | 144.8 | 94 | Blood | wt | wt | | X | X |

FIG. 15C

| Sample ID | Condition | 1/LSC frequency and 95% CI | | |
|---|---|---|---|---|
| | | Estimate | Upper CI | Lower CI |
| 08H012 | fresh | 145,944 | 53,864 | 395,434 |
| | DMSO** | | 3,071,835 | |
| | SR1 | 660,376 | 228,215 | 1,910,903 |
| | UM729 | 981,886 | 348,596 | 2,765,660 |
| | SR1+UM729 | 660,376 | 228,215 | 1,910,903 |
| 05H163 | fresh | 51,948 | 13,113 | 205,795 |
| | DMSO** | | 2,223,183 | |
| | SR1 | 553,027 | 170,978 | 1,788,760 |
| | UM729 | 7,837,515 | 1,111,580 | 55,260,664 |
| | SR1+UM729 | 141,367 | 40,461 | 493,920 |
| | C05+UM729 | 468,069 | 114,872 | 1,920,820 |
| 09H043 | fresh | 10,544 | 2,547 | 43,652 |
| | DMSO | 293,477 | 94,453 | 911,882 |
| | SR1** | | | 74,446 |
| | UM729 | 178,479 | 63,014 | 505,517 |
| | SR1+UM729 | 62,418 | 21,154 | 184,172 |
| 09H083 | fresh | 10,544 | 2,547 | 43,652 |
| | DMSO | 660,376 | 228,215 | 1,910,903 |
| | SR1 | 95,083 | 34,549 | 261,675 |
| | UM729 | 425,954 | 136,898 | 1,325,340 |
| | SR1+UM729 | 95,083 | 34,549 | 261,675 |
| 10H166 | fresh | 12,989 | 3,808 | 44,302 |
| | DMSO | 132,000 | 48,220 | 361,345 |
| | SR1 | 35,711 | 10,940 | 116,564 |
| | UM729 | 35,711 | 10,940 | 116,564 |
| | SR1+UM729** | | | 74,446 |
| 04H112 | fresh | 15,599 | 5,073 | 47,960 |
| | DMSO | 935,477 | 317,779 | 2,753,857 |
| | SR1 | 70,437 | 22,651 | 219,028 |
| | UM729 | 70,437 | 22,651 | 219,028 |
| | SR1+UM729 | 70,437 | 22,651 | 219,028 |

** one-sided 95% CI were calculated to estimate min./max. LSC frequency when all mice were pos./neg.

SEQUENCE LISTING

```
<160> NUMBER OF SEQ ID NOS: 16

<210> SEQ ID NO 1
<211> LENGTH: 6247
<212> TYPE: DNA
<213> ORGANISM: Homo sapiens
<220> FEATURE:
<221> NAME/KEY: CDS
<222> LOCATION: (614)..(3160)

<400> SEQUENCE: 1
agtggctggg gagtcccgtc gacgctctgt tccgagagcg tgccccggac cgccagctca      60
gaacaggggc agccgtgtag ccgaacggaa gctgggagca gccgggactg gtggcccgcg     120
cccgagctcc gcaggcggga agcaccctgg atttaggaag tcccgggagc agcgcggcgg     180
cacctccctc acccaagggg ccgcggcgac ggtcacgggg cgcggcgcca ccgtgagcga     240
cccaggccag gattctaaat agacggccca ggctcctcct ccgcccgggc cgcctcacct     300
gcgggcattg ccgcgccgcc tccgccggtg tagacggcac ctgcgccgcc ttgctcgcgg     360
gtctccgccc ctcgcccacc ctcactgcgc caggcccagg cagctcacct gtactggcgc     420
gggctgcgga agcctgcgtg agccgaggcg ttgaggcgcg gcgcccacgc cactgtcccg     480
agaggacgca ggtggagcgg gcgcggcttc gcggaacccg gcgccggccg ccgcagtggt     540
cccagcctac accgggttcc ggggacccgg ccgccagtgc ccggggagta gccgccgccg     600
tcggctgggc acc atg aac agc agc agc gcc aac atc acc tac gcc agt       649
               Met Asn Ser Ser Ser Ala Asn Ile Thr Tyr Ala Ser
                 1               5                  10 cgc aag cgg cgg aag ccg gtg cag aaa aca gta aag cca atc cca gct       697
Arg Lys Arg Arg Lys Pro Val Gln Lys Thr Val Lys Pro Ile Pro Ala
             15                  20                  25 gaa gga atc aag tca aat cct tcc aag cgg cat aga gac cga ctt aat       745
Glu Gly Ile Lys Ser Asn Pro Ser Lys Arg His Arg Asp Arg Leu Asn
         30                  35                  40 aca gag ttg gac cgt ttg gct agc ctg ctg cct ttc cca caa gat gtt       793
Thr Glu Leu Asp Arg Leu Ala Ser Leu Leu Pro Phe Pro Gln Asp Val
45                  50                  55                  60
```

```
att aat aag ttg gac aaa ctt tca gtt ctt agg ctc agc gtc agt tac      841
Ile Asn Lys Leu Asp Lys Leu Ser Val Leu Arg Leu Ser Val Ser Tyr
            65                  70                  75 ctg aga gcc aag agc ttc ttt gat gtt gca tta aaa tcc tcc cct act      889
Leu Arg Ala Lys Ser Phe Phe Asp Val Ala Leu Lys Ser Ser Pro Thr
        80                  85                  90 gaa aga aac gga ggc cag gat aac tgt aga gca gca aat ttc aga gaa      937
Glu Arg Asn Gly Gly Gln Asp Asn Cys Arg Ala Ala Asn Phe Arg Glu
    95                  100                 105 ggc ctg aac tta caa gaa gga gaa ttc tta tta cag gct ctg aat ggc      985
Gly Leu Asn Leu Gln Glu Gly Glu Phe Leu Leu Gln Ala Leu Asn Gly
110                 115                 120 ttt gta tta gtt gtc act aca gat gct ttg gtc ttt tat gct tct tct     1033
Phe Val Leu Val Val Thr Thr Asp Ala Leu Val Phe Tyr Ala Ser Ser
125                 130                 135                 140 act ata caa gat tat cta ggg ttt cag cag tct gat gtc ata cat cag     1081
Thr Ile Gln Asp Tyr Leu Gly Phe Gln Gln Ser Asp Val Ile His Gln
            145                 150                 155 agt gta tat gaa ctt atc cat acc gaa gac cga gct gaa ttt cag cgt     1129
Ser Val Tyr Glu Leu Ile His Thr Glu Asp Arg Ala Glu Phe Gln Arg
        160                 165                 170 cag cta cac tgg gca tta aat cct tct cag tgt aca gag tct gga caa     1177
Gln Leu His Trp Ala Leu Asn Pro Ser Gln Cys Thr Glu Ser Gly Gln
    175                 180                 185 gga att gaa gaa gcc act ggt ctc ccc cag aca gta gtc tgt tat aac     1225
Gly Ile Glu Glu Ala Thr Gly Leu Pro Gln Thr Val Val Cys Tyr Asn
190                 195                 200 cca gac cag att cct cca gaa aac tct cct tta atg gag agg tgc ttc     1273
Pro Asp Gln Ile Pro Pro Glu Asn Ser Pro Leu Met Glu Arg Cys Phe
205                 210                 215                 220 ata tgt cgt cta agg tgt ctg ctg gat aat tca tct ggt ttt ctg gca     1321
Ile Cys Arg Leu Arg Cys Leu Leu Asp Asn Ser Ser Gly Phe Leu Ala
            225                 230                 235 atg aat ttc caa ggg aag tta aag tat ctt cat gga cag aaa aag aaa     1369
Met Asn Phe Gln Gly Lys Leu Lys Tyr Leu His Gly Gln Lys Lys Lys
        240                 245                 250 ggg aaa gat gga tca ata ctt cca cct cag ttg gct ttg ttt gcg ata     1417
Gly Lys Asp Gly Ser Ile Leu Pro Pro Gln Leu Ala Leu Phe Ala Ile
    255                 260                 265 gct act cca ctt cag cca cca tcc ata ctt gaa atc cgg acc aaa aat     1465
Ala Thr Pro Leu Gln Pro Pro Ser Ile Leu Glu Ile Arg Thr Lys Asn
270                 275                 280 ttt atc ttt aga acc aaa cac aaa cta gac ttc aca cct att ggt tgt     1513
Phe Ile Phe Arg Thr Lys His Lys Leu Asp Phe Thr Pro Ile Gly Cys
285                 290                 295                 300 gat gcc aaa gga aga att gtt tta gga tat act gaa gca gag ctg tgc     1561
Asp Ala Lys Gly Arg Ile Val Leu Gly Tyr Thr Glu Ala Glu Leu Cys
            305                 310                 315 acg aga ggc tca ggt tat cag ttt att cat gca gct gat atg ctt tat     1609
Thr Arg Gly Ser Gly Tyr Gln Phe Ile His Ala Ala Asp Met Leu Tyr
        320                 325                 330 tgt gcc gag tcc cat atc cga atg att aag act gga gaa agt ggc atg     1657
Cys Ala Glu Ser His Ile Arg Met Ile Lys Thr Gly Glu Ser Gly Met
    335                 340                 345 ata gtt ttc cgg ctt ctt aca aaa aac aac cga tgg act tgg gtc cag     1705
Ile Val Phe Arg Leu Leu Thr Lys Asn Asn Arg Trp Thr Trp Val Gln
350                 355                 360 tct aat gca cgc ctg ctt tat aaa aat gga aga cca gat tat atc att     1753
Ser Asn Ala Arg Leu Leu Tyr Lys Asn Gly Arg Pro Asp Tyr Ile Ile
```

```
                                        -continued
365                 370                 375                 380 gta act cag aga cca cta aca gat gag gaa gga aca gag cat tta cga        1801
Val Thr Gln Arg Pro Leu Thr Asp Glu Glu Gly Thr Glu His Leu Arg
                385                 390                 395 aaa cga aat acg aag ttg cct ttt atg ttt acc act gga gaa gct gtg        1849
Lys Arg Asn Thr Lys Leu Pro Phe Met Phe Thr Thr Gly Glu Ala Val
            400                 405                 410 ttg tat gag gca acc aac cct ttt cct gcc ata atg gat ccc tta cca        1897
Leu Tyr Glu Ala Thr Asn Pro Phe Pro Ala Ile Met Asp Pro Leu Pro
        415                 420                 425 cta agg act aaa aat ggc act agt gga aaa gac tct gct acc aca tcc        1945
Leu Arg Thr Lys Asn Gly Thr Ser Gly Lys Asp Ser Ala Thr Thr Ser
    430                 435                 440 act cta agc aag gac tct ctc aat cct agt tcc ctg ctg gct gcc atg        1993
Thr Leu Ser Lys Asp Ser Leu Asn Pro Ser Ser Leu Leu Ala Ala Met
445                 450                 455                 460 atg caa caa gat gag tct att tat ctc tat cct gct tca agt act tca        2041
Met Gln Gln Asp Glu Ser Ile Tyr Leu Tyr Pro Ala Ser Ser Thr Ser
                465                 470                 475 agt act gca cct ttt gaa aac aac ttt ttc aac gaa tct atg aat gaa        2089
Ser Thr Ala Pro Phe Glu Asn Asn Phe Phe Asn Glu Ser Met Asn Glu
            480                 485                 490 tgc aga aat tgg caa gat aat act gca ccg atg gga aat gat act atc        2137
Cys Arg Asn Trp Gln Asp Asn Thr Ala Pro Met Gly Asn Asp Thr Ile
        495                 500                 505 ctg aaa cat gag caa att gac cag cct cag gat gtg aac tca ttt gct        2185
Leu Lys His Glu Gln Ile Asp Gln Pro Gln Asp Val Asn Ser Phe Ala
    510                 515                 520 gga ggt cac cca ggg ctc ttt caa gat agt aaa aac agt gac ttg tac        2233
Gly Gly His Pro Gly Leu Phe Gln Asp Ser Lys Asn Ser Asp Leu Tyr
525                 530                 535                 540 agc ata atg aaa aac cta ggc att gat ttt gaa gac atc aga cac atg        2281
Ser Ile Met Lys Asn Leu Gly Ile Asp Phe Glu Asp Ile Arg His Met
                545                 550                 555 cag aat gaa aaa ttt ttc aga aat gat ttt tct ggt gag gtt gac ttc        2329
Gln Asn Glu Lys Phe Phe Arg Asn Asp Phe Ser Gly Glu Val Asp Phe
            560                 565                 570 aga gac att gac tta acg gat gaa atc ctg acg tat gtc caa gat tct        2377
Arg Asp Ile Asp Leu Thr Asp Glu Ile Leu Thr Tyr Val Gln Asp Ser
        575                 580                 585 tta agt aag tct ccc ttc ata cct tca gat tat caa cag caa cag tcc        2425
Leu Ser Lys Ser Pro Phe Ile Pro Ser Asp Tyr Gln Gln Gln Gln Ser
    590                 595                 600 ttg gct ctg aac tca agc tgt atg gta cag gaa cac cta cat cta gaa        2473
Leu Ala Leu Asn Ser Ser Cys Met Val Gln Glu His Leu His Leu Glu
605                 610                 615                 620 cag caa cag caa cat cac caa aag caa gta gta gtg gag cca cag caa        2521
Gln Gln Gln Gln His His Gln Lys Gln Val Val Val Glu Pro Gln Gln
                625                 630                 635 cag ctg tgt cag aag atg aag cac atg caa gtt aat ggc atg ttt gaa        2569
Gln Leu Cys Gln Lys Met Lys His Met Gln Val Asn Gly Met Phe Glu
            640                 645                 650 aat tgg aac tct aac caa ttc gtg cct ttc aat tgt cca cag caa gac        2617
Asn Trp Asn Ser Asn Gln Phe Val Pro Phe Asn Cys Pro Gln Gln Asp
        655                 660                 665 cca caa caa tat aat gtc ttt aca gac tta cat ggg atc agt caa gag        2665
Pro Gln Gln Tyr Asn Val Phe Thr Asp Leu His Gly Ile Ser Gln Glu
    670                 675                 680 ttc ccc tac aaa tct gaa atg gat tct atg cct tat aca cag aac ttt        2713
```

```
              Phe Pro Tyr Lys Ser Glu Met Asp Ser Met Pro Tyr Thr Gln Asn Phe
              685                 690                 695                 700 att tcc tgt aat cag cct gta tta cca caa cat tcc aaa tgt aca gag            2761
Ile Ser Cys Asn Gln Pro Val Leu Pro Gln His Ser Lys Cys Thr Glu
                705                 710                 715 ctg gac tac cct atg ggg agt ttt gaa cca tcc cca tac ccc act act            2809
Leu Asp Tyr Pro Met Gly Ser Phe Glu Pro Ser Pro Tyr Pro Thr Thr
                    720                 725                 730 tct agt tta gaa gat ttt gtc act tgt tta caa ctt cct gaa aac caa            2857
Ser Ser Leu Glu Asp Phe Val Thr Cys Leu Gln Leu Pro Glu Asn Gln
                735                 740                 745 aag cat gga tta aat cca cag tca gcc ata ata act cct cag aca tgt            2905
Lys His Gly Leu Asn Pro Gln Ser Ala Ile Ile Thr Pro Gln Thr Cys
                750                 755                 760 tat gct ggg gcc gtg tcg atg tat cag tgc cag cca gaa cct cag cac            2953
Tyr Ala Gly Ala Val Ser Met Tyr Gln Cys Gln Pro Glu Pro Gln His
765                 770                 775                 780 acc cac gtg ggt cag atg cag tac aat cca gta ctg cca ggc caa cag            3001
Thr His Val Gly Gln Met Gln Tyr Asn Pro Val Leu Pro Gly Gln Gln
                    785                 790                 795 gca ttt tta aac aag ttt cag aat gga gtt tta aat gaa aca tat cca            3049
Ala Phe Leu Asn Lys Phe Gln Asn Gly Val Leu Asn Glu Thr Tyr Pro
                800                 805                 810 gct gaa tta aat aac ata aat aac act cag act acc aca cat ctt cag            3097
Ala Glu Leu Asn Asn Ile Asn Asn Thr Gln Thr Thr Thr His Leu Gln
                815                 820                 825 cca ctt cat cat ccg tca gaa gcc aga cct ttt cct gat ttg aca tcc            3145
Pro Leu His His Pro Ser Glu Ala Arg Pro Phe Pro Asp Leu Thr Ser
830                 835                 840 agt gga ttc ctg taa ttccaagccc aattttgacc ctggttttg gattaaatta             3200
Ser Gly Phe Leu
845 gtttgtgaag gattatggaa aaataaaact gtcactgttg gacgtcagca agttcacatg          3260 gaggcattga tgcatgctat tcacaattat tccaaaccaa attttaattt ttgcttttag          3320 aaaagggagt ttaaaaatgg tatcaaaatt acatatacta cagtcaagat agaaagggtg          3380 ctgccacgga gtggtgaggt accgtctaca tttcacatta ttctgggcac cacaaaatat          3440 acaaaacttt atcagggaaa ctaagattct tttaaattag aaaatattct ctatttgaat          3500 tatttctgtc acagtaaaaa taaaatactt tgagttttga gctactggat tcttattagt          3560 tccccaaata caaagttaga gaactaaact agttttttcct atcatgttaa cctctgcttt         3620 tatctcagat gttaaaataa atggtttggt gcttttttata aaaagataat ctcagtgctt         3680 tcctccttca ctgtttcatc taagtgcctc acattttttt ctacctataa cactctagga         3740 tgtatatttt ataaagta ttcttttct ttttaaatt aatatcttc tgcacacaaa              3800 tattatttgt gtttcctaaa tccaaccatt tcattaatt caggcatatt ttaactccac          3860 tgcttaccta ctttcttcag gtaaagggca aataatgatc gaaaaaataa ttatttatta         3920 cataatttag ttgtttctag actataaatg ttgctatgtg ccttatgttg aaaaaattta         3980 aaagtaaaat gtcttttccaa attatttctt aattattata aaatatatta gacaatagca         4040 cttaaattcc tcaacagtgt tttcagaaga aataaatata ccactcttta cctttattga        4100 tatctccatg atgatagttg aatgttgcaa tgtgaaaaat ctgctgttaa ctgcaacctt         4160 gtttattaaa ttgcaagaag ctttatttct agctttttaa ttaagcaaag cacccatttc         4220 aatgtgtata aattgtcttt aaaaactgtt ttagacctat aatccttgat aatatattgt        4280
```

| | | | | |
|---|---|---|---|---|
| gttgacttta | taaatttcgc | ttcttagaac | agtggaaact | atgtgttttt ctcatatttg | 4340 |
| aggagtgtta | agattgcaga | tagcaaggtt | tggtgcaaag | tattgtaatg agtgaattga | 4400 |
| atggtgcatt | gtatagatat | aatgaacaaa | attatttgta | agatatttgc agttttcat | 4460 |
| tttaaaaagt | ccatacctta | tatatgcact | taatttgttg | gggctttaca tactttatca | 4520 |
| atgtgtcttt | ctaagaaatc | aagtaatgaa | tccaactgct | taaagttggt attaataaaa | 4580 |
| agacaaccac | atagttcgtt | taccttcaaa | ctttaggttt | ttttaatgat atactgatct | 4640 |
| tcattaccaa | taggcaaatt | aatcacccta | ccaactttac | tgtcctaaca tggtttaaaa | 4700 |
| gaaaaaatga | caccatctttt | tattcttttt | tttttttttt | tttgagagag agtcttactc | 4760 |
| tgccgcccaa | actggagtgc | agtggcacaa | tcttggctca | ctgcaacctc tacctcctgg | 4820 |
| gttcaagtga | ttctcttgcc | tcagcctccc | gagttgctgg | gattacaggc atgtgccacc | 4880 |
| atgcccagct | aattttgta | tttttagtag | aaacgggttt | caccatgttg gccagactgg | 4940 |
| tctcaaactc | ctgacctcag | gtgagcctcc | caccttggcc | tcccaaagtg ctgggattac | 5000 |
| aggcgtgagc | cactgcattc | agctcttctt | ttctttagat | atgagagctg aagagcttag | 5060 |
| acacattttg | catgtattat | ttgaaaatct | gatggaatcc | caaactgaga tgtattaaaa | 5120 |
| tacaattttt | ggccgggtgc | agtggctcac | gcctgtaatc | ccagcacttg gggagggcga | 5180 |
| ggagggtgga | tcacgaggtc | aagagatgga | gaccatcctg | accaacatgg tgaaaccctg | 5240 |
| tctctactaa | aaatacagaa | attagctggg | catggtggcg | tgagcctgta gtcctagcta | 5300 |
| ctcaggaggc | tgaggcagga | gaatagcctg | aacctgggaa | tcggaggttg cagagccaag | 5360 |
| atcgccccac | tgcactccag | cctggcaata | gaccgagact | ccgtctccaa aaaaaaaaaa | 5420 |
| aatacaattt | ttatttcttt | tacttttttt | agtaagttaa | tgtatataaa aatggcttcg | 5480 |
| gacaaaatat | ctctgagttc | tgtgtatttt | cagtcaaaac | tttaaacctg tagaatcaat | 5540 |
| ttaagtgttg | gaaaaaattt | gtctgaaaca | tttcataatt | tgtttccagc atgaggtatc | 5600 |
| taaggattta | gaccagaggt | ctagattaat | actctatttt | tacatttaaa ccttttatta | 5660 |
| taagtcttac | ataaaccatt | tttgttactc | tcttccacat | gttactggat aaattgttta | 5720 |
| gtggaaaata | ggcttttttaa | tcatgaatat | gatgacaatc | agttatacag ttataaaatt | 5780 |
| aaaagtttga | aaagcaatat | tgtatatttt | tatctatata | aaataactaa aatgtatcta | 5840 |
| agaataataa | aatcacgtta | aaccaaatac | acgtttgtct | gtattgttaa gtgccaaaca | 5900 |
| aaggatactt | agtgcactgc | tacattgtgg | gatttatttc | tagatgatgt gcacatctaa | 5960 |
| ggatatggat | gtgtctaatt | tagtcttttc | ctgtaccagg | ttttttcttac aatacctgaa | 6020 |
| gacttaccag | tattctagtg | tattatgaag | ctttcaacat | tactatgcac aaactagtgt | 6080 |
| ttttcgatgt | tactaaattt | taggtaaatg | ctttcatggc | ttttttcttc aaaatgttac | 6140 |
| tgcttacata | tatcatgcat | agattttgc | ttaaagtatg atttataata | tcctcattat | 6200 |
| caaagttgta | tacaataata | tataataaaa | taacaaatat | gaataat | 6247 |

<210> SEQ ID NO 2
<211> LENGTH: 848
<212> TYPE: PRT
<213> ORGANISM: Homo sapiens

<400> SEQUENCE: 2

Met Asn Ser Ser Ser Ala Asn Ile Thr Tyr Ala Ser Arg Lys Arg Arg
1               5                   10                  15

Lys Pro Val Gln Lys Thr Val Lys Pro Ile Pro Ala Glu Gly Ile Lys
            20                  25                  30

```
Ser Asn Pro Ser Lys Arg His Arg Asp Arg Leu Asn Thr Glu Leu Asp
        35                  40                  45

Arg Leu Ala Ser Leu Leu Pro Phe Pro Gln Asp Val Ile Asn Lys Leu
 50                  55                  60

Asp Lys Leu Ser Val Leu Arg Leu Ser Val Ser Tyr Leu Arg Ala Lys
 65                  70                  75                  80

Ser Phe Phe Asp Val Ala Leu Lys Ser Ser Pro Thr Glu Arg Asn Gly
                 85                  90                  95

Gly Gln Asp Asn Cys Arg Ala Ala Asn Phe Arg Glu Gly Leu Asn Leu
                100                 105                 110

Gln Glu Gly Glu Phe Leu Leu Gln Ala Leu Asn Gly Phe Val Leu Val
            115                 120                 125

Val Thr Thr Asp Ala Leu Val Phe Tyr Ala Ser Ser Thr Ile Gln Asp
        130                 135                 140

Tyr Leu Gly Phe Gln Gln Ser Asp Val Ile His Gln Ser Val Tyr Glu
145                 150                 155                 160

Leu Ile His Thr Glu Asp Arg Ala Glu Phe Gln Arg Gln Leu His Trp
                165                 170                 175

Ala Leu Asn Pro Ser Gln Cys Thr Glu Ser Gly Gln Gly Ile Glu Glu
            180                 185                 190

Ala Thr Gly Leu Pro Gln Thr Val Val Cys Tyr Asn Pro Asp Gln Ile
        195                 200                 205

Pro Pro Glu Asn Ser Pro Leu Met Glu Arg Cys Phe Ile Cys Arg Leu
    210                 215                 220

Arg Cys Leu Leu Asp Asn Ser Ser Gly Phe Leu Ala Met Asn Phe Gln
225                 230                 235                 240

Gly Lys Leu Lys Tyr Leu His Gly Gln Lys Lys Gly Lys Asp Gly
                245                 250                 255

Ser Ile Leu Pro Pro Gln Leu Ala Leu Phe Ala Ile Ala Thr Pro Leu
                260                 265                 270

Gln Pro Pro Ser Ile Leu Glu Ile Arg Thr Lys Asn Phe Ile Phe Arg
    275                 280                 285

Thr Lys His Lys Leu Asp Phe Thr Pro Ile Gly Cys Asp Ala Lys Gly
        290                 295                 300

Arg Ile Val Leu Gly Tyr Thr Glu Ala Glu Leu Cys Thr Arg Gly Ser
305                 310                 315                 320

Gly Tyr Gln Phe Ile His Ala Ala Asp Met Leu Tyr Cys Ala Glu Ser
                325                 330                 335

His Ile Arg Met Ile Lys Thr Gly Glu Ser Gly Met Ile Val Phe Arg
            340                 345                 350

Leu Leu Thr Lys Asn Asn Arg Trp Thr Trp Val Gln Ser Asn Ala Arg
        355                 360                 365

Leu Leu Tyr Lys Asn Gly Arg Pro Asp Tyr Ile Ile Val Thr Gln Arg
    370                 375                 380

Pro Leu Thr Asp Glu Glu Gly Thr Glu His Leu Arg Lys Arg Asn Thr
385                 390                 395                 400

Lys Leu Pro Phe Met Phe Thr Thr Gly Glu Ala Val Leu Tyr Glu Ala
                405                 410                 415

Thr Asn Pro Phe Pro Ala Ile Met Asp Pro Leu Pro Leu Arg Thr Lys
            420                 425                 430

Asn Gly Thr Ser Gly Lys Asp Ser Ala Thr Thr Ser Thr Leu Ser Lys
        435                 440                 445
```

```
Asp Ser Leu Asn Pro Ser Ser Leu Leu Ala Ala Met Met Gln Gln Asp
    450                 455                 460
Glu Ser Ile Tyr Leu Tyr Pro Ala Ser Ser Thr Ser Ser Thr Ala Pro
465                 470                 475                 480
Phe Glu Asn Asn Phe Asn Glu Ser Met Asn Glu Cys Arg Asn Trp
                485                 490                 495
Gln Asp Asn Thr Ala Pro Met Gly Asn Asp Thr Ile Leu Lys His Glu
                500                 505                 510
Gln Ile Asp Gln Pro Gln Asp Val Asn Ser Phe Ala Gly Gly His Pro
            515                 520                 525
Gly Leu Phe Gln Asp Ser Lys Asn Ser Asp Leu Tyr Ser Ile Met Lys
    530                 535                 540
Asn Leu Gly Ile Asp Phe Glu Asp Ile Arg His Met Gln Asn Glu Lys
545                 550                 555                 560
Phe Phe Arg Asn Asp Phe Ser Gly Glu Val Asp Phe Arg Asp Ile Asp
                565                 570                 575
Leu Thr Asp Glu Ile Leu Thr Tyr Val Gln Asp Ser Leu Ser Lys Ser
            580                 585                 590
Pro Phe Ile Pro Ser Asp Tyr Gln Gln Gln Ser Leu Ala Leu Asn
    595                 600                 605
Ser Ser Cys Met Val Gln Glu His Leu His Leu Glu Gln Gln Gln Gln
    610                 615                 620
His His Gln Lys Gln Val Val Glu Pro Gln Gln Leu Cys Gln
625                 630                 635                 640
Lys Met Lys His Met Gln Val Asn Gly Met Phe Glu Asn Trp Asn Ser
                645                 650                 655
Asn Gln Phe Val Pro Phe Asn Cys Pro Gln Gln Asp Pro Gln Gln Tyr
                660                 665                 670
Asn Val Phe Thr Asp Leu His Gly Ile Ser Gln Glu Phe Pro Tyr Lys
            675                 680                 685
Ser Glu Met Asp Ser Met Pro Tyr Thr Gln Asn Phe Ile Ser Cys Asn
    690                 695                 700
Gln Pro Val Leu Pro Gln His Ser Lys Cys Thr Glu Leu Asp Tyr Pro
705                 710                 715                 720
Met Gly Ser Phe Glu Pro Ser Pro Tyr Pro Thr Thr Ser Ser Leu Glu
                725                 730                 735
Asp Phe Val Thr Cys Leu Gln Leu Pro Glu Asn Gln Lys His Gly Leu
            740                 745                 750
Asn Pro Gln Ser Ala Ile Ile Thr Pro Gln Thr Cys Tyr Ala Gly Ala
    755                 760                 765
Val Ser Met Tyr Gln Cys Gln Pro Glu Pro Gln His Thr His Val Gly
    770                 775                 780
Gln Met Gln Tyr Asn Pro Val Leu Pro Gly Gln Gln Ala Phe Leu Asn
785                 790                 795                 800
Lys Phe Gln Asn Gly Val Leu Asn Glu Thr Tyr Pro Ala Glu Leu Asn
                805                 810                 815
Asn Ile Asn Asn Thr Gln Thr Thr Thr His Leu Gln Pro Leu His His
            820                 825                 830
Pro Ser Glu Ala Arg Pro Phe Pro Asp Leu Thr Ser Ser Gly Phe Leu
    835                 840                 845

<210> SEQ ID NO 3
<211> LENGTH: 21
<212> TYPE: DNA
```

```
<213> ORGANISM: Artificial Sequence
<220> FEATURE:
<223> OTHER INFORMATION: siRNA

<400> SEQUENCE: 3
uacuuccacc ucaguuggct t                                              21

<210> SEQ ID NO 4
<211> LENGTH: 21
<212> TYPE: DNA
<213> ORGANISM: Artificial Sequence
<220> FEATURE:
<223> OTHER INFORMATION: siRNA

<400> SEQUENCE: 4
ttaugaaggu ggagucaacc g                                              21

<210> SEQ ID NO 5
<211> LENGTH: 21
<212> TYPE: DNA
<213> ORGANISM: Artificial Sequence
<220> FEATURE:
<223> OTHER INFORMATION: siRNA

<400> SEQUENCE: 5
gccgaguccc auauccgaau g                                              21

<210> SEQ ID NO 6
<211> LENGTH: 21
<212> TYPE: DNA
<213> ORGANISM: Artificial Sequence
<220> FEATURE:
<223> OTHER INFORMATION: siRNA

<400> SEQUENCE: 6
gacguauguc caagauucuu u                                              21

<210> SEQ ID NO 7
<211> LENGTH: 19
<212> TYPE: DNA
<213> ORGANISM: Homo sapiens

<400> SEQUENCE: 7
agccacatcg ctcagacac                                                 19

<210> SEQ ID NO 8
<211> LENGTH: 19
<212> TYPE: DNA
<213> ORGANISM: Homo sapiens

<400> SEQUENCE: 8
gcccaatacg accaaatcc                                                 19

<210> SEQ ID NO 9
<211> LENGTH: 21
<212> TYPE: DNA
<213> ORGANISM: Homo sapiens

<400> SEQUENCE: 9
aaaggctttt acatccccaa g                                              21

<210> SEQ ID NO 10
<211> LENGTH: 20
<212> TYPE: DNA
<213> ORGANISM: Homo sapiens
```

```
<400> SEQUENCE: 10
gggttgaccc atagcttctg                                              20

<210> SEQ ID NO 11
<211> LENGTH: 20
<212> TYPE: DNA
<213> ORGANISM: Homo sapiens

<400> SEQUENCE: 11
cggccactat cactgacatc                                              20

<210> SEQ ID NO 12
<211> LENGTH: 20
<212> TYPE: DNA
<213> ORGANISM: Homo sapiens

<400> SEQUENCE: 12
ctcgagtctg cacatcagga                                              20

<210> SEQ ID NO 13
<211> LENGTH: 18
<212> TYPE: DNA
<213> ORGANISM: Homo sapiens

<400> SEQUENCE: 13
tgcttcatct gccgtgtg                                                18

<210> SEQ ID NO 14
<211> LENGTH: 18
<212> TYPE: DNA
<213> ORGANISM: Homo sapiens

<400> SEQUENCE: 14
agctgccaag cctgtgac                                                18

<210> SEQ ID NO 15
<211> LENGTH: 18
<212> TYPE: DNA
<213> ORGANISM: Homo sapiens

<400> SEQUENCE: 15
agccggtgca gaaaacag                                                18

<210> SEQ ID NO 16
<211> LENGTH: 19
<212> TYPE: DNA
<213> ORGANISM: Homo sapiens

<400> SEQUENCE: 16
ctatgccgct tggaaggat                                               19
```

METHODS TO MODULATE ACUTE MYELOID LEUKEMIA STEM/PROGENITOR CELL EXPANSION AND/OR DIFFERENTIATION

CROSS REFERENCE TO RELATED APPLICATIONS

The present application claims the benefit of U.S. Provisional Application Ser. No. 61/824,734 filed on May 17, 2013, which is incorporated herein by reference in its entirety.

FIELD OF THE INVENTION

The present invention generally relates to cancer, and more particularly to the management of acute myeloid leukemia (AML).

REFERENCE TO SEQUENCE LISTING

Pursuant to 37 C.F.R. 1.821(c), a sequence listing is submitted herewith as an ASCII compliant text file named Sequence_Listing_ST25.txt, that was created on Apr. 4, 2014 and having a size of ~27 kilobytes. The content of the aforementioned file is hereby incorporated by reference in its entirety.

BACKGROUND OF THE INVENTION

AML is a clonal disorder clinically presenting as increased proliferation of heterogeneous and undifferentiated myeloid blasts. Understanding the biology of human AML stem/progenitor cells is an important prerequisite for the development of more efficacious therapeutic strategies in the treatment of AML as current therapies fail to permanently eradicate the disease in a significant proportion of patients (Patel, J., et al. *The New England Journal of Medicine* 366, 1079-1089 (2012)). Studies by Lapidot and Dick (Lapidot, T., et al. *Nature* 367, 645-648 (1994)) are at the basis of the current understanding of AML as a heterogeneous disease consisting of cells which differ from each other with regards to proliferative potential, cell cycle kinetics, resistance to chemotherapy and self-renewal capacity thus caricaturing the hierarchy of the normal hematopoietic system (Bonnet, D. & Dick, J. *Nature medicine* 3, 730-737 (1997); Hope, K., Jin, L. & Dick, J. *Nature immunology* 5, 738-743 (2004); Ishikawa, F., et al. *Nature biotechnology* 25, 1315-1321 (2007); Pearce, D., et al. *Blood* 107, 1166-1173 (2006)). Leukemia initiating cells (LIC) which are defined by their potential to engraft immunocompromised mice are at the apex of this hierarchy and share some important features with normal hematopoietic stem cells (HSC) as the ability to self-renew and to recapitulate the diversity of the hierarchy. Engraftment potential of human leukemic cells in immunocompromised mice has been correlated with clinical outcome in adult (Pearce D. et al., supra) and more recently pediatric leukemia patients (Woiterski, J., et al. *International journal of cancer* March 23. doi: 10.1002/ijc.28170. [Epub ahead of print] (2013)). Furthermore, leukemic stem cell associated gene expression signatures (Eppert, K., et al. *Nature medicine* 17, 1086-1093 (2011); Gentles, A., Plevritis, S., Majeti, R. & Alizadeh, A. *JAMA: the journal of the American Medical Association* 304, 2706-2715 (2010)) identified by comparative microarray studies have been associated with worse survival providing evidence for clinical relevance of these experimentally defined cells. However, LICs rapidly differentiate or/and undergo apoptosis when deprived of their in vivo environment and exposed to currently available in vitro conditions, which is a major obstacle in the development of LIC targeted therapies and casts doubt on the interpretation of results emanating from ex vivo treatment of these cells. Cell lines which have been used in the past for drug screenings have overcome these constraints but do not reflect the hierarchical organization of the primary disease anymore which makes them an inappropriate tool for the development of LIC targeted therapies.

There is thus a need for strategies to modulate AML stem/progenitor cell expansion and/or differentiation.

The present description refers to a number of documents, the content of which is herein incorporated by reference in their entirety.

SUMMARY OF THE INVENTION

More specifically, in accordance with the present invention, there is provided In an aspect, the present invention provides a method for (i) inhibiting or preventing the differentiation of acute myeloid leukemia (AML) initiating cells ex vivo, and/or (ii) promoting the expansion or maintenance of undifferentiated primary acute myeloid leukemia (AML) blasts ex vivo, and/or (iii) partially rescuing AML initiating activity ex vivo, said method comprising contacting said cells with (a) a suppressor of the Aryl hydrocarbon Receptor (AhR) and/or (b) a compound of general formula I or II:

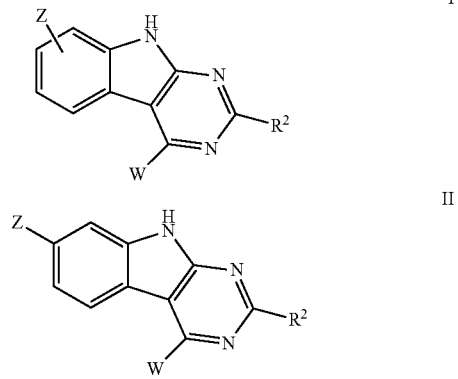

or a salt or a prodrug thereof,
wherein:
Z is
  1) —P(O)(OR$^1$)(OR$^1$),
  2) —C(O)OR$^1$,
  3) —C(O)NHR$^1$,
  4) —C(O)N(R$^1$)R$^1$,
  5) —C(O)R$^1$,
  6) —CN,
  7) —SR$^1$,
  8) —S(O)$_2$NH$_2$,
  9) —S(O)$_2$NHR$^1$,
  10) —S(O)$_2$N(R$^1$)R$^1$,
  11) —S(O)R$^1$,
  12) —S(O)$_2$R$^1$,
  13) -L,
  14) -benzyl optionally substituted with 1, 2 or 3 R$^4$ or R$^1$ substituents, 15) -L-heteroaryl optionally substituted with one or more $R^4$ or $R^1$ substituents attached on either or both the L and the heteroaryl groups,
16) -L-heterocyclyl optionally substituted with one or more $R^4$ or $R^1$ substituents attached on either one or both the L and the heterocyclyl groups,
17) -L-aryl optionally substituted with one or more $R^4$ or $R^1$ substituents attached on either or both the L and the heteroaryl groups,
18) -heteroaryl optionally substituted with one or more $R^4$ or $R^1$ substituents, or
19) -aryl optionally substituted with one or more $R^4$ or $R^1$ substituents, and wherein each substituent is optionally attached to the L group if it is not already present,
and wherein, when $(R^1)$ and $R^1$ are attached to a nitrogen atom, optionally they join together with the nitrogen atom to form a 3 to 7-membered ring which optionally includes one or more other heteroatom selected from N, O and S, optionally the is substituted with one or more $R^1$ or $R^4$;

W is
1) —H,
2) -halogen,
3) —$OR^1$,
4) -L-OH,
5) -L-$OR^1$,
6) —$SR^1$,
7) —CN,
8) —P(O)($OR^1$)($OR^1$),
9) —$NHR^1$,
10) —N($R^1$)$R^1$,
11) -L-$NH_2$,
12) -L-$NHR^1$,
13) -L-N($R^1$)$R^1$,
14) -L-$SR^1$,
15) -L-S(O)$R^1$,
16) -L-S(O)$_2R^1$,
17) -L-P(O)($OR^1$)($OR^1$),
18) —C(O)$OR^1$,
19) —C(O)$NH_2$,
20) —C(O)$NHR^1$,
21) —C(O)N($R^1$)$R^1$,
22) —NHC(O)$R^1$,
23) —$NR^1$C(O)$R^1$,
24) —NHC(O)$OR^1$,
25) —$NR^1$C(O)$OR^1$,
26) —OC(O)$NH_2$,
27) —OC(O)$NHR^1$,
28) —OC(O)N($R^1$)$R^1$,
29) —OC(O)$R^1$,
30) —C(O)$R^1$,
31) —NHC(O)$NH_2$,
32) —NHC(O)$NHR^1$,
33) —NHC(O)N($R^1$)$R^1$,
34) —$NR^1$C(O)$NH_2$,
35) —$NR^1$C(O)$NHR^1$,
36) —$NR^1$C(O)N($R^1$)$R^1$,
37) —NHS(O)$_2R^1$,
38) —$NR^1$S(O)$_2R^1$,
39) —S(O)$_2NH_2$,
40) —S(O)$_2NHR^1$,
41) —S(O)$_2$N($R^1$)$R^1$,
42) —S(O)$R^1$,
43) —S(O)$_2R^1$,
44) —OS(O)$_2R^1$,
45) —S(O)$_2OR^1$,
46) -benzyl optionally substituted with 1, 2 or 3 $R^4$ or $R^1$ substituents,
47) -L-heteroaryl optionally substituted with one or more $R^4$ or $R^1$ substituents attached on either or both the L and the heteroaryl groups,
48) -L-heterocyclyl optionally substituted with one or more $R^4$ or $R^1$ substituents attached on either or both the L and the heterocyclyl groups,
49) -L-aryl optionally substituted with one or more $R^4$ or $R^1$ substituents attached on either or both the L and aryl groups,
50) -L-$NR^1(R^1)$,
51) -L-)$_2NR^1$,
52) -L-(N($R^1$)-L)$_n$-N($R^1$)$R^1$,
53) -L-(N($R^1$)-L)$_n$-heteroaryl optionally substituted with one or more $R^4$ or $R^1$ substituents attached on either or both the L and heteroaryl groups,
54) -L-(N($R^1$)-L)$_n$-heterocyclyl optionally substituted with one or more $R^4$ or $R^1$ substituents attached on either or both the L and heterocyclyl groups,
55) -L-(N($R^1$)-L)$_n$-aryl optionally substituted with one or more $R^4$ or $R^1$ substituents attached on either or both the L and aryl groups,
56) —O-L-N($R^1$)$R^1$,
57) —O-L-heteroaryl optionally substituted with one or more $R^4$ or $R^1$ substituents attached on either or both the L and heteroaryl groups,
58) —O-L-heterocyclyl optionally substituted with one or more $R^4$ or $R^1$ substituents attached on either or both the L and heterocyclyl groups,
59) —O-L-aryl optionally substituted with one or more $R^4$ or $R^1$ substituents attached on either or both the L and aryl groups,
60) —O-L)$_2$-$NR^1$,
61) —O-L-(N($R^1$)-L)$_n$-N($R^1$)$R^1$,
62) —O-L-(N($R^1$)-L)$_n$-heteroaryl optionally substituted with one or more $R^4$ or $R^1$ substituents attached on either or both the L and heteroaryl groups,
63) —O-L-(N($R^1$)-L)$_n$-heterocyclyl optionally substituted with one or more $R^4$ or $R^1$ substituents attached on either or both the L and heterocyclyl groups,
64) —O-L-(N($R^1$)-L)$_n$-aryl optionally substituted with one or more $R^4$ or $R^1$ substituents,
65) —S-L-heteroaryl optionally substituted with one or more $R^4$ or $R^1$ substituents,
66) —S-L-heterocyclyl optionally substituted with one or more $R^4$ or $R^1$ substituents,
67) —S-L-aryl optionally substituted with one or more $R^4$ or $R^1$ substituents attached on either or both the L and aryl groups,
68) —S-L)$_2NR^1$,
69) —S-L-(N($R^1$)-L)$_n$-N($R^1$)$R^1$,
70) —S-L-(N($R^1$)-L)$_n$-heteroaryl optionally substituted with one or more $R^4$ substituents,
71) —S-L-(N($R^1$)-L)$_n$-heterocyclyl optionally substituted with one or more $R^4$ substituents,
72) —S-L-(N($R^1$)-L)$_n$-aryl optionally substituted with one or more $R^4$ substituents,
73) —$NR^1(R^1)$,
74) —(N($R^1$)-L)$_n$-N($R^1$)$R^1$,
75) —N($R^1$)L)$_2$-$NR^1$,
76) —(N($R^1$)-L)$_n$-N($R^1$)$R^4$,
77) —(N($R^1$)-L)$_n$-heteroaryl optionally substituted with one or more $R^4$ or $R^1$ substituents,
78) —(N($R^1$)-L)$_n$-heterocyclyl optionally substituted with one or more $R^4$ or $R^1$ substituents, 79) —(N(R$^1$)-L)$_n$-aryl optionally substituted with one or more R$^4$ or R$^1$ substituents,
80) -heteroaryl optionally substituted with one or more R$^4$ substituents, or
81) -aryl optionally substituted with one or more R$^4$ substituents, and wherein each substituent is optionally attached to the L group if it is not already present, and wherein when two R$^1$ substituents are present on the same nitrogen atom, then each R$^1$ substituent is independently selected from the list of R$^1$ values described thereafter, and wherein n is an integer equal to either 0, 1, 2, 3, 4, or 5, and wherein, when (R$^1$) and R$^1$ are attached to a nitrogen atom, optionally they join together with the nitrogen atom to form a 3 to 7-membered ring which optionally includes one or more other heteroatom selected from N, O and S, optionally the ring is substituted with one or more R$^1$ or R$^4$;

L is
1) —C$_{1-6}$ alkyl,
2) —C$_{2-6}$ alkenyl,
3) —C$_{2-6}$ alkynyl,
4) —C$_{3-7}$ cycloalkyl,
5) —C$_{3-7}$ cycloalkenyl,
6) heterocyclyl,
7) —C$_{1-6}$ alkyl-C$_{3-7}$ cycloalkyl,
8) —C$_{1-6}$ alkyl-heterocyclyl,
9) aryl, or
10) heteroaryl, and wherein the alkyl, the alkenyl, the alkynyl, the cycloalkyl, the cycloalkenyl, the heterocyclyl, the aryl and the heteroaryl groups are each independently optionally substituted with one or two R$^4$ substituent;

R$^1$ is
1) —H,
2) —C$_{1-6}$ alkyl,
3) —C$_{2-6}$ alkenyl,
4) —C$_{2-6}$ alkynyl,
5) —C$_{3-7}$ cycloalkyl,
6) —C$_{3-7}$ cycloalkenyl,
7) —C$_{1-6}$ perfluorinated,
8) -heterocyclyl,
9) -aryl,
10) -heteroaryl,
11) -benzyl, or
12) 5-[(3aS,4S,6aR)-2-oxohexahydro-1H-thieno[3,4-d]imidazol-4-yl]pentanoyl, and wherein the alkyl, the alkenyl, the alkynyl, the cycloalkenyl, the perfluorinated alkyl, the heterocyclyl, the aryl, the heteroaryl and the benzyl groups are each independently optionally substituted with 1, 2 or 3 R$^4$ or R$^1$ substituents;

R$^2$ is
1) —H,
2) —C$_{1-6}$ alkyl,
3) —SR$^1$,
4) —C(O)R$^1$,
5) —S(O)R$^1$,
6) —S(O)$_2$R$^1$,
7) -benzyl optionally substituted with 1, 2 or 3 R$^4$ or R$^1$ substituents,
8) -L-heteroaryl optionally substituted with one or more R$^4$ or R$^1$ substituents attached on either one or both the L and the heteroaryl groups,
9) -L-heterocyclyl optionally substituted with one or more R$^4$ or R$^1$ substituents attached on either one or both the L and the heterocyclyl groups,
10) -L-aryl optionally substituted with one or more R$^4$ or R$^1$ substituents attached on either one or both the L and the aryl groups,
11) -heteroaryl optionally substituted with one or more R$^4$ or R$^1$ substituents, or
12) -aryl optionally substituted with one or more R$^4$ or R$^1$ substituents, and wherein each substituent is optionally attached to the L group if it is not already present;

R$^4$ is
1) -halogen,
2) —CF$_3$,
3) —OH,
4) —OR$^1$,
5) -L-OH,
6) -L-OR$^1$,
7) —OCF$_3$,
8) —SH,
9) —SR$^1$,
10) —CN,
11) —NO$_2$,
12) —NH$_2$,
13) —NHR$^1$,
14) —NR$^1$R$^1$,
15) -L-NH$_2$,
16) -L-NHR$^1$,
17) -L-NR$^4$R$^1$,
18) -L-SR$^1$,
19) -L-S(O)R$^1$,
20) -L-S(O)$_2$R$^1$,
21) —C(O)OH,
22) —C(O)OR$^1$,
23) —C(O)NH$_2$,
24) —C(O)NHR$^1$,
25) —C(O)N(R$^1$)R$^1$,
26) —NHC(O)R$^1$,
27) —NR$^1$C(O)R$^1$,
28) —NHC(O)OR$^1$,
29) —NR$^1$C(O)OR$^1$,
30) —OC(O)NH$_2$,
31) —OC(O)NHR$^1$,
32) —OC(O)N(R$^1$)R$^1$,
33) —OC(O)R$^1$,
34) —C(O)R$^1$,
35) —NHC(O)NH$_2$,
36) —NHC(O)NHR$^1$,
37) —NHC(O)N(R$^1$)R$^1$,
38) —NR$^1$C(O)NH$_2$,
39) —NR$^1$C(O)NHR$^1$,
40) —NR$^1$C(O)N(R$^1$)R$^1$,
41) —NHS(O)$_2$R$^1$,
42) —NR$^1$S(O)$_2$R$^1$,
43) —S(O)$_2$NH$_2$,
44) —S(O)$_2$NHR$^1$,
45) —S(O)$_2$N(R$^1$)R$^1$,
46) —S(O)R$^1$,
47) —S(O)$_2$R$^1$,
48) —OS(O)$_2$R$^1$,
49) —S(O)$_2$OR$^1$,
50) -benzyl,
51) —N$_3$, or
52) —C(—N=N—)(CF$_3$), and wherein the benzyl group is optionally substituted with 1, 2 or 3 R$^4$ or R$^1$ substituents.

In an embodiment, the compound of item (b) above is a compound of general formula III or IV:

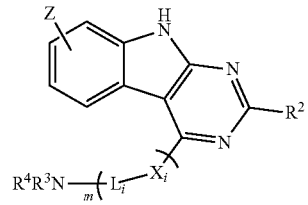

III

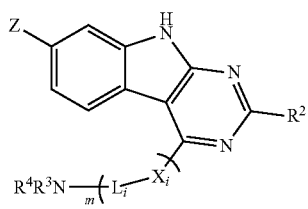

IV or a salt or a prodrug thereof, wherein Z and $R^2$ are each as defined above, and m is an integer from 1 to 6, and wherein when m is 2 or more, $X_i$ are the same or different and are each independently $NR^1$, $CH_2$, O or S, wherein $R^1$ is as defined above, and $L_i$ are the same or different and are each independently L as defined above, and wherein $R^3$ and $R^4$ are the same or different and are each independently H, $R^1$ as defined in claim 1, or they join together with N to form a 3 to 7-membered ring which optionally includes one or more other heteroatom selected from N, O and S, optionally the ring is substituted with one or more $R^1$ or $R^4$.

In an embodiment, the compound of item (b) above is a compound of general formula V or VI:

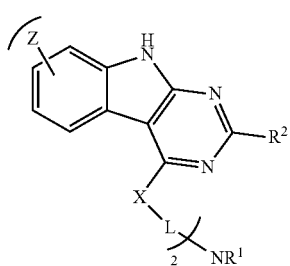

V

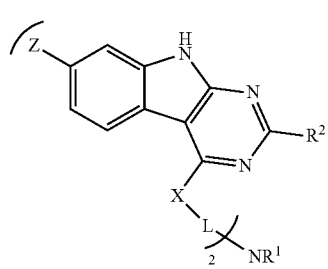

VI or a salt or a prodrug thereof, wherein Z, L, $R^1$ and $R^2$ are each as defined above.

In an embodiment, the compound of item (b) above is a compound of general formula IIA:

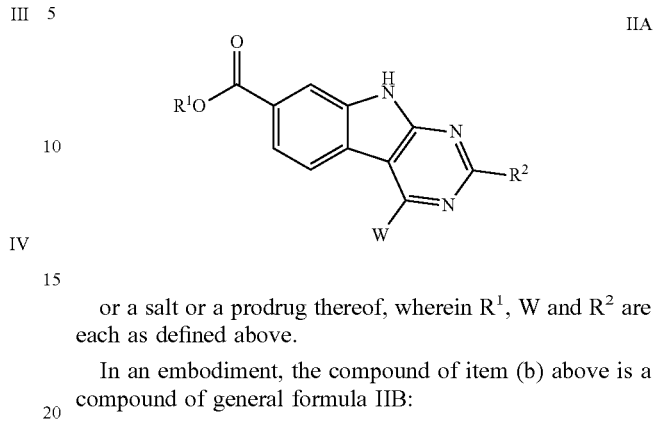

IIA or a salt or a prodrug thereof, wherein $R^1$, W and $R^2$ are each as defined above.

In an embodiment, the compound of item (b) above is a compound of general formula IIB:

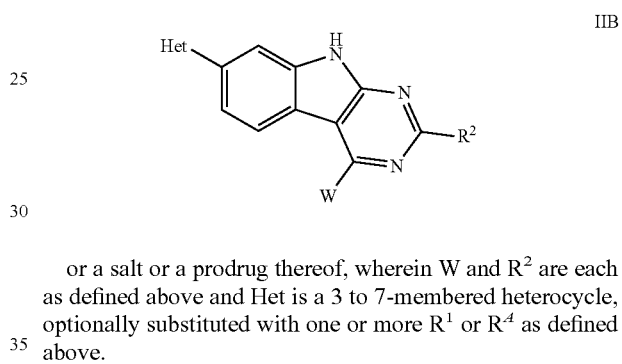

IIB or a salt or a prodrug thereof, wherein W and $R^2$ are each as defined above and Het is a 3 to 7-membered heterocycle, optionally substituted with one or more $R^1$ or $R^4$ as defined above.

In an embodiment, the compound of item (b) above is a compound of general formula IIC:

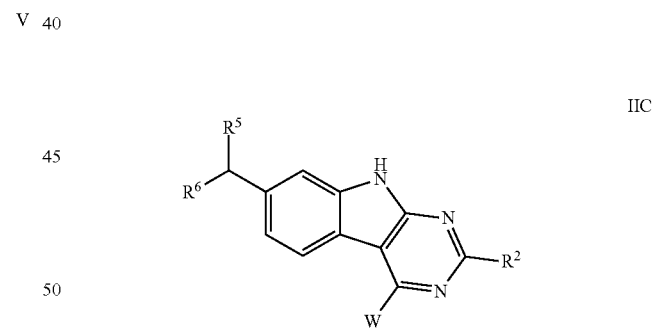

IIC or a salt or a prodrug thereof, wherein W and $R^2$ are each as defined above and wherein $R^5$ and $R^6$ are the same or different and are each independently L as defined above, or they join together with C to form a 5 to 7-membered ring which optionally includes one or more heteroatom selected from N, O and S, optionally the ring is substituted with one or more $R^1$ or $R^4$. In an embodiment, the ring is a 5-membered ring, and the heteroatom is N. In a further embodiment, the ring includes four N. In an embodiment, $R^2$ is benzyl.

In an embodiment, the compound of item (b) above is a compound of general formula IVA

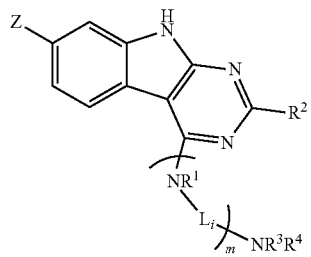

IVA or a salt or a prodrug thereof, wherein W, L, $R^1$, $R^2$, m, $L^1$, $R^3$ and $R^4$ are each as defined above.

In a further embodiment, Z is $CO_2Me$ or 2-methyl-2H-tetrazol-5-yl; $R^2$ is benzyl, 3-thienylmethyl or 3-pyridinyl methyl; and W is NH-L-N($R^1$)$R^1$ wherein L is $C_{2-4}$ alkyl and $R^1$ is $C_{1-4}$ alkyl or ($R^1$) and $R^1$ join together with the nitrogen atom to which they are attached to form a 3 to 7-membered ring, which optionally includes one or more other heteroatom selected from N, O and S, optionally the ring is substituted with one or more $R^1$ or $R^4$.

In an embodiment, the compound of item (b) above is any of compounds 1 to 55 depicted below, or a salt or a prodrug thereof.

| Compound number | Structure |
|---|---|
| 1 | 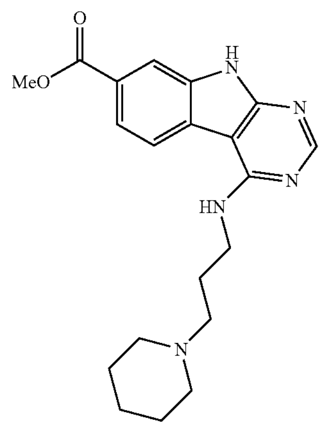 [SMILES: COC(=O)c1ccc2c(c1)[nH]c1ncnc(NCCCN3CCCCC3)c12] |
| 2 | 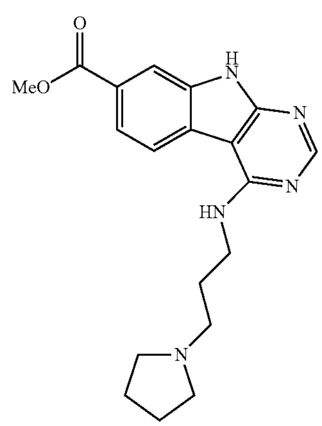 [SMILES: COC(=O)c1ccc2c(c1)[nH]c1ncnc(NCCCN3CCCC3)c12] |

-continued
| Compound number | Structure |
|---|---|
| 3 | 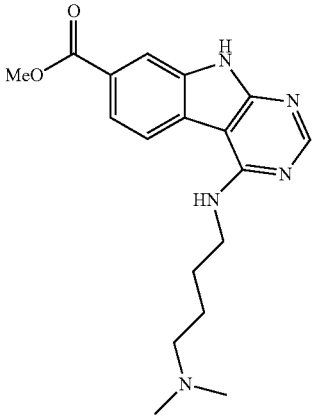 [SMILES: COC(=O)c1ccc2c(c1)[nH]c1ncnc(NCCCCN(C)C)c12] |
| 4 | 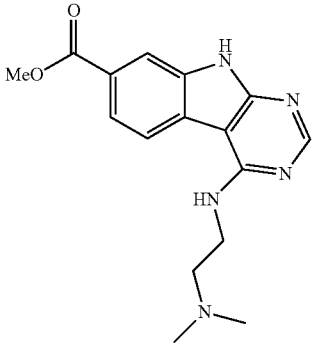 [SMILES: COC(=O)c1ccc2c(c1)[nH]c1ncnc(NCCN(C)C)c12] |
| 5 | 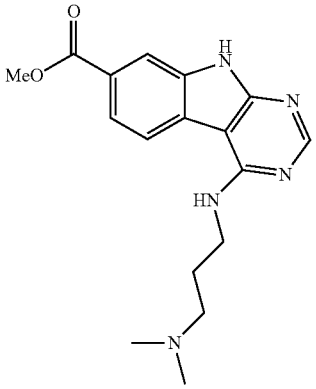 [SMILES: COC(=O)c1ccc2c(c1)[nH]c1ncnc(NCCCN(C)C)c12] |
| 6 | 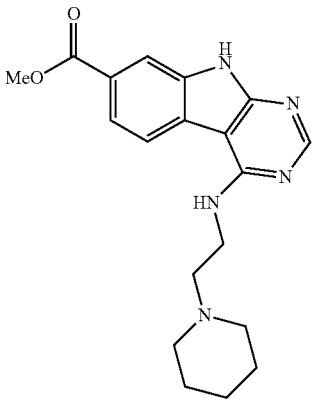 [SMILES: COC(=O)c1ccc2c(c1)[nH]c1ncnc(NCCN3CCCCC3)c12] |

-continued
| Compound number | Structure |
|---|---|
| 7 | 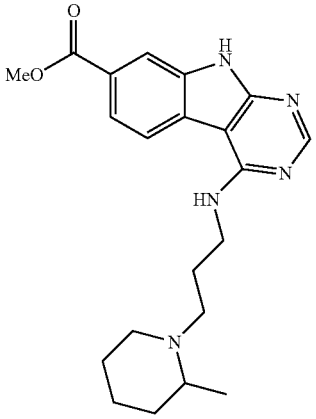 [SMILES: COC(=O)c1ccc2c(c1)[nH]c1ncnc(NCCCN3CCCCC3C)c12] |
| 8 | 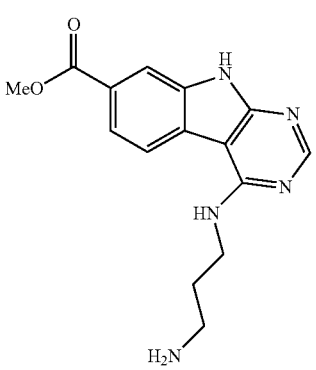 [SMILES: COC(=O)c1ccc2c(c1)[nH]c1ncnc(NCCCN)c12] |
| 9 | 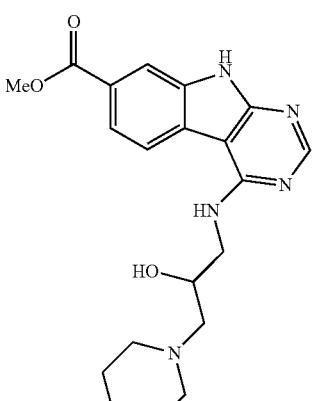 |
| 10 | 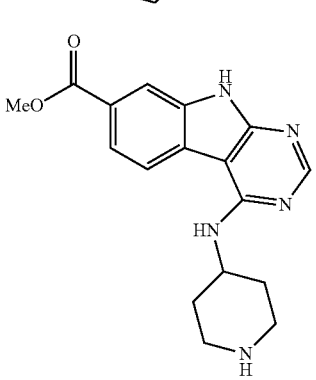 |

-continued
| Compound number | Structure |
|---|---|
| 11 | 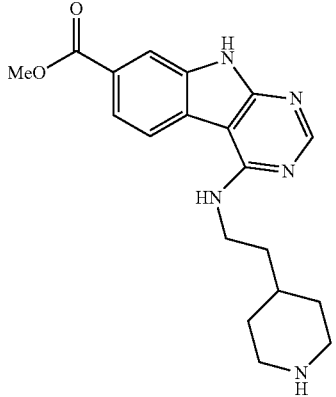 [SMILES: COC(=O)c1ccc2c(c1)[nH]c1ncnc(NCCC3CCNCC3)c12] |
| 12 | 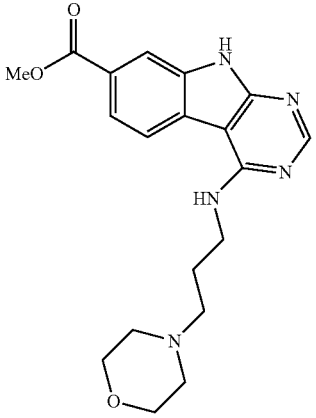 [SMILES: COC(=O)c1ccc2c(c1)[nH]c1ncnc(NCCCN3CCOCC3)c12] |
| 13 | 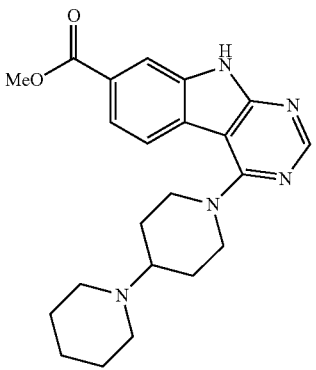 [SMILES: COC(=O)c1ccc2c(c1)[nH]c1ncnc(N3CCC(N4CCCCC4)CC3)c12] |

| Compound number | Structure |
|---|---|
| 14 | *(structure: 2-methyltetrazolyl-substituted pyrimido-indole with HN-(CH2)3-piperidine)* |
| 15 | *(structure: MeO2C-substituted pyrimido-indole with 3-pyridylmethyl and HN-(CH2)3-piperidine)* |
| 16 | *(structure: MeO2C-substituted pyrimido-indole with 4-pyridylmethyl and HN-(CH2)3-piperidine)* |
| 17 | *(structure: MeO2C-substituted pyrimido-indole with pyrazin-2-ylmethyl and HN-(CH2)3-piperidine)* |

-continued

| Compound number | Structure |
| --- | --- |
| 18 | (structure: methyl carboxylate-substituted pyrimido-indole with thiophen-3-ylmethyl group and HN-CH2CH2CH2-piperidine substituent) |
| 19 | (structure: methyl carboxylate-substituted pyrimido-indole with 3-bromo-5-iodobenzyl group and HN-CH2CH2CH2-piperidine substituent; TFA salt) |
| 20 | (structure: methyl carboxylate-substituted pyrimido-indole with naphthalen-2-ylmethyl group and HN-CH2CH2CH2-piperidine substituent; TFA salt) |
| 21 | (structure: methyl carboxylate-substituted pyrimido-indole with phenyl(methoxy)methyl group and HN-CH2CH2CH2-piperidine substituent) |
| 22 | (structure: methyl carboxylate-substituted pyrimido-indole with phenyl(hydroxy)methyl group and HN-CH2CH2CH2-piperidine substituent) |

| Compound number | Structure |
|---|---|
| 23 | 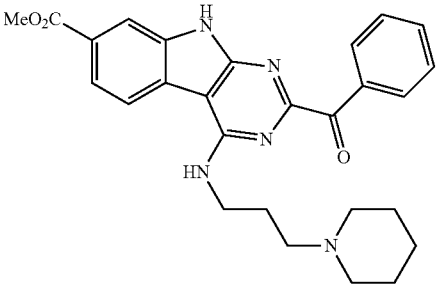 [SMILES: COC(=O)c1ccc2c(c1)[nH]c1nc(C(=O)c3ccccc3)nc(NCCCN3CCCCC3)c12] |
| 24 | 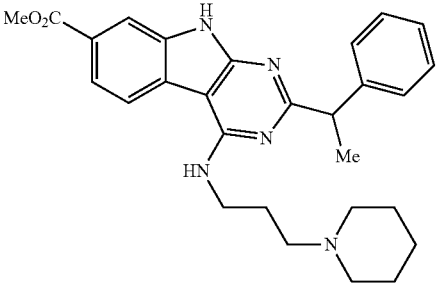 [SMILES: COC(=O)c1ccc2c(c1)[nH]c1nc(C(C)c3ccccc3)nc(NCCCN3CCCCC3)c12] |
| 25 | 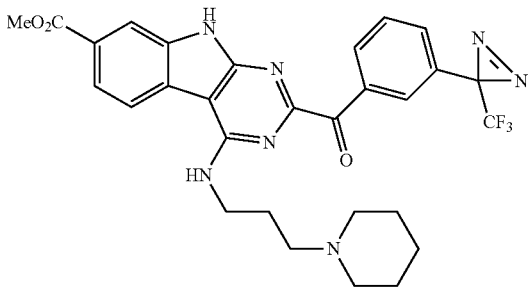 [SMILES: COC(=O)c1ccc2c(c1)[nH]c1nc(C(=O)c3cccc(C4(C(F)(F)F)N=N4)c3)nc(NCCCN3CCCCC3)c12] |
| 26 | 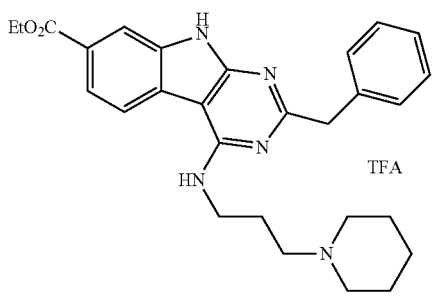 [SMILES: CCOC(=O)c1ccc2c(c1)[nH]c1nc(Cc3ccccc3)nc(NCCCN3CCCCC3)c12] |
| 27 | 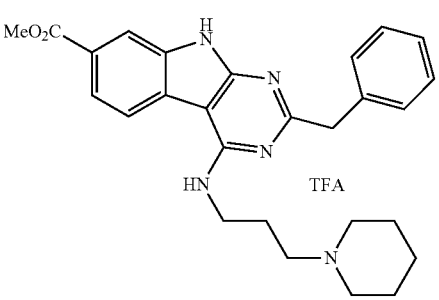 [SMILES: COC(=O)c1ccc2c(c1)[nH]c1nc(Cc3ccccc3)nc(NCCCN3CCCCC3)c12] |

-continued
| Compound number | Structure |
|---|---|
| 28 | 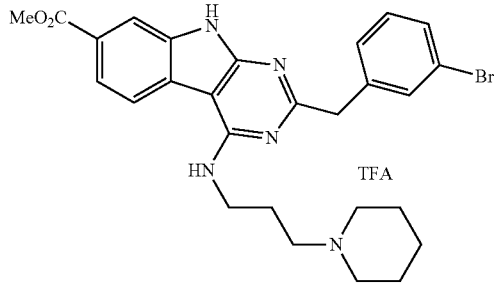 TFA |
| 29 | 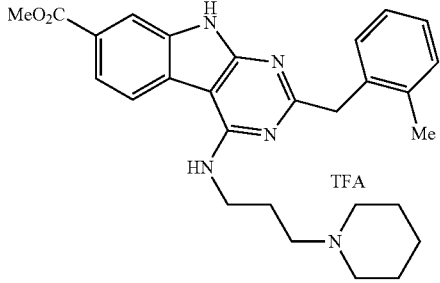 TFA |
| 30 | 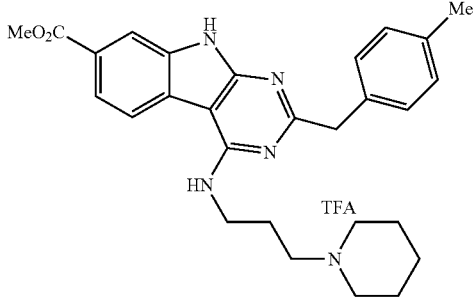 TFA |
| 31 | 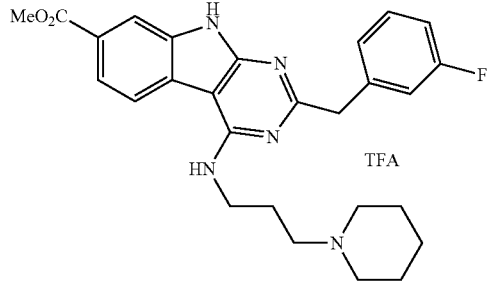 TFA |
| 32 | 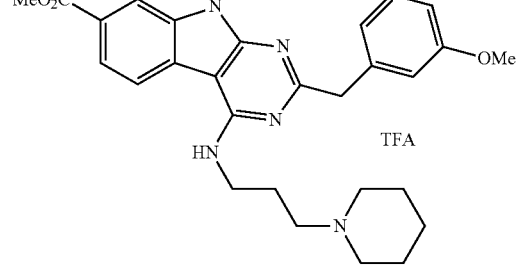 TFA |

-continued

| Compound number | Structure |
|---|---|
| 33 | (structure) |
| 34 | (structure) |
| 35 | (structure) |
| 36 | (structure) |
| 37 | (structure) |

-continued
| Compound number | Structure |
|---|---|
| 38 | 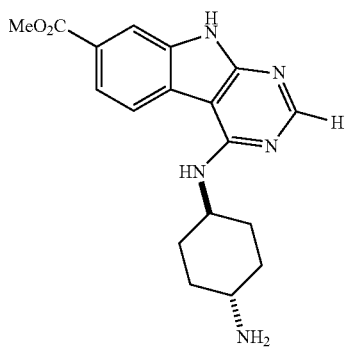 |
| 39 | 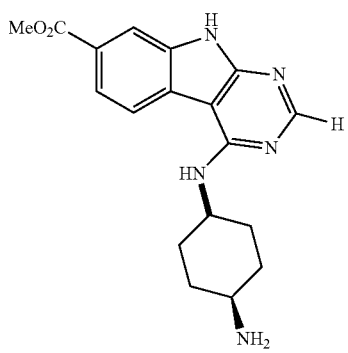 |
| 40 | 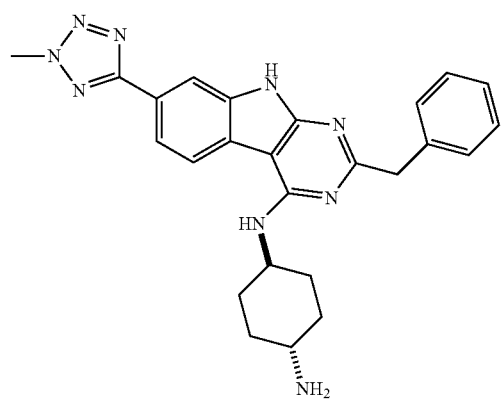 |
| 41 | 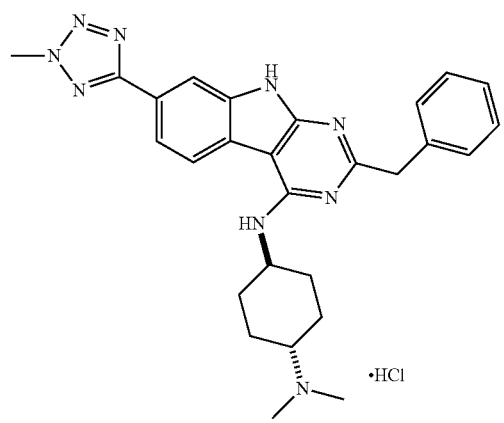 |

-continued

| Compound number | Structure |
|---|---|
| 42 | (structure) |
| 43 | (structure) |
| 44 | (structure) |
| 45 | (structure) |
| 46 | (structure) |

-continued

| Compound number | Structure |
| --- | --- |
| 47 | (structure) |
| 48 | (structure) |
| 49 | (structure) |
| 50 | (structure) |
| 51 | (structure) |

-continued

| Compound number | Structure |
|---|---|
| 52 | (structure) |
| 53 | (structure) |
| 54 | (structure) |
| 55 | (structure) |

In an embodiment, the compound of item (b) above is compound 1:

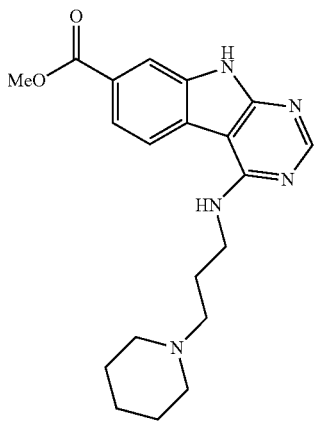 [SMILES: COC(=O)c1ccc2c(c1)[nH]c1ncnc(NCCCN3CCCCC3)c12]

or a salt or a prodrug thereof.

In an embodiment, the method comprises contacting said cells with a compound of Table 1 below.

In another aspect, the present invention provides a method for (i) inhibiting or preventing the differentiation, and/or (ii) promoting the expansion or maintenance, of acute myeloid leukemia (AML) initiating cells ex vivo, said method comprising contacting said cells with a suppressor of the Aryl hydrocarbon Receptor (AhR) and/or with a compound of general formula I-VI, IIA-IIC, IVA, VIA, or any of compounds 1 to 55 as defined above. In an embodiment, the method comprises contacting said cells with a compound of Table 1 below.

In a specific embodiment, the methods comprise contacting said cells with (a) a suppressor of AhR and (b) a compound of general formula I-VI, IIA-IIC, IVA, VIA, or any of compounds 1 to 55 as defined above. In a further embodiment, the compound (b) is compound 1 or a salt or a prodrug thereof. In another specific embodiment, said suppressor of AhR is StemRegenin 1 (SR1), retusin-7-methylether (C01), UM0125464 (C02), chrysin (C04), kaempferide (C06), xanthone, 3-chloro-N-(2,3-dihydro-1,4-benzodioxin-6-yl)-1-benzithiophene-2-carboxamide (C03), 5-methoxyflavone (C08), or N-methyl-β-carboline-3-carboxamide (C05). In another specific embodiment, said suppressor of AhR is StemRegenin 1 (SR1), retusin-7-methylether (C01), UM0125464 (C02), 3-chloro-N-(2,3-dihydro-1,4-benzodioxin-6-yl)-1-benzithiophene-2-carboxamide (C03), chrysin (C04), kaempferide (C06), 5-methoxyflavone (C08), or N-methyl-β-carboline-3-carboxamide (C05). In another specific embodiment, said suppressor of AhR is N-methyl-β-carboline-3-carboxamide.

In another specific embodiment, the method comprises (a) providing a cell population comprising said AML initiating cells and (b) culturing said cell population ex vivo under suitable conditions for expanding or maintaining undifferentiated primary AML blasts.

In another aspect, the present invention provides an enriched AML initiating cell population. In another aspect, the present invention provides an ex vivo culture comprising an AML initiating cell population. In a specific embodiment, the cell population is obtained by the method of the present invention as described herein. In an embodiment, the enriched AML initiating cell population has been maintained in culture for at least 1, 2, 4, 8, 12, 18 or 24 h. In other embodiments, the enriched AML initiating cell population has been maintained in culture for at least 2, 3, 4, 5, 6 or 7 days. In an embodiment, the number of AML initiating cells in said population is at least 5-fold higher relative to the number of AML initiating cells in a corresponding population cultured in the absence of the compounds of items (a) and/or (b) defined above. In further embodiments, the number of AML initiating cells in said population is at least 10-, 15, 20-, 25-, 30-, 40- or 50-fold higher relative to the number of AML initiating cells in a corresponding population cultured in the absence of the compounds of items (a) and/or (b) defined above In another aspect, the present invention provides method for determining whether a test agent may be useful for inhibiting and/or eliminating AML initiating cells, said method comprising (a) culturing a cell population comprising AML initiating cells in the presence of a suppressor of the Aryl hydrocarbon Receptor (AhR) and/or general formula I-VI, IIA-IIC, IVA, VIA, or any of compounds 1 to 55 as defined above and (b) contacting said cell population with said test agent; and (c) determining whether undifferentiated primary AML blasts are inhibited and/or eliminated in the presence of the test agent. In an embodiment, the method comprises culturing said cells in the presence of a compound of Table 1 below.

In a specific embodiment, step (c) comprises comparing the number of undifferentiated primary AML blasts in the culture in the presence and absence of said test agent, wherein a lower number of undifferentiated primary AML blasts in the presence of said test agent is indicative that said test agent may be useful for inhibiting and/or eliminating AML initiating cells.

In another aspect, the present invention provides a method for (i) stimulating the differentiation, and/or (ii) inhibiting the expansion or maintenance, of acute myeloid leukemia (AML) initiating cells ex vivo, said method comprising culturing said cells in the presence of an agonist of the Aryl hydrocarbon Receptor (AhR).

In another aspect, the present invention provides a method for inhibiting or eliminating AML initiating cells in a subject, said method comprising administering to said subject an effective amount of a pharmaceutically acceptable agonist of the Aryl hydrocarbon Receptor (AhR).

In another aspect, the present invention provides a method for preventing or inhibiting minimal residual disease (MRD) in an AML patient, said method comprising administering to said patient an effective amount of a pharmaceutically acceptable suppressor of the Aryl hydrocarbon Receptor (AhR).

In a specific embodiment, the method further comprises administering a chemotherapeutic agent to the subject.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 4C shows representative FACS plots of patient cells recovered from recipient NSG mice 16 weeks after transplantation of 2×10$^6$ uncultured cells (left), or equivalent cell numbers harvested from 4-day cultures containing DMSO or SR1 (500 nM). Non transplanted patient cells (05H163) are also shown (lower right). Numbers indicate percentages within total mouse bone marrow, numbers in brackets represent fractions of human CD45$^+$ cells;

FIG. 4D shows the estimated LSC frequencies and 95% confidence intervals (CI) for 6 AML specimens in FIG. 4B. When all or none of the recipients were engrafted, one-sided CI were calculated and are indicated by arrows. Differences between conditions were analyzed by Chi-square test (Hu, Y, and Smyth, G K (2009). ELDA: Extreme limiting dilution analysis for comparing depleted and enriched populations in stem cell and other assays. *Journal of Immunological Methods* 347, 70-78; http://bioinf.wehi.edu.au/software/elda/), *P<0.05 **P<0.005, differences between DMSO and fresh cells are significant (P<0.0005) for all samples;

FIG. 6 shows the chemical structure of compounds C01-004, C06 and C08 confirmed in secondary screenings. The structure of compounds C05 and C07 is depicted in FIG. 1F;

FIG. 7A shows the fold changes of CYP1B1 expression compared to fresh cells after 24 h (grey bars) or 6 days (black bars) in control culture conditions (DMSO);

FIG. 7B shows AhR target gene induction after 24 h incubation in serum-free culture medium in absence and presence of vehicle DMSO (0.1%) compared to $t_0$ (Left panel). The right panel shows AhR target gene induction after 24 h incubation in cultures containing DMSO or SR1 (500 nM), in phenol red free medium and in phenol red free medium without antibiotics (AB) compared to $t_0$;

FIG. 14A depicts the amino acid sequence of a human AhR polypeptide precursor (NCBI Reference Sequence: NP_001612.1, SEQ ID NO:2). The mature form comprises residues 11-848 (residues 1-10 correspond to a propeptide);

FIGS. 14B and 14C depict the nucleotide sequence of a human AhR mRNA (NCBI Reference Sequence: NM_001621.4, coding sequence 614-3160, SEQ ID NO:1);

FIGS. 15A, 15B and 15C show the patient and specimen information for the studies described herein;

FIGS. 16A and 16B show LSC frequencies and engraftment levels measured in the experiments described in Example 6.

DETAILED DESCRIPTION OF INVENTION

Figure 1A:
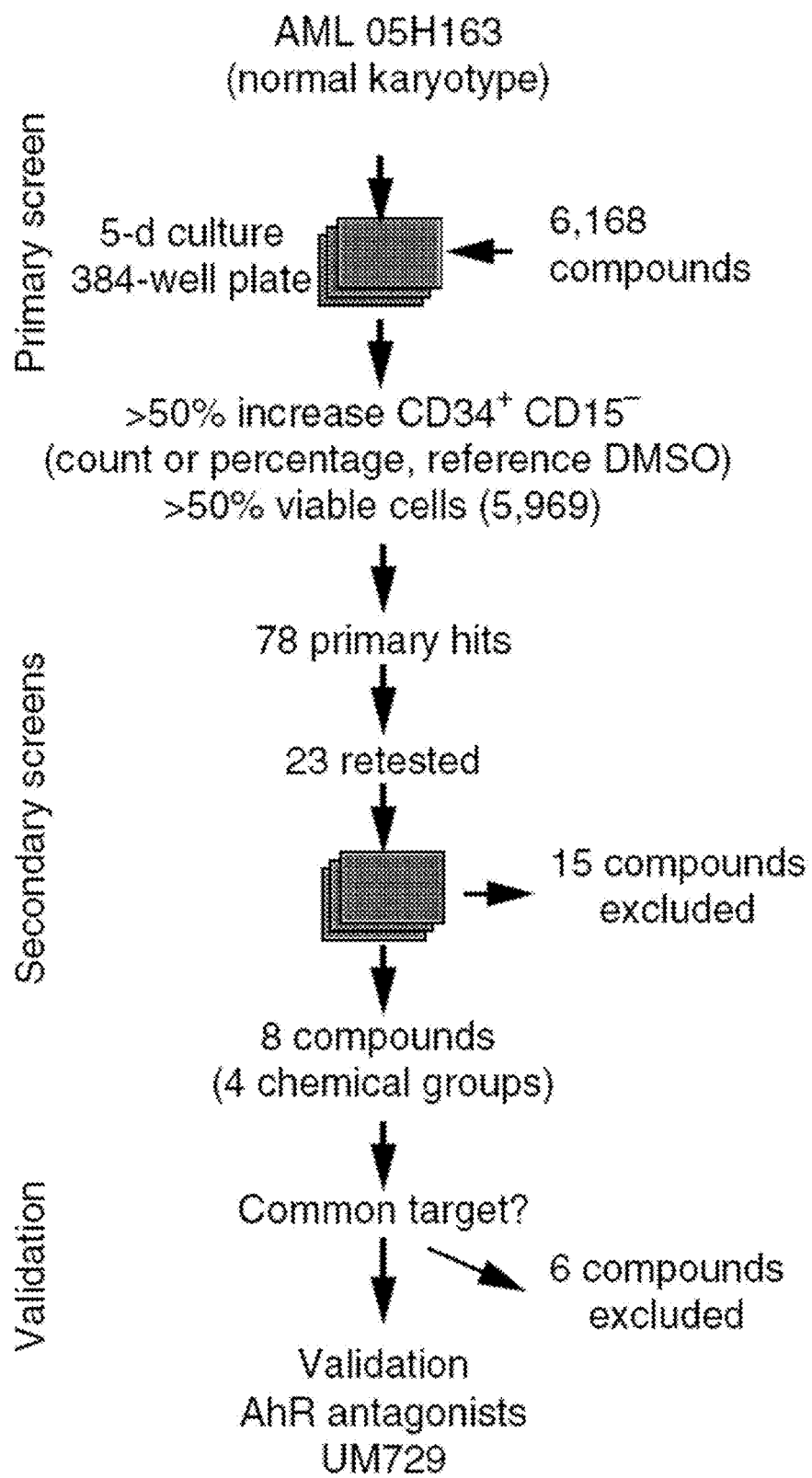
FIG. 1A is an overview of the strategy used for the screening of modulators of the differentiation of primary human AML cells. 6,168 compounds were tested on a cytogenetically normal AML for their ability to prevent differentiation of primary human AML cells in vitro. Loss of CD34 and acquisition of CD15 surface expression measured by HTS-flow cytometry were used as indication of differentiation. 78 compounds complying with indicated viability criteria yielded >50% increase of CD34$^+$CD15$^-$ (%) compared to control (DMSO). Of these, 23 compounds were retested in secondary screenings, and 8 compounds were selected for validation. After excluding compounds with common target and negative impact on cell proliferation, 2 compounds were selected for validation.

In the studies described herein, the present inventors have shown that contacting a cell population comprising primary human AML cells with a suppressor of the Aryl hydrocarbon Receptor (AhR) and/or with a compound of general formula I-VI, IIA-IIC, IVA, VIA, or any of compounds 1 to 55 as defined herein allows expansion of phenotypically and morphologically undifferentiated primary human AML blasts and partially rescues AML initiating activity in vitro (e.g., in vitro).

Accordingly, in a first aspect, the present invention provides a method for (i) inhibiting or preventing the differentiation of acute myeloid leukemia (AML) initiating cells ex vivo; and/or (ii) promoting the expansion or maintenance of undifferentiated primary AML blasts ex vivo; and/or (iii) partially rescuing (i.e., near maintaining) AML initiating activity ex vivo, said method comprising contacting said cells with a suppressor of the Aryl hydrocarbon Receptor (AhR) and/or with a compound of general formula I-VI, IIA-IIC, IVA, VIA, or any of compounds 1 to 55 as defined above.

In another aspect, the present invention provides a method for (i) inhibiting or preventing the differentiation, and/or (ii) promoting the expansion or maintenance, of acute myeloid leukemia (AML) initiating cells ex vivo, said method comprising contacting said cells with a compound set forth in Table 1 below.

In another aspect, the present invention provides a method for (i) inhibiting or preventing the differentiation, and/or (ii) promoting the expansion or maintenance, of acute myeloid leukemia (AML) initiating cells ex vivo, said method comprising contacting said cells with a suppressor of the Aryl hydrocarbon Receptor (AhR) and/or with a compound of general formula I-VI, IIA-IIC, IVA, VIA, or any of compounds 1 to 55 as defined above.

In another aspect, the present invention provides a method for (i) inhibiting or preventing the differentiation, and/or (ii) promoting the expansion or maintenance, of acute myeloid leukemia (AML) initiating cells ex vivo, said method comprising contacting said cells with a compound set forth in Table 1 below.

The term "AML initiating cells" (or "AML stem/progenitor cells") refers to cells having the potential to self-renew and to engraft immunocompromised mice (e.g., to reconstitute a phenotypic and functional leukemic cell hierarchy), and are enriched in the CD34$^+$ compartment. LIC-activity also exists however in the CD34$^-$ compartment. Ongoing differentiation in general including ongoing LIC differentiation is characterized by loss of CD34 expression and increased CD15 expression.

AhR (Aryl Hydrocarbon Receptor) is a member of the bHLH (basic Helix-Loop-Helix)-PAS (Per-ARNT-Sim) family of transcriptional regulators that control a variety of developmental and physiological events, including Neurogenesis, Tracheal and Salivary duct formation, Toxin metabolism, Circadian rhythms, response to Hypoxia and Hormone Receptor function. The unique feature of all bHLH-PAS proteins is the PAS domain, named after the first three proteins identified with this motif, the *Drosophila* Per, Human ARNT and *Drosophila* Sim. The PAS domain consists of 260-310 amino acids and incorporates two well-conserved hydrophobic repeats, termed PAS-A (or PAS-1) and PAS-B (or PAS-2), separated by a poorly conserved spacer. Overall, the PAS domain is not well conserved and can mediate a number of diverse biochemical functions. In human Ahr, the bHLH domain spans residues 27-80, the PAS-1 domain spans residues 111-181, the PAS-2 domain spans residues 275-342 and the PAC domain spans residues 348-386. The amino acid sequence of a human AhR polypeptide precursor (NCBI Reference Sequence: NP_001612.1) is depicted in FIG. 14A (SEQ ID NO:2), and the corresponding cDNA sequence (NM_001621.4) is depicted in FIGS. 14B and 14C (SEQ ID NO:1).

AHR, also known as the Dioxin receptor, is recognized as the culprit for most toxic responses observed after exposure to PAH (Polycyclic Aromatic Hydrocarbons), Dioxins (e.g., TCDD (2,3,7,8-tetrachlorodibenzo-p-dioxin)), and Polychlorinated Biphenyls. Ligands for AHR are diverse which include dietary compounds, natural and synthetic flavonoids, natural products, and pharmaceuticals.

AhR suppressors (e.g., inhibitors/antagonists) are well known in the art. The term AhR suppressor includes any compound able to negatively affect the activity of AhR by reducing for example its expression (i.e., at the transcriptional and/or translational level), the level of AhR mRNA and/or protein, or an activity associated with AhR. It includes intracellular as well as extracellular suppressors. Without being so limited, such suppressors include RNA interference agents (e.g., siRNA, shRNA, miRNA and the like), antisense molecules, ribozymes, proteins (e.g., dominant negative, inactive variants), peptides, small molecules, antibodies, antibody fragments, etc.

AhR Antibodies

In an embodiment, the AhR suppressor (e.g., inhibitor/antagonist) is a neutralizing antibody directed against (or specifically binding to) a human AhR polypeptide. The term "antibody" or "immunoglobulin" is used in the broadest sense, and covers monoclonal antibodies (including full-length monoclonal antibodies), polyclonal antibodies, humanized antibodies, CDR-grafted antibodies, chimeric antibodies, multispecific antibodies, and antibody fragments so long as they exhibit the desired biological activity (e.g., neutralizing an activity of the AhR polypeptide). Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, $V_H$ regions ($V_H$, $V_H$-$V_H$), anticalins, PepBodies, antibody-T-cell epitope fusions (Troybodies) or Peptibodies. In an embodiment, the antibody is a monoclonal antibody. In another embodiment, the antibody is a humanized or CDR-grafted antibody.

In general, techniques for preparing antibodies (including monoclonal antibodies and hybridomas) and for detecting antigens using antibodies are well known in the art (Campbell, 1984, In "Monoclonal Antibody Technology Laboratory Techniques in Biochemistry and Molecular Biology", Elsevier Science Publisher, Amsterdam, The Netherlands) and in Harlow et al., 1988 (in: Antibody A Laboratory Manual, CSH Laboratories).

Polyclonal antibodies are preferably raised in animals by multiple subcutaneous (s.c.), intravenous (i.v.) or intraperitoneal (i.p.) injections of the relevant antigen (e.g., an AhR polypeptide, or a fragment thereof) with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N$=C=NR, where R and $R^1$ are different alkyl groups.

Animals may be immunized against the antigen (AhR polypeptide or a fragment thereof), immunogenic conjugates, or derivatives by combining the antigen or conjugate (e.g., 100 µg for rabbits or 5 µg for mice) with 3 volumes of Freund's complete adjuvant and injecting the solution intradermally at multiple sites. One month later the animals are boosted with the antigen or conjugate (e.g., with ⅕ to ⅒ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., *Nature,* 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

A human chimeric antibody can be produced in the following manner. cDNA encoding heavy chain variable region (VH) and light chain variable region (VL) obtained from a hybridoma derived from non-human animal cells producing monoclonal antibodies, the cDNA is inserted to each of expression vectors for animal cells having DNA encoding a heavy chain constant region (CH) and light chain constant region (CL) of a human antibody so as to construct a human chimeric antibody expression vector, and this vector is introduced to animal cells to express the human chimeric antibody.

A humanized antibody refers to an antibody which is obtained by grafting the amino acid sequence of the complementary determining region (CDR) of VH and VL of a non-human animal antibody to CDR corresponding to VH and VL of a human antibody. The region other than CDR of VH and VL is called a framework region (hereinbelow, described as "FR"). A humanized antibody can be produced in the following manner. cDNA encoding an amino acid sequence of VH which consists of an amino acid sequence of CDR of VH of a non-human antibody and an amino acid sequence of FR of VH of any human antibody, and cDNA encoding an amino acid sequence of VL which consists of an amino acid sequence of CDR of VL of a non-human animal antibody and an amino acid sequence of FR of VL of any human antibody are constructed, these cDNAs are inserted respectively into expression vectors for animal cells having DNA encoding CH and CL of a human antibody so as to construct a humanized antibody expression vector, and this vector is inserted into animal cells to express the humanized antibody.

Based on the sequences of the AhR polypeptide (see FIG. 14A), the skilled person would be able to generate antibodies directed against this polypeptide, which in turn may be used to neutralize its activity.

RNA Interference Agents Targeting AhR

In another embodiment, the AhR suppressor (e.g., inhibitor/antagonist) is an RNA interference agent targeting an mRNA encoding AhR. The term "RNA interference agent" as used herein refers to molecules that specifically binds to a target mRNA and induces its degradation (usually through the RNA-induced silencing complex (RISC) or interferes with its translation, and includes for example microRNA (miRNA) molecules, antisense molecules, small interfering RNA (siRNA) molecules and small/short hairpin RNA (shRNA). Chemically modified nucleosides, such as 2'-substituted arabinonucleosides (e.g., 2'F-ANA) and 2'-substituted RNA (e.g., 2'F-RNA), may be used for incorporation into RNA interference agents to enhance one or more properties, such as nuclease resistance, pharmacokinetics or affinity for a target RNA.

The RNA interference agent may be expressed from recombinant viral vectors, such as vectors derived from adenoviruses, adeno-associated viruses, lentiviruses, retroviruses, herpesviruses, and the like. Such vectors typically comprise a sequence encoding an RNA interference agent of interest and a suitable promoter operatively linked to the RNA interference agent for expressing the RNA interference agent. The vector may also comprise other sequences, such as regulatory sequences, to allow, for example, expression in a specific cell/tissue/organ, or in a particular intracellular environment/compartment. Methods for generating, selecting and using viral vectors are well known in the art.

An siRNA targeting AhR is disclosed in Abdelrahim et al., *Molecular Pharmacology* June 2003 vol. 63 no. 6: 1373-1381: 5'-UACUUCCACCUCAGUUGGCTT-3' (sense, SEQ ID NO:3), 3'-TTAUGAAGGUGGAGUCAACCG-5' (antisense, SEQ ID NO:4). Two siRNA targeting AhR are also disclosed in Ishida et al., *Carcinogenesis* vol. 31 no. 2 pp. 287-295, 2010: 5-GCCGAGUCCCAUAUCCGAAUG-3 (sense, SEQ ID NO:5), 5-GACGUAUGUCCAAGAUUC-UUU-3 (antisense, SEQ ID NO:6). RNA interference agents directed against AhR are also commercially available. For example, AhR shRNA are available from Origene (Catalog # TG320259). AhR siRNA are available from Origene (Catalog # SR300136), Qiagen (Catalog # SI00293587, SI00293594, SI02780148, SI03043971 and SI03050747), Santa Cruz Biotechnology (Catalog # sc-29654), Life Technologies (Catalog # s1198, s1199, s1200, s199481) and Dharmacon/Thermo Scientific (ON-TARGET plus SMARTpool® siRNA reagent), for example. Reagents and kits for performing RNA interference are available commercially from for example Ambion Inc. (Austin, Tex., USA), New England Biolabs Inc. (Beverly, Mass., USA), Sigma-Aldrich and Invitrogen (Carlsbad, Calif., USA).

Small-Molecule AhR Suppressors

WO 2007/128723 discloses small-molecule AhR suppressors of the formula:

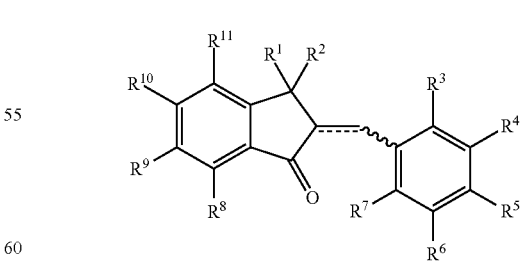

in which R1 and R2 independently of one another are hydrogen or C1-C12-alkyl, R3 to R11 independently of one another are hydrogen, C1-C12-alkyl, hydroxyl or C1-C12-alkoxy, and the broken line represents either a double bond or two hydrogens. This includes the following compounds:

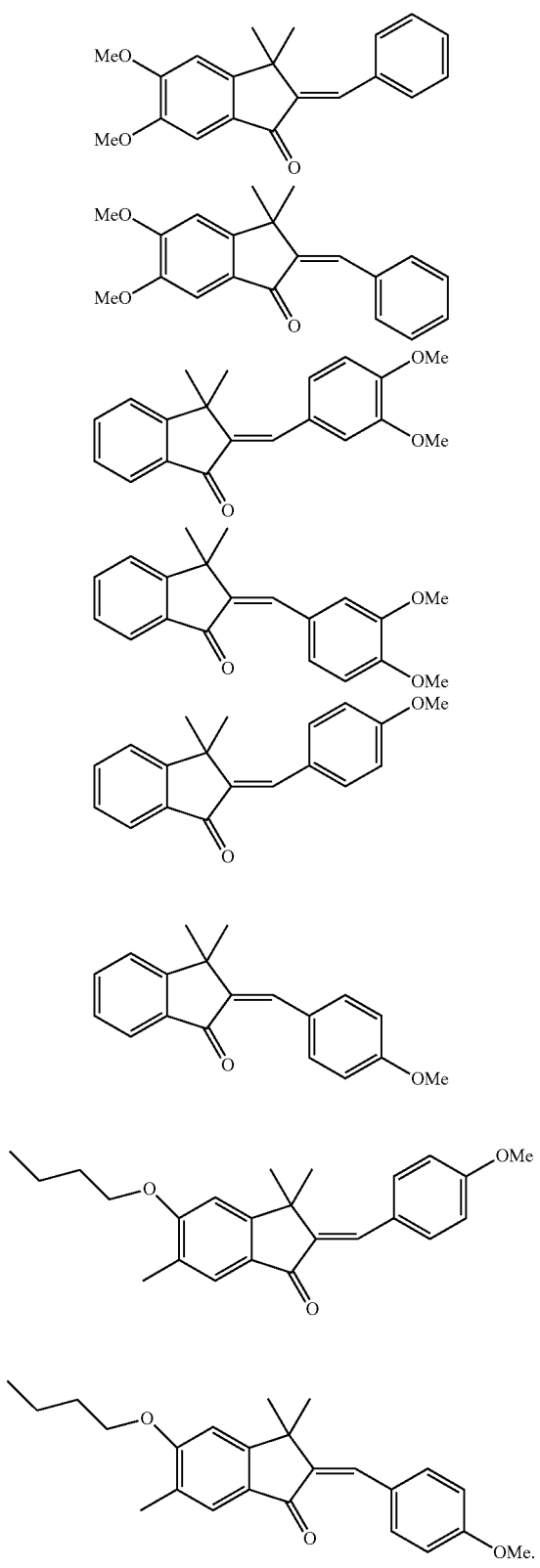

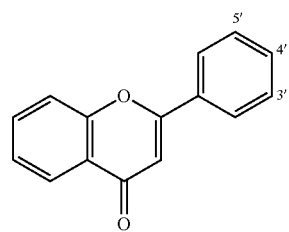 [SMILES: O=c1cc(-c2ccccc2)oc2ccccc12]

in which the 5' position is hydrogen or iodo, the 4' position is selected from hydrogen, iodo, azido, nitro, a group —NCS, cyano, amino or a group —NHCOCH₃; and the 3' position is hydroxy or lower alkoxy having from 1 to 3 carbon atoms, which may be saturated or unsaturated. Preferred flavone compounds of this class include those with a 3'-methoxy group and a 4'-substituent having one or more terminal atoms of high electron density (—N₃, —NO₂, or —NCS). Particular compounds include 3'-methoxy-4'-nitroflavone (WO 2009/115807, Henry et al., *Mol. Pharmacol* 55: 716-725, 1999).

Other AhR suppressors are the flavonoids 7,8-Benzoflavone and 2',4',6-Trimethoxyflavone:

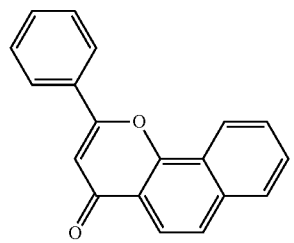

7,8-Benzoflavone

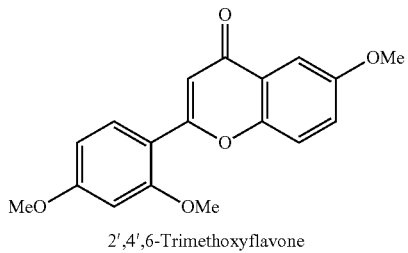

2',4',6-Trimethoxyflavone

Another AhR suppressor is the indole derivative 3,3'-diindolymethane (DIM) (Hestermann et al., *Mol. Cell. Biol.* 23: 7920-7925, 2003), of the formula:

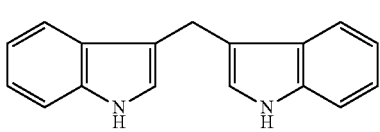

DIM

Other examples of AhR suppressors include the dietary flavonoids such as flavone, apigenin and naringenin (US 2004/0077080), as well as flavonoid compounds of the formula:

AhR suppressors are also disclosed in WO 2012/015904, for example CB7993113, CMLD-2166 and CB7950998:

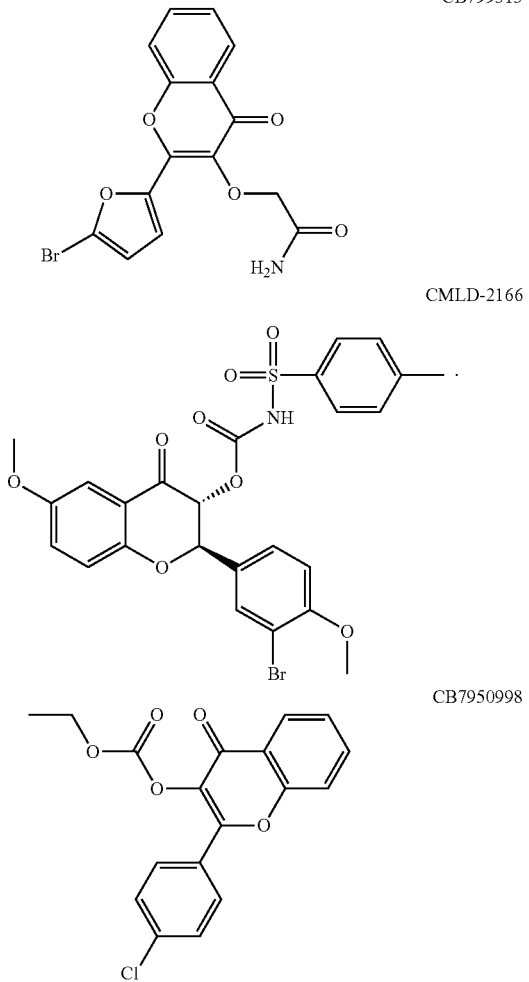

WO 2012/015904 also discloses AhR suppressors of the following formula:

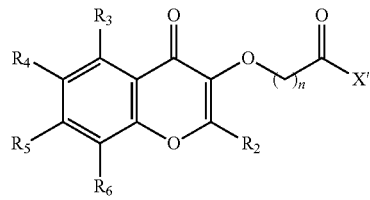

wherein: X' is H, alkyl, aminosulfonyl, alkoxy, amino, acyl, aryl, or heteroaryl (preferably alkyl, alkoxy, amino, or aminosulfonyl), each of which may be optionally substituted; n is 0-6 (preferably 0 or 1); $R_2$ is H, alkyl, acyl, aryl, heteroaryl, arylalkyl, cycloalkyl, heteroarylalkyl, heterocyclyl, or haloalkyl (preferably aryl, substituted aryl, heteroaryl, or substituted aryl), each of which may be optionally substituted; $R_3$, $R_4$, R5 and $R_6$ are independently H, alkyl, acyl, halo, aryl, or heteroaryl (preferably H, alkoxy, alkyl, or halo), each of which may be optionally substituted; and pharmaceutically acceptable salts thereof.

WO 2012/015904 also discloses AhR suppressors of the following formula:

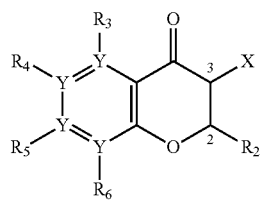

wherein: Y is C or N; X is OR1, NHR1, SR1, CH$_2$(n)R1, halo, or H; n is 0-6; Z is O, S, or NH; R1; and R2 are independently H, alkyl, alkenyl, alkynyl, amino, aminosulfonyl, alkoxy, acyl, aryl, heteroaryl, arylalkyl, cycloalkyl, heteroarylalkyl, heterocyclyl, or haloalkyl, each of which may be optionally substituted; R3, R4, R5 and R6 are independently absent, H, halo, alkyl, alkenyl, alkynyl, alkoxy, acyl, aryl, heteroaryl, arylalkyl, cycloalkyl, heteroarylalkyl, heterocyclyl, or haloalkyl, each of which may be optionally substituted; and stereoisomers thereof. In some embodiments of these aspects, the C at position 2 is in the R configuration and the C at position 3 is in the S configuration. In some embodiments of these aspects, the C at position 2 is in the S configuration and the C at position 3 is in the R configuration. In some embodiments of these aspects, the C at position 2 is in the R configuration and the C at position 3 is in the R configuration. In some embodiments of these aspects, the C at position 2 is in the S configuration and the C at position 3 is in the S configuration.

Another example of AhR suppressor is the compound CH-223191, 2-methyl-2H-pyrazole-3-carboxylic acid-(2-methyl-4-o-tolyazophenyl)-amide, of the formula:

WO 2012/015904 also discloses AhR suppressors of the following formula:

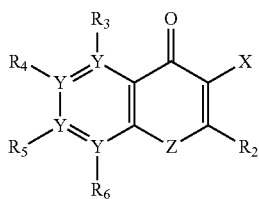

wherein: Y is C or N; X is OR1, NHR1, SR1, CH$_2$(n)R1, halo, or H; n is 0-6; Z is O, S, or NH; R1; and R2 are independently H, alkyl, alkenyl, alkynyl, amino, aminosulfonyl, alkoxy, acyl, aryl, heteroaryl, arylalkyl, cycloalkyl, heteroarylalkyl, heterocyclyl, or haloalkyl, each of which may be optionally substituted; R3, R4, R5 and R6 are independently absent, H, halo, alkyl, alkenyl, alkynyl, alkoxy, acyl, aryl, heteroaryl, arylalkyl, cycloalkyl, heteroarylalkyl, heterocyclyl, or haloalkyl, each of which may be optionally substituted; pharmaceutically acceptable salts thereof.

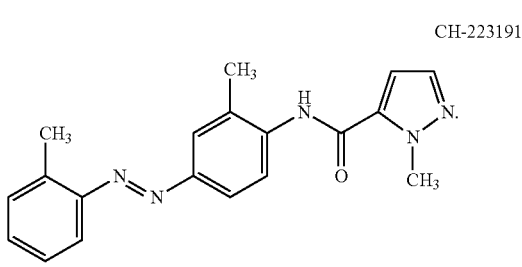 [SMILES: Cc1ccccc1/N=N/c1ccc(NC(=O)c2ccnn2C)c(C)c1]

CH-223191

WO 2004/041758 discloses AhR suppressors (stilbene derivatives) of the formula:

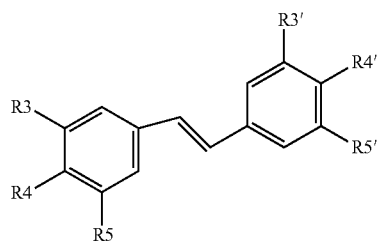

wherein R3, R4 and R5 and R3', R4' and R5' are identical or different and represent H, OH, O-alkoxy or hal, said alkoxy group being a C1-C6 alkoxy and "hal" being F, Cl or CF$_3$, with the proviso that one of R4', R3 and R5 or R4, R3' and R5' does not represent OH, OCH$_3$, or OCH$_2$CH$_3$ when the two other substituents are both OH, OCH$_3$, or OCH$_2$CH$_3$, respectively.

Another AhR suppressor is N-(2-(1H-indol-3-yl)ethyl)-9-isopropyl-2-(5-methylpyridin-3-yl)-9H-purin-6-amine (GNF351), disclosed in Smith et al., *JPET* July 2011 vol. 338 no. 1 318-327.

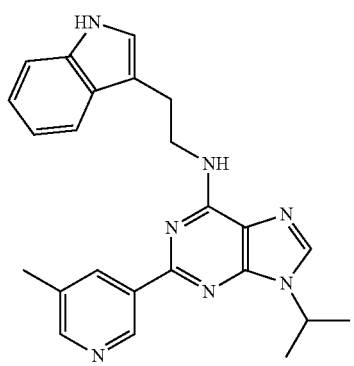

GNF351

Another AhR suppressor is 1,3-dichloro-5-[(1E)-2-(4-chlorophenyl)ethenyl]-benzene (PDM 2), which has the following structure:

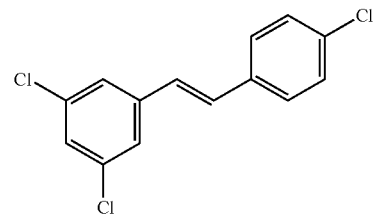 [SMILES: Clc1ccc(/C=C/c2cc(Cl)cc(Cl)c2)cc1]

Another AhR suppressor is StemRegenin 1 (SR1), which has the following structure:

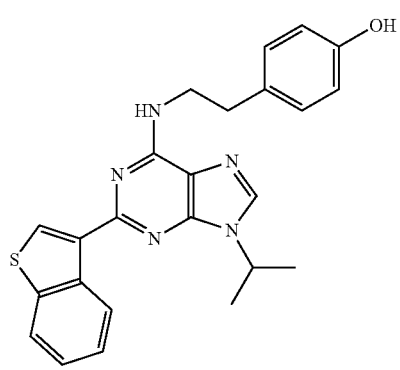 [SMILES: CC(C)n1cnc2c(NCCc3ccc(O)cc3)nc(-c3csc4ccccc34)nc21]

Figure 1B:
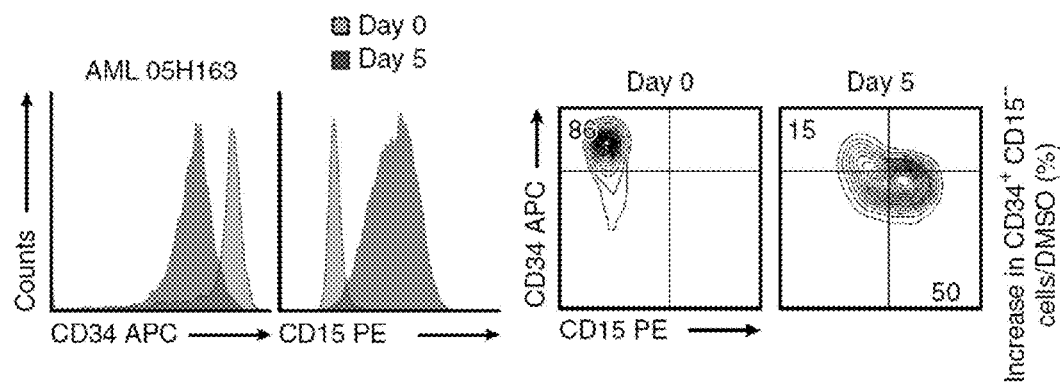
FIG. 1B depicts plots showing typical phenotypic changes (loss of CD34, acquisition of CD15) occurring upon in vitro culture of AML 05H163.
Figure 1C:
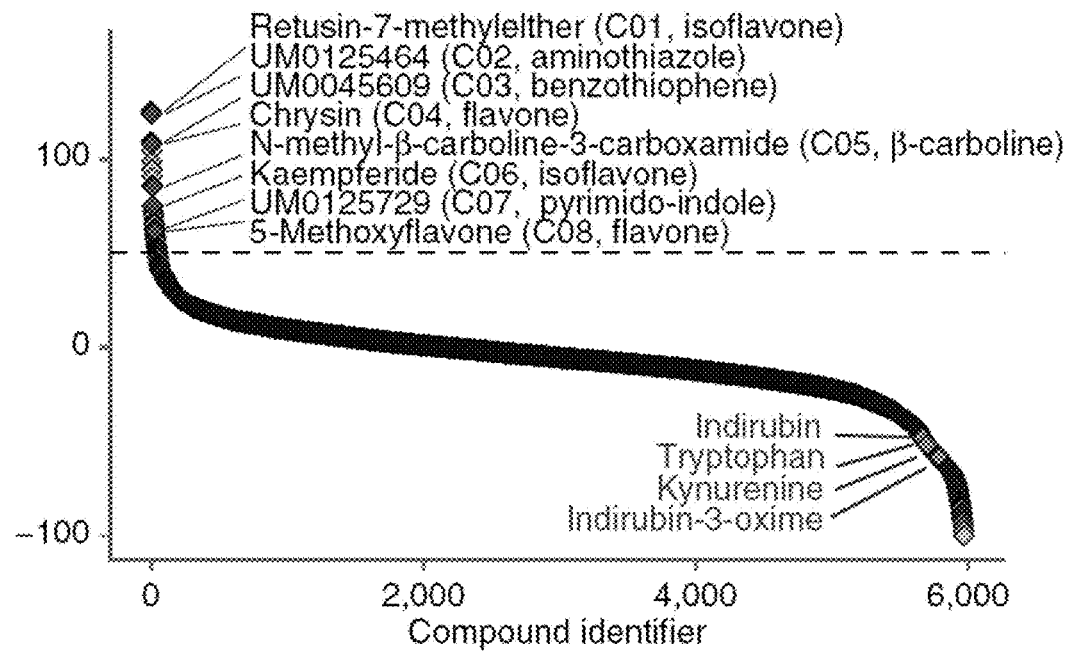
FIG. 1C shows a waterfall plot of 5,969 screen compounds complying with viability criteria. The names of compounds matching with secondary screen criteria are depicted above the dotted line. The compounds depicted at the right bottom corner (below the dotted line) are AhR-agonists and they induce further differentiation compared to the DMSO only culture condition.
Figure 1D:
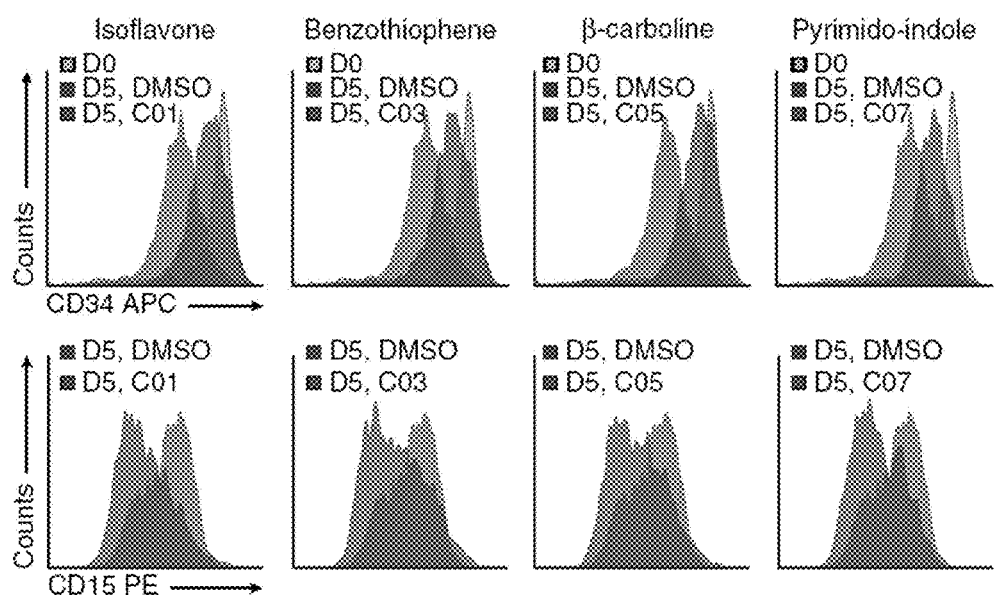
FIG. 1D shows the impact of the indicated compounds on CD34 and CD15 expression compared to DMSO after 5 days in culture (secondary screens). Dashed line in upper panels indicates CD34 profile of AML cells at $t_0$.
Figure 1E:
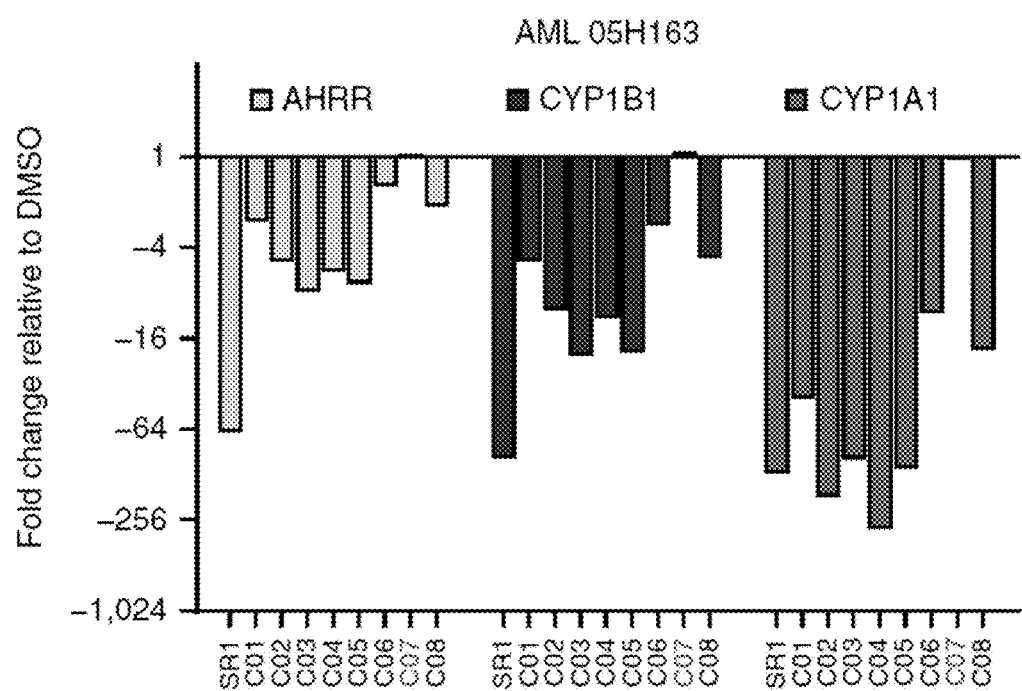
FIG. 1E shows the changes in expression levels of the indicated markers after 24 h incubation with selected compounds compared to DMSO, measured by q-RT-PCR with GAPDH as endogenous control. Note that C07 (UM729) has no effect on AhR target genes, suggesting that it acts on a different target.
Figure 1F:
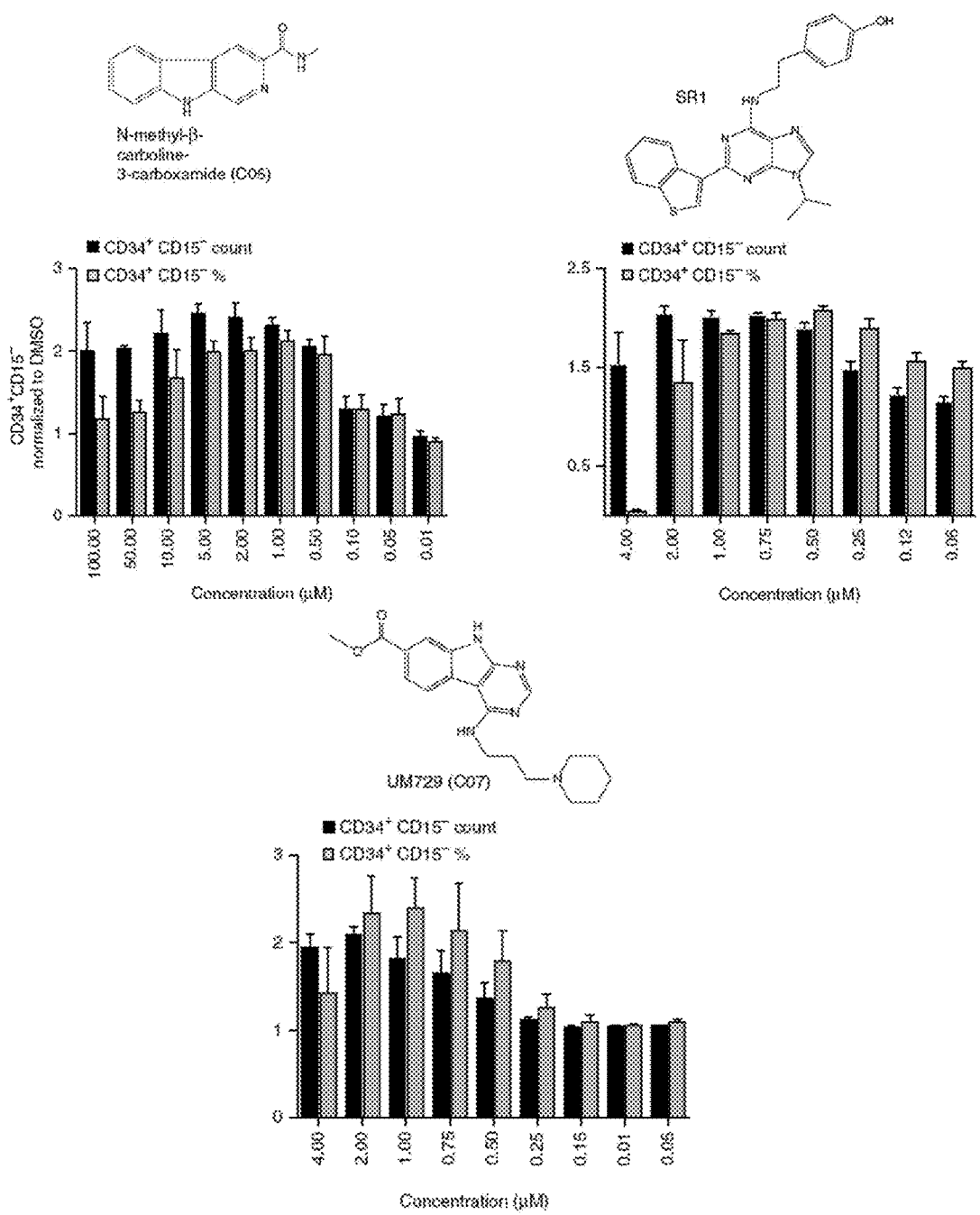
FIG. 1F shows the chemical structures and dose response experiments for the three compounds selected for validation. Black bars indicating CD34$^+$CD15$^-$ absolute cell counts refer to left y-axis, grey bars indicating CD34$^+$CD15$^-$ percentages refer to right y-axis (means±SD, n=3 (C05, SR1), n=2 (UM729) wells/dose, 384-well plate)

Additional AhR suppressors are listed in Table 1, FIG. 1C, FIG. 1F and FIG. 6, and include retusin-7-methylether, UM0125464, chrysin, kaempferide, xanthone, 3-chloro-N-(2,3-dihydro-1,4-benzodioxin-6-yl)-1-benzithiophene-2-carboxamide, 5-methoxyflavone, N-methyl-β-carboline-3-carboxamide.

Another compound that was shown to (i) inhibit or prevent the differentiation of acute myeloid leukemia (AML) initiating cells ex vivo, and/or (ii) promote the expansion or maintenance of undifferentiated primary AML blasts ex vivo; and/or (iii) partially rescue (i.e., near maintain) AML initiating activity ex vivo is methyl 4-((3-(piperidin-1-yl)propyl)amino)-9H-pyrimido[4,5-b]indole-7-carboxylate (referred to as UM729 in the Examples below), which has the following structure:

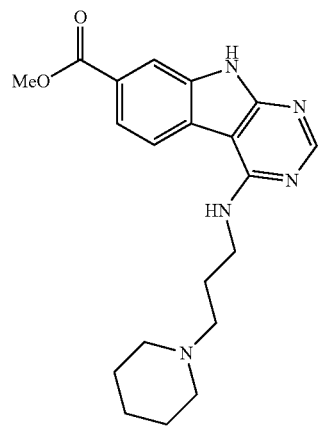 [SMILES: COC(=O)c1ccc2c(c1)[nH]c1ncnc(NCCCN3CCCCC3)c12]

Compounds structurally related to UM729 are disclosed in US2015/011543 and include the compound of general formula I-VI, IIA-IIC, IVA, VIA, or any of compounds 2 to 55 defined above. Methods to synthesize such compounds are described in US2015/011543 which is incorporated by reference.

In an embodiment, the above-mentioned method comprises (a) providing a cell population comprising said AML initiating cells and (b) culturing said cell population ex vivo under suitable conditions for expanding undifferentiated primary AML blasts The cell population (e.g., AML specimen/cell sample) may first be subjected to enrichment or purification steps, including negative and/or positive selection of cells based on specific cellular markers (e.g., CD34+, CD38−, CD123, TIM3, CD96, etc.) in order to provide a starting cell population. Methods for isolating said starting cell population based on specific cellular markers may use fluorescent activated cell sorting (FACS) technology or solid or insoluble substrate to which is bound antibodies or ligands that interact with specific cell surface markers. For example, cells may be contacted with a solid substrate (e.g., column of beads, flasks, magnetic particles) containing the antibodies and any unbound cells are removed. When a solid substrate comprising magnetic or paramagnetic beads is used, cells bound to the beads can be readily isolated by a magnetic separator.

The cell culture may be carried out in natural medium, a semi-synthetic medium or a synthetic medium in terms of composition, and may be a solid medium, a semisolid medium or a liquid medium in terms of shape, and any nutrient medium used for cell culture, which may be supplemented with a mixture of cell expanding factors. Such medium typically comprises sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be incorporated in the medium may be fetal calf serum, human serum, horse serum, insulin, transferrin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. For example, the medium may be supplemented with a combination of bovine serum albumin, insulin, transferrin (BIT). Examples of such basal medium appropriate for a method of culturing cells without limitation, Dulbecco's Modified Eagles's Medium (DMEM), Ham's Nutrient Mixture H12 Mixture F12, McCoy's 5A medium, Eagles's Minimum Essential Medium (EMEM), αMEM medium (alpha Modified Eagles's Minimum Essential Medium), RPMI1640® medium, Isocove's Modified Dulbecco's Medium (IMDM), StemPro34 (Invitrogen®), X-VIVO 10 (Cambrex), X-VIVO 15 (Cambrex®) and Stemline® II (Sigma-Aldrich), StemSpan® Serum-Free Expansion Medium (SFEM) (StemCell Technologies®, Vancouver, Canada), StemSpan® H3000-Defined Medium (StemCell Technologies®, Vancouver, Canada), CellGro®, SCGM (CellGenix®, Freiburg Germany), and StemPro®-34 SFM (Invitrogen®).

In another aspect, the present invention provides a method for determining whether a test agent may be useful for inhibiting and/or eliminating AML initiating cells, said method comprising (a) culturing a cell population comprising AML initiating cells in the presence of an suppressor of the Aryl hydrocarbon Receptor (AhR) and/or a compound of general formula I-VI, IIA-IIC, IVA, VIA, or any of compounds 1 to 55 defined above; (b) contacting said cell population with said test agent; (c) determining whether AML initiating cells are inhibited and/or eliminated in the presence of the test agent.

In another aspect, the present invention provides a method for determining whether a test agent may be useful for inhibiting and/or eliminating AML initiating cells, said method comprising (a) culturing a cell population comprising AML initiating cells in the presence of a compound set forth in Table 1 below; (b) contacting said cell population with said test agent; (c) determining whether AML initiating cells are inhibited and/or eliminated in the presence of the test agent.

The above-noted screening method or assay may be applied to a single test compound or to a plurality or "library" of such compounds (e.g., a combinatorial library). Any such compounds may be utilized as lead compounds and further modified to improve their therapeutic, prophylactic and/or pharmacological properties for inhibiting and/or eliminating AML initiating cells.

Test compounds (drug candidates) may be obtained from any number of sources including libraries of synthetic or natural compounds, including peptide/polypeptide libraries, small molecule libraries, RNAi libraries. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Screening assay systems may comprise a variety of means to enable and optimize useful assay conditions. Such means may include but are not limited to: suitable buffer solutions, temperature control means and detection means.

Elimination or Inhibition of AML Initiating Cells

The present inventors have shown that activation of the AhR pathway is associated with the differentiation and/or elimination of AML initiating cells.

Accordingly, in another aspect, the present provides a method for (i) stimulating the differentiation, and/or (ii) inhibiting the expansion or maintenance, of acute myeloid leukemia (AML) initiating cells ex vivo, said method comprising culturing said cells in the presence of an agonist of the Aryl hydrocarbon Receptor (AhR).

In another aspect, the present invention provides a method for inhibiting or eliminating AML initiating cells in a subject, said method comprising administering to said subject an effective amount of a pharmaceutically acceptable agonist of the Aryl hydrocarbon Receptor (AhR).

AhR agonist refers to an agent capable of activating the AhR pathway, which may be assessed by detecting the expression of one or more AhR target genes, such as the AhR repressor AHRR, and isozymes of the cytochrome P450 family 1 such as CYP1B1, CYP1A1 and CYP1A2.

"Pharmaceutically acceptable" as used herein refers to an agent that is not toxic to the subject when used at a biologically effective dose.

AhR agonists/ligands include synthetic and naturally occurring compounds. Synthetic AhR agonists/ligands include halogenated aromatic hydrocarbons (polychlorinated dibenzodioxins, dibenzofurans and biphenyls) and polycyclic aromatic hydrocarbons (3-methylcholanthrene, benzo-α-pyrene, benzanthracenes and benzoflavones). Naturally occurring compounds that have been identified as ligands of Ahr include derivatives of tryptophan such as indigo dye and indirubin, tetrapyrroles such as bilirubin, the arachidonic acid metabolites lipoxin-A4 and prostaglandin G, modified low-density lipoprotein and several dietary carotinoids (Denison et al., Chem. Biol. Interact. 141 (1-2): 3-24; Annu. Rev. Pharmacol. Toxicol. 43: 309-34; Adachi J et al., J. Biol. Chem. 276 (34): 31475-8; Sinal C J and Bend J R (1997). Mol. Pharmacol. 52 (4): 590-9; Seidel S D, et al. (2001). J. Biochem. Mol. Toxicol. 15 (4): 187-96; McMillan B J and Bradfield C A (2007) Proc. Natl. Acad. Sci. U.S.A. 104 (4): 1412-7; Stevens et al., Immunology. 2009 July; 127(3): 299-311). Examples of AhR agonists/ligands include: 6-formylindolo(3,2-b)carbazole (FICZ), indolo(3,2-b)carbazole (ICZ),2-(1'H-indole-3'-carbonyl)-thiazole-4-carboxylic acid methyl ester (ITE) and its precursor 2-(1'H-indole-3'-carbonyl)-thiazole-4-carboxylate (ITC) (and analogs thereof disclosed in U.S. Pat. No. 7,419,992), polycyclic aromatic hydrocarbon (PAH), polychlorinated biphenyl (PCB), 2,3,7,8 tetrachlorodibenzo-p-dioxin (TCDD), β-nephthoflavone (BNF), 3-indoxyl-sulfate (I3S), 1-(4-Methylphenyl)-2-(4,5,6,7-tetrahydro-2-imino-3(2H)-benzothiazolyl)ethanone hydrobromide (Pifithrin-α hydrobromide), (2'Z,3'E)-6-Bromo-1-methylindirubin-3'-oxime (MeBIO).

AhR agonists/ligands are disclosed in Bisson et al., J. Med. Chem. 2009, 52: 5635-5641, for example, 5-hydroxy-7-methoxyflavone, 7-methoxyisoflavone, 6-methylflavone, 3-hydroxy-6-methylflavone, pinocembrin (5,7-dihydroxy-flavanone) and 7,8,2'-trihydroxyflavone.

Another example of AhR agonist is compound VAF347 [4-(3-chlorophenyl)-N-[4-(trifluoromethyl)phenyl]pyrimidin-2-amine], and its pro-drug version VAG539 [4-(3-chloro-phenyl)-pyrimidin-2-yl]-(4-trifluoromethyl-phenyl)-carbamic acid 2-[(2-hydroxy-ethyl)-methyl-amino]-ethyl ester] (Lawrence B P, Blood 112(4):1158-65, 2008). VAF347 has the following structure:

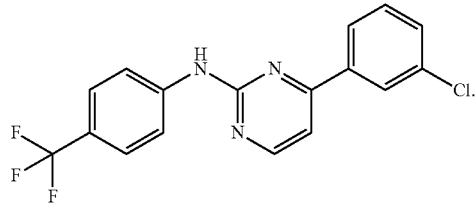

VAF347

Another example of AhR agonist is Semaxanib (SU5416) [3-(3,5-dimethyl-1H-pyrrol-2-ylmethylene)-1,3-dihydro-indole-2-one]

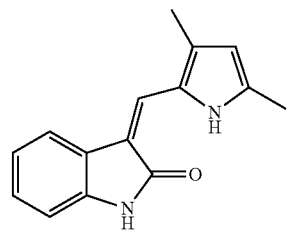

SU5416

SU5416 was initially characterized as a potent and selective synthetic inhibitor of VEGF receptor/pathway, but was shown to be an aryl hydrocarbon receptor (AhR) agonist that activates the human AHR with a potency approaching TCDD (Mezrich J D, et al. (2012) PLoS ONE 7(9): e44547. doi:10.1371/journal.pone.0044547.

Relapse of AML is caused by the persistence of leukemic blasts and leukemic stem cells (AML initiating cells) after therapy. The small proportion of morphologically undetectable residual leukemic cells that persist after chemotherapy is called minimal residual disease (MRD). The elimination or inhibition of AML initiating cells in a subject using a pharmaceutically acceptable AhR agonist may thus be a strategy to prevent or inhibit MRD, and in turn to prevent or decrease the likelihood of AML relapse.

In the method for inhibiting or eliminating AML initiating cells, and/or for preventing or inhibiting MRD, in a subject of the present invention, the pharmaceutically acceptable AhR agonist may be formulated into a pharmaceutical composition.

Such compositions may be prepared in a manner well known in the pharmaceutical art. Supplementary active compounds can also be incorporated into the compositions. As used herein "pharmaceutically acceptable carrier" or "excipient" or "diluent" includes any and all solvents, buffers, dispersion media, coatings, antibacterial and antifungal agents, isotonic and absorption delaying agents, and the like that are physiologically compatible. The carrier can be suitable, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration (see Remington: The Science and Practice of Pharmacy by Alfonso R. Gennaro, 2003, 21th edition, Mack Publishing Company).

Formulations suitable for oral administration can consist of (a) liquid solutions, such as an effective amount of active agent(s)/composition(s) suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds/compositions of the invention include ethylenevinyl acetate copolymer particles, osmotic pumps, implantable infusion systems, and liposomes. Formulations for inhalation may contain excipients, (e.g., lactose) or may be aqueous solutions containing, for example, polyoxyethylene-9-lauryl ether, glycocholate and deoxycholate, or may be oily solutions for administration in the form of nasal drops, or as a gel.

For preparing pharmaceutical compositions from the compound(s)/composition(s) of the present invention, pharmaceutically acceptable carriers are either solid or liquid. Solid form preparations include powders, tablets, pills, capsules, cachets, suppositories, and dispersible granules. A solid carrier can be one or more substance, which may also act as diluents, flavoring agents, binders, preservatives, tablet disintegrating agents, or an encapsulating material.

In powders, the carrier is a finely divided solid, which is in a mixture with the finely divided active component. In tablets, the active component (pharmaceutically acceptable AhR agonist) is mixed with the carrier having the necessary binding properties in suitable proportions and compacted in the shape and size desired. The powders and tablets may typically contain from 5% or 10% to 70% of the active compound/composition. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use are prepared by dissolving the pharmaceutically acceptable AhR agonist in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

In embodiments, the pharmaceutical compositions are formulated to target delivery of the active agent (e.g., pharmaceutically acceptable AhR agonist) to a particular cell, tissue and/or organ, such as the bone marrow or the peripheral blood. For example, it is known that formulation of an agent in liposomes results in a more targeted delivery to the bone marrow while reducing side effects (Hassan et al., Bone Marrow Transplant. 1998; 22(9):913-8). Myeloid-specific antigens can also be used to target the bone marrow (Orchard and Cooper, Q. J. Nucl. Med. Mol. Imaging. 2004; 48(4):267-78). In embodiments, the pharmaceutical compositions are formulated to increase the entry of the agent into a cell and/or into the nucleus of a cell.

An "effective amount" is an amount sufficient to effect a significant biological effect, such as (i) decreasing the number of AML initiating cells (ii) stimulating the differentiation of AML initiating cells, and/or (iii) inhibiting the expansion or maintenance of AML initiating cells in a biological system; In an embodiment, the above-mentioned agent or composition is used in an effective amount so as to (i) decreasing the number of AML initiating cells (ii) stimulating the differentiation of AML initiating cells, and/or (iii) inhibiting the expansion or maintenance of AML initiating cells in a subject by at least 10%, 20%, 30%, 40%, 50%, 60%, 70%, 80%, 90%, 95% or 100%. An effective amount can be administered in one or more administrations, applications or dosages. The compositions can be administered one from one or more times per day to one or more times per week; including once every other day. The skilled artisan will appreciate that certain factors may influence the dosage and timing required to effectively treat a subject, including but not limited to previous treatments, the general health and/or age of the subject, the target site of action, the patient's weight, special diets being followed by the patient, concurrent medications being used, the administration route, other diseases present and other factors. Moreover, treatment of a subject with a therapeutically effective amount of the compositions described herein can include a single treatment or a series of treatments. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a patient, in the context of the present invention should be sufficient to effect/induce a beneficial biological effect in the patient over time. The size of the dose also will be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

In the method for inhibiting or eliminating AML initiating cells in a subject of the present invention, administration to the patient of a chemotherapeutic agent or other anti-leukemia therapies may be combined with the administration of the AhR agonist, with the chemotherapeutic agent being administered either prior to, simultaneously with, or subsequent to, administration of the AhR agonist. In an embodiment, the chemotherapeutic agent is an anti-leukemia (anti-AML) agent. Agents typically used for AML treatment include cytarabine (ara-C), anthracycline drugs such as daunorubicin (daunomycin) and idarubicin, cladribine (Leustatin, 2-CdA), fludarabine (Fludara) and/or topotecan. In an embodiment, the chemotherapeutic agent is used in the induction phase and/or consolidation phase of the treatment. In a further embodiment, the chemotherapeutic agent is used in the induction phase of the treatment. In an embodiment, the AhR agonist is used in the induction phase and/or consolidation phase of the treatment. In a further embodiment, the AhR agonist is used in the consolidation phase of the treatment.

The chemotherapeutic agent may be a cytotoxic agent, for example (a) Mustard gas derivatives: Mechlorethamine, Cyclophosphamide, Chlorambucil, Melphalan, and Ifosfamide (b) Ethylenimines: Thiotepa and Hexamethylmelamine (c) Alkylsulfonates: Busulfan (d) Hydrazines and triazines: Althretamine, Procarbazine, Dacarbazine and Temozolomide (e) Nitrosureas: Carmustine, Lomustine and Streptozocin (f) Metal salts: Carboplatin, Cisplatin, and Oxaliplatin (g) Vinca alkaloids: Vincristine, Vinblastine and Vinorelbine (h) Taxanes: Paclitaxel and Docetaxel (i) Podophyllotoxins: Etoposide and Tenisopide. (j) Camptothecan analogs: Irinotecan and Topotecan (k) Anthracyclines:

Doxorubicin, Daunorubicin, Epirubicin, Mitoxantrone and Idarubicin (l) Chromomycins: Dactinomycin and Plicamycin (m) Miscellaneous antitumor antibiotics: Mitomycin and Bleomycin (n) Folic acid antagonists: Methotrexate (o) Pyrimidine antagonists: 5-Fluorouracil, Foxuridine, Cytarabine, Capecitabine, and Gemcitabine (p) Purine antagonists: 6-Mercaptopurine and 6-Thioguanine (q) Adenosine deaminase inhibitors: Cladribine, Fludarabine, Nelarabine and Pentostatin (r) Topoisomerase I inhibitors: Ironotecan and Topotecan (s) Topoisomerase II inhibitors: Amsacrine, Etoposide, Etoposide phosphate and Teniposide (t) Ribonucleotide reductase inhibitors: Hydroxyurea (u) Adrenocortical steroid inhibitors: Mitotane (v) Enzymes: Asparaginase and Pegaspargase (w) Antimicrotubule agents: Estramustine (x) Retinoids: Bexarotene, Isotretinoin and Tretinoin (ATRA).

Other examples of chemotherapeutic agents include, but are not limited to: acivicin; aclarubicin; acodazole hydrochloride; acronine; adozelesin; aldesleukin; altretamine; ambomycin; ametantrone acetate; aminoglutethimide; anastrozole; anthracyclin; anthramycin; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; brequinar sodium; bropirimine; cactinomycin; calusterone; caracemide; carbetimer; carmustine; carubicin hydrochloride; carzelesin; cedefingol; cirolemycin; crisnatol mesylate; decitabine (Dacogen); demethylation agents; dexormaplatin; dezaguanine; dezaguanine mesylate; diaziquone; droloxifene; droloxifene citrate; dromostanolone propionate; duazomycin; edatrexate; eflornithine hydrochloride; EphA2 inhibitors; elsamitrucin; enloplatin; enpromate; epipropidine; erbulozole; esorubicin hydrochloride; etanidazole; etoprine; fadrozole hydrochloride; fazarabine; fenretinide; floxuridine; fluorocitabine; fosquidone; fostriecin sodium; histone deacetylase inhibitors (HDAC-Is); ilmofosine; imatinib mesylate (Gleevec, Glivec); iproplatin; lanreotide acetate; lenalidomide (Revlimid); letrozole; leuprolide acetate; liarozole hydrochloride; lometrexol sodium; lomustine; losoxantrone hydrochloride; masoprocol; maytansine; megestrol acetate; melengestrol acetate; menogaril; metoprine; meturedepa; mitindomide; mitocarcin; mitocromin; mitogillin; mitomalcin; mitosper; mycophenolic acid; nocodazole; nogalamycin; ormaplatin; oxisuran; peliomycin; pentamustine; peplomycin sulfate; perfosfamide; pipobroman; piposulfan; piroxantrone hydrochloride; plomestane; porfimer sodium; porfiromycin; prednimustine; puromycin; puromycin hydrochloride; pyrazofurin; riboprine; rogletimide; safingol; safIngol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teroxirone; testolactone; thiamiprine; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vindesine; vindesine sulfate; vinepidine sulfate; vinglycinate sulfate; vinleurosine sulfate; vinrosidine sulfate; vinzolidine sulfate; vorozole; zeniplatin; zinostatin; zorubicin hydrochloride; 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; anagrelide; anastrozole; andrographolide; angiogenesis inhibitors; antagonist D; antagonist G; antarelix; antiandrogen, prostatic carcinoma; antiestrogen; antineoplaston; antisense oligonucleotides; aphidicolin glycinate; apoptosis gene modulators; apoptosis regulators; apurinic acid; ara-CDP-D L-PTBA; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epristeride; estramustine analogue; estrogen agonists; estrogen antagonists; etanidazole; exemestane; fadrozole; fazarabine; fenretinide; filgrastim; finasteride; flavopiridol; flezelastine; fluasterone; fluorodaunorunicin hydrochloride; forfenimex; formestane; fostriecin; fotemustine; gadolinium texaphyrin; gallium nitrate; galocitabine; ganirelix; gelatinase inhibitors; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idoxifene; idramantone; ilmofosine; ilomastat; imidazoacridones; imiquimod; insulin-like growth factor-receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leuprolide and, estrogen, and progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; matrilysin inhibitors; matrix metal loproteinase inhibitors; menogaril; merbarone; meterelin; metoclopramide; MIF inhibitor; mifepristone; miltefosine; mirimostim; mismatched double stranded RNA; mitoguazone; mitolactol; mitonafide; mitotoxin fibroblast growth factor-saporin; mofarotene; molgramostim; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+ pentazocine; napavin; naphterpin; nartograstim; nedaplatin; nemorubicin; neridronic acid; nilutamide; nisamycin; nitric oxide modulators; nitroxide antioxidant; nitrullyn; 06-benzylguanine; octreotide; okicenone; oligonucleotides; onapristone; oracin; oral cytokine inducer; ormaplatin; osaterone; oxaunomycin; paclitaxel; paclitaxel analogues; paclitaxel derivatives; palauamine; palmitoylrhizoxin; pamidronic acid; panaxytriol; panomifene; parabactin; pazelliptine; peldesine; pentosan polysulfate sodium; pentrozole; perflubron; perfosfamide; perillyl alcohol; phenazinomycin; phenylacetate; phosphatase inhibitors; picibanil; pilocalne hydrochloride; pirarubicin; piritrexim; placetin A; placetin B; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; RII retinamide; rogletimide; rohitukine; romurtide; roquinimex; rubiginone BI; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; gamma secretase inhibitors, sizofuran; sobuzoxane; sodium borocaptate; sodium phenylacetate; solverol; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; leucovorin; tamoxifen methiodide; tauromustine; tazarotene; tecogalan sodium; tegafur; tellurapyrylium; telomerase inhibitors; temoporfin; tetrachlorodecaoxide; tetrazomine; thaliblastine; thiocoraline; thrombopoietin; thrombopoietin mimetic; thymalfasin; thymopoietin receptor agonist; thymotrinan; tin ethyl etiopurpurin; tirapazamine; titanocene bichloride; topsentin; toremifene; totipotent stem cell factor; translation inhibitors; triacetyluridine; triciribine; trimetrexate; triptorelin; tropisetron; turosteride; tyrosine kinase inhibitors; tyrphostins; UBC inhibitors; ubenimex; urokinase receptor antagonists; vapreotide; variolin B; vector system, erythrocyte gene therapy; thalidomide; velaresol; veramine; verdins; verteporfin; vinxaltine; vorozole; zanoterone; zeniplatin; zilascorb; and zinostatin stimalamer.

Description of Illustrative Embodiments

The present invention is illustrated in further details by the following non-limiting examples.

EXAMPLE 1

Material and Methods

AML Specimens

All AML specimens used in this study are from adult AML patients and were analyzed and cryopreserved at Leukemia Cell Bank of Quebec at Maisonneuve-Rosement Hospital, Montreal. Detailed patient and specimen characteristics are provided in FIGS. 15A-15C.

Cell Culture

AML cells were thawed in 37° C. water bath and 1:10 diluted in prewarmed Iscove's modified Dulbecco's medium (IMDM) containing 20% FBS and DNase 100 µg/ml. Cells were cultured in IMDM supplemented with 15% BIT (bovine serum albumin, insulin, transferrin, Stem Cell Technologies #09500), SCF 100 ng/ml (Shenandoah #100-04), FLT3L 50 ng/ml (Shenandoah #100-21), Il-3 20 ng/ml (Shenandoah #100-80), G-CSF 20 ng/ml (Shenandoah #100-72), β-mercaptoethanol ($10^{-4}$M), gentamicin (50 µg/ml) and ciprofloxacin (10 µg/ml). For high-throughput screening (HTS) the culture medium was prepared with 15% FBS instead of BIT. When compounds were added to the culture medium, final DMSO concentrations were 0.1% in all in vitro experiments and 0.01% when cultured cells were transplanted into NSG-mice. For co-culture experiments NIH-3T3 cells were grown in tissue culture treated 6-well-plates to ~70% confluency. $10^6$ AML cells expanded in NSG mice (05H163*) were seeded on top of the feeder layer or plated in serum-free medium without feeders in presence and absence of SR1. Cells were harvested after 24 h and RNA was isolated for q-PCR experiments as described below. To establish hypoxic culture conditions cells were cultured in a hypoxia chamber (Stem Cell Technologies, 27310) which was flushed at $t_0$ and $t_{1h}$ with a sterile gas mixture containing 1% $O_2$, 5% $CO_2$ and 94% N2 (4 min at 20 l/min).

Primary and Secondary Screens and Validation Experiments

In the primary screen cells were plated in transparent 384-wellplates (Greiner, 781182) at a density of 5,000 cells in 50 µl final volume per well. Compounds were tested at 2 µM (commercial libraries) or 1 µg/ml (Medicinal Chemistry Facility, IRIC). In secondary screenings selected compounds were tested in five serial dilutions ranging from 3× higher to 1:9 diluted concentrations compared to the concentration used in the primary screen. Information on hit compounds and selection criteria for primary and secondary screens is provided in Table 1. For validation experiments AML cells were grown in 384-well plates with 3-8 replicates per condition.

Flow Cytometry

Flow cytometry was performed on an LSR™ II cytometer equipped with an HTS-device (BD Bioscience, Primary and Secondary screens and in vitro validation experiments) or on a BD Canto™ II cytometer (BD Bioscience, Xenotransplantation and CellTrace Violet™ experiments). Cells were stained for 30 minutes at 4° C. protected from light if not otherwise indicated (CellTrace Violet™ staining). The following flow cytometry-antibodies were used: CD45 Pacific Blue (BioLegend 304029), CD33 PE (BD Bioscience 555450), CD34 APC (BD Bioscience 555824), CD3 FITC (BD Bioscience 555332), CD19 PE-Cy7 (BD Bioscience 557835), CD15 PE (BD Bioscience 555401), and anti-mouse CD45.1 APC-efluor 730 (eBioscience 47-0453-82). CD34 intensities in flow cytometry plots were set at high levels on day 0 to allow tracing of non-predictable decreases of intensities during 7 days in culture.

Morphology Analysis 2-4×$10^5$ fresh and cultured cells were centrifuged onto cytospin slides, stained with Wright stain solution for 10 minutes and washed with PBS and water prior to analysis. Pictures of cytospins were taken with a Canon® EOS 5D camera connected to a Zeiss® Axio Imager microscope (40× objective).

Cell Proliferation Assay

CellTrace™ Violet (Invitrogen/Life Technologies C34557) was added at a final concentration of 3 µM to cell suspensions ($10^7$ cells/ml) containing SR1 (500 nM), UM729 (1 µM), both compounds, or vehicle DMSO (0.1%).

CellTrace™ Violet labeled cells were stained with surface antibodies against human CD3, CD19, CD34, and CD33 on day 0, day 2, and day 4 prior to analysis on a BD Canto™ II flow cytometer. Data were analyzed using FlowJo™ version 7.6.5.

Xenotransplantation

NOD.Cg-Prkdc$^{scid}$ Il2rg$^{tm1Wjl}$/SzJ (NSG) mice were purchased from Jackson Laboratory® (Bar Harbor, Me.) and bred in a pathogen-free animal facility. All AML samples were transplanted via the tail vein into 8-12 week old sublethally irradiated (250 cGy, $^{137}$Cs-gamma source) NSG mice. AML cells were transplanted at four different cell doses in groups of four recipient mice directly after thawing, or resuspended at $5\times10^5$ cells/ml in media supplemented with SR1 (0.5-1 µM), UM729 (1 µM), both compounds, or vehicle DMSO. On day 4, equivalents of the three highest to cell doses from each of the 3-4 flasks per condition were transplanted. The technician injecting fresh and cultured cells in NSG mice was not informed about the experimental conditions. Human leukemic engraftment in mouse bone marrow was determined by flow cytometry at 10 weeks (09H043, 09H083, 08H012), or at 14 or 16 weeks for specimens 04H112 and 05H163, respectively. On average 150,000 gated events were acquired. Mice were considered positive if human cells represented >1% of the bone marrow cell population. Mice were excluded only in case of obvious non-leukemia related death (e.g. first two weeks after irradiation). To discriminate between engraftment of leukemic and normal cells present in unsorted patient samples only recipients with proportions of CD45$^+$CD33$^+$ or CD45$^+$CD34$^+$ cells higher than proportions of CD19$^+$CD33$^-$ or CD3$^+$ were considered to harbor cells of leukemic origin.

Compounds

Commercially available compounds and chemical libraries used in the screen were from Sigma (Lopac, 887), Aldrich (5), Biomol (Natural Products, 362), EMD (24), Maybridge (80), Microsource Discovery Spectrum (1129), and Prestwick Chemical Library (1126). IRIC's library comprised 2555 compounds. The following compounds were purchased as fresh powders: Stem Regenin 1 (Alichem, 41864), Myriocin (Sigma, M1177), Xanthone (Microsource, 00200523), Retusin-7-methylether (Microsource, 00240645), Chrysin (Santa Cruz, S.C.-204686), N-methyl-beta-carboline-3-carboxamide (Tocris, 0554/100), UM0045609 (3-chloro-N-(2,3-dihydro-1,4-benzodoxin-6-yl)-1-benzithiophene-2-carboxamide, Chembridge, 7295866). TCDD was purchased from Sigma (48599) dissolved in toluene. UM0125729 and UM0125464 were synthesized at the medicinal chemistry department of the institute. All powders were resuspended in DMSO and diluted in culture medium right before use. Final DMSO concentration in all conditions was 0.1% in in vitro experiments and 0.01% when cultured cells were injected into NSG mice.

RNA Isolation and q-RT-PCR

RNA was isolated from primary AML samples using Trizol® reagent according to the manufacturer's instructions (Invitrogen/Life Technologies) and reverse transcribed into cDNA using MMLV reverse transcriptase and random primers. 2× Fast Master Mix® containing primers described below and probes from the Universal Probe Library® (Roche Diagnostics) were used for q-RT-PCR reactions which were amplified in 2-3 technical replicates on an ABI 7900HT Fast Real-Time® PCR System (Applied Biosystems/Life Technologies). Analysis was done with SDS 2.2.2 software (Applied Biosystems/Life Technologies) using the comparative delta $C_T$ method with GAPDH as reference gene. The following primers and probes were used: GAPDH: 5'-AGCCACATCGCTCAGACAC-3' (forward, SEQ ID NO:7), 5'-GCCCAATACGACCAAATCC-3' (reverse, SEQ ID NO:8), probe 60, CYP1A1: 5'-AAAGGCTTTTACATCCCCAAG-3' (forward, SEQ ID NO:9), 5'-GGGTTGACCCATAGCTTCTG-3' (reverse, SEQ ID NO:10), probe 59, CYP1B1: 5'-CGGCCACTAT-CACTGACATC-3' (forward, SEQ ID NO:11), 5'-CTC-GAGTCTGCACATCAGGA-3' (reverse, SEQ ID NO:12), probe 20, AHRR: 5'-TGCTTCATCTGCCGTGTG-3' (forward, SEQ ID NO:13), 5'-AGCTGCCAAGCCTGTGAC-3' (reverse, SEQ ID NO:14), probe 72, AHR: 5'-AGCCGGT-GCAGAAAACAG-3' (forward, SEQ ID NO:15), 5'-CTAT-GCCGCTTGGAAGGAT-3' (reverse, SEQ ID NO:16), probe 33.

RNA-Sequencing

RNA-Sequencing (RNA-Seq) was performed on 50 NK-AML samples as part of the Leucégène Project at IRIC. Specimens with high proportion of blast cells were prioritized to minimize the impact of contaminating non-AML cells on transcriptome data (Supplementary Table 2). Transcriptome sequencing was done as described for our previously reported T-ALL collection (Simon, C., et al. *Genes & development* 26, 651-656 (2012)). Transcript levels are given as Reads Per Kilobase per Million mapped reads (RPKM).

Statistical Analysis

Statistical analyses of all in vitro experiments were done using Graphpad Prism v 6.01. Paired t-test was used after confirming normal distribution to compare log 2-transformed-fold changes (end value/input value) of total and CD34$^+$CD15$^-$ cells in different AML samples. Normalized CD34$^+$CD15$^-$ percentages ($t_{d7}/t_0$) were analyzed by Wilcoxon matched pairs signed rank test. Bars and error bars represent means and standard deviations (SD), or standard errors of the mean (SEM), as specified. Extreme limiting dilution analysis software (Hu, Y. & Smyth, G. K. ELDA: extreme limiting dilution analysis for comparing depleted and enriched populations in stem cell and other assays. *Journal of immunological methods* 347, 70-78 (2009); http://bioinf.wehi.edu.au/software/elda/) was used to estimate LSC frequencies with 95% confidence intervals. In cases where all mice were positive or negative, one-sided confidence intervals were calculated. Differences in LSC frequencies between culture conditions were analyzed by Chi-square test. P-values <0.05 were considered significant.

EXAMPLE 2

Small Molecules Inhibit AML Cell Differentiation Ex Vivo

To identify small molecules that expand primary human AML cells in vitro while maintaining their phenotypic, morphologic, and functional characteristics, ~6,000 compounds were tested in a chemical screen comprised of commercially available compounds and small molecules proprietary to IRIC (FIG. 1A). Given the lack of definitive markers that prospectively identify leukemic stem and progenitor cells, the continuous loss of CD34 expression and the acquisition of lineage markers was monitored by flow cytometry as an indication of ongoing differentiation during in vitro culture (FIG. 1B). CD15 was chosen as a lineage marker; this was an important secondary marker to avoid bias for compounds that directly affect CD34 gene/protein expression. Surprisingly, primary hit compounds were highly enriched (34%) for Iso-/Flavonoids (Table 1). A subset of primary compounds was therefore selected for dose-response experiments, and eight compounds that complied with secondary screen criteria were identified (FIG. 1C, Table 1 in FIGS. 15A and 15B, and FIG. 6). Representative FACS profiles illustrating the effect of four different chemotypes on CD34 and CD15 expression are shown (FIG. 1D). As flavonoids are known modulators of the AhR pathway[18-20], AhR target gene expression was determined by q-RT-PCR and seven of eight compounds were found to suppress canonical AhR target genes CYP1A1, CYP1B1 and AHRR in a similar manner to the known AhR antagonist SR1[10]. In line with the enrichment of AhR suppressors within primary hit compounds, known AhR agonists (Indirubins[21], Tryptophan and the Tryptophan metabolite Kynurenine[22]) were also found among compounds that further reduced $CD34^+CD15^-$ cell counts compared to DMSO (FIG. 1C). Two chemically distinct AhR suppressors (FIG. 1F) were selected to further elucidate the role of the AhR pathway on genetically and morphologically diverse primary human AML specimens: N-methyl-β-carboline-3-carboxamide, which yielded the highest $CD34^+CD15^-$ cell counts in secondary screenings, and the known AhR antagonist SR1. Compound UM729, which had no effect on AhR target genes (FIG. 1E, FIG. 1F), was also included in validation experiments.

TABLE 1

Hit compounds identified in primary screen

| Compound ID | Supplier | Compound Name | Chemical class/Chemotype | percent gated cells (viability) |
|---|---|---|---|---|
| UM0121179 | MICROSOURCE | Retusin 7-Methylether | Isoflavone | 82.10 |
| UM0125464 | UdeM | UM0125464 | Aminothiazole | 84.80 |
| UM0045609 | MAYBRIDGE | 3-chloro-N-(2,3-dihydro-1,4-benzodioxin-6-yl)-1-benzithiophene-2-carboxamide | Benzothiazole | 82.90 |
| UM0118950 | PRESTWICK | Chrysin | Flavone | 86.90 |
| UM0119840 | SIGMA | N-Methyl-beta-carboline-3-carboxamide | β-Carboline | 86.20 |
| UM0119298 | BIOMOL | Kaempferide | Isoflavone | 82.40 |
| UM0125729 | UdeM | UM0125729 | Pyrimido indole | 78.40 |
| UM0113898 | BIOMOL | 5-Methoxyflavone | Flavone | 82.20 |
| UM0120986 | MICROSOURCE | Xanthone | Xanthone | 81.40 |
| UM0124057 | UdeM | UM0124057 | Cyclohexylidene | 82.00 |
| UM0119319 | BIOMOL | Isorhamnetine | Flavone | 83.50 |
| UM0118952 | PRESTWICK | Kaempferol | Flavone | 78.90 |
| UM0119305 | BIOMOL | 6-Methoxyluteolin | Flavone | 83.60 |
| UM0119328 | BIOMOL | Ochratoxin A | Dihydroisocoumarin | 82.10 |
| UM0125636 | UdeM | UM0125636 | Phenol | 65.80 |
| UM0119400 | BIOMOL | Diosmetine | Flavone | 80.70 |
| UM0119199 | BIOMOL | Myriocin | Atypical amino acid | 79.90 |
| UM0118428 | MICROSOURCE | Tranylcypromine hydrochloride | Aminocyclopropan | 77.80 |
| UM0119223 | BIOMOL | Swainsonine | Alkaloid | 81.90 |
| UM0124988 | UdeM | Aline | Alkaloid | 81.50 |
| UM0119342 | BIOMOL | Gitoxigenin | Steroid | 77.10 |
| UM0119219 | BIOMOL | Rapamycin | Macrolide | 72.30 |
| UM0120664 | MICROSOURCE | Benzalkonium chloride | Alkaloid | 55.50 |
| UM0120835 | MICROSOURCE | 4-Methylesculetin | Coumarin | 84.90 |
| UM0120589 | MICROSOURCE | Methoxyvone | Flavone | 82.40 |
| UM0125540 | UdeM | UM0125540 | Aminoisoxazole | 83.30 |
| UM0121217 | MICROSOURCE | Peucenin | Chromone | 83.20 |
| UM0126742 | UdeM | UM0126742 | Aminothiazole | 82.40 |
| UM0120975 | MICROSOURCE | Isotectorigenin 7-Methylether | Isoflavone | 82.60 |
| UM0119289 | BIOMOL | Kaempferol-7-Neohesperidoside | Flavone | 84.80 |
| UM0125539 | UdeM | UM0125539 | Aminoisoxazole | 83.80 |
| UM0125453 | UdeM | UM0125453 | Aminothiadiazole | 82.60 |
| UM0118473 | PRESTWICK | Quercetine dihydrate | Flavone | 82.20 |
| UM0126675 | UdeM | UM0126675 | Thiourea | 80.90 |
| UM0126682 | UdeM | UM0126682 | Thiodiazole | 83.10 |
| UM0118614 | PRESTWICK | Apigenin | Flavone | 86.90 |
| UM0121186 | MICROSOURCE | 2-Hydroxyxanthone | Xanthone | 82.40 |
| UM0126741 | UdeM | UM0126741 | Aminothiazole | 79.40 |
| UM0120160 | SIGMA | UM0120160 | Flavone | 81.20 |
| UM0121826 | UdeM | UM0121826 | Aminothiadiazole | 85.00 |
| UM0119613 | SIGMA | 8-Bromo-cAMP sodium | Adenosine | 82.20 |
| UM0120851 | MICROSOURCE | Liquiritigenin dimethylether | Flavanone | 81.20 |
| UM0121218 | MICROSOURCE | Derrustone | Isoflavone | 83.90 |
| UM0070201 | MICROSOURCE | 4'-Methoxyflavone | Flavone | 78.10 |
| UM0119121 | PRESTWICK | Verteporfin | Benzoporphyrin | 86.80 |
| UM0045562 | MAYBRIDGE | UM0045562 | Aminooxy pyridine | 81.80 |
| UM0120947 | MICROSOURCE | Prenyletin | Coumarin | 81.10 |
| UM0120143 | SIGMA | Phenamil methanesulfonate | Phenamil methanesulfonate | 84.10 |
| UM0120559 | MICROSOURCE | Ipriflavone | Flavone | 81.00 |
| UM0126533 | UdeM | UM0126533 | Cyanopyridine | 82.40 |
| UM0121168 | MICROSOURCE | 3,8-Dimethoxyflavone | Flavone | 80.80 |

TABLE 1-continued

Hit compounds identified in primary screen

| | | | | |
|---|---|---|---|---|
| UM0120987 | MICROSOURCE | Acacetin diacetate | Flavone | 81.60 |
| UM0121173 | MICROSOURCE | 5,7-Dimethoxyflavone | Flavone | 82.00 |
| UM0120789 | MICROSOURCE | Methylorsellinic acid ethyl ester | Phenol | 84.00 |
| UM0121829 | UdeM | UM0121829 | Cyclopentadiene | 85.40 |
| UM0119416 | BIOMOL | Lupinine | Alkaloid | 85.50 |
| UM0118103 | PRESTWICK | Boldine | Alkaloid | 87.00 |
| UM0123031 | UdeM | UM0123031 | Imino pyrazole | 85.50 |
| UM0120923 | MICROSOURCE | Dictamine | Alkaloid | 82.70 |
| UM0121233 | MICROSOURCE | 2-Ethoxycarbonyl-5,7-dihydroxy-8,3',4',5'-tetramethoxyisoflavone | Flavone | 86.30 |
| UM0117304 | BIOMOL | Pratol | Flavone | 82.40 |
| UM0118703 | PRESTWICK | Chicago sky blue 6B | Diazo dye, autofluorescence confirmed | 86.30 |
| UM0120960 | MICROSOURCE | 2'-beta-Dihydrochalcone | Chalcone | 72.40 |
| UM0118758 | PRESTWICK | Acetopromazine maleate salt | Phenothiazine | 79.10 |
| UM0120964 | MICROSOURCE | Pinosylvin | Phenol | 69.90 |
| UM0118303 | PRESTWICK | Harmine hydrochloride | β-Carboline | 78.60 |
| UM0118699 | PRESTWICK | Lovastatin | Statin | 81.00 |
| UM0126684 | UdeM | UM0126684 | Thiazole | 78.80 |
| UM0121171 | MICROSOURCE | Apigenin triacetate | Flavone | 80.10 |
| UM0118175 | PRESTWICK | Luteolin | Flavone | 79.80 |
| UM0119448 | BIOMOL | Galangine | Flavone | 82.60 |
| UM0119559 | SIGMA | 4-Androstene-3,17-dione | Steroid | 82.30 |
| UM0121497 | MICROSOURCE | Tranylcypromine sulfate | Aminocyclopropan | 76.50 |
| UM0118532 | PRESTWICK | Resveratrol | Phenol | 78.00 |
| UM0126692 | UdeM | UM0126692 | Benzoazepine | 74.40 |
| UM0119468 | BIOMOL | Geraldol | Flavone | 78.50 |
| UM0121512 | BIOMOL | Fumagillin | Sesquiterpene | 78.60 |
| UM0120889 | MICROSOURCE | Dimethyl gambogate | Xanthonoid | 65.10 |

| Compound ID | gated event counts | % increase CD34+CD15− (%) | % increase CD34+CD15− (cell counts) | % increase CD34+ (%) | % increase CD34+ (cell counts) | retested in 2ndary screen (0 = no, 1 = yes) | 2ndary screen criteria fulfilled (0 = no, 1 = yes, NA if not tested) |
|---|---|---|---|---|---|---|---|
| UM0121179 | 5675.00 | 124.10 | 125.38 | 58.87 | 59.80 | 1 | 1 |
| UM0125464 | 8302.00 | 113.41 | 123.91 | 53.20 | 60.79 | 1 | 1 |
| UM0045609 | 5523.00 | 94.85 | 109.14 | 46.63 | 56.89 | 1 | 1 |
| UM0118950 | 7916.00 | 105.68 | 108.30 | 47.05 | 48.57 | 1 | 1 |
| UM0119840 | 8304.00 | 76.94 | 85.11 | 31.60 | 37.57 | 1 | 1 |
| UM0119298 | 5522.00 | 98.71 | 75.15 | 42.31 | 25.55 | 1 | 1 |
| UM0125729 | 6919.00 | 47.24 | 63.00 | 14.29 | 26.44 | 1 | 1 |
| UM0113898 | 5551.00 | 82.42 | 61.47 | 36.28 | 20.92 | 1 | 1 |
| UM0120986 | 4858.00 | 94.85 | 86.26 | 34.82 | 28.81 | 1 | 0 |
| UM0124057 | 4542.00 | 80.95 | 74.92 | 41.14 | 36.44 | 1 | 0 |
| UM0119319 | 5861.00 | 74.28 | 62.94 | 37.41 | 28.67 | 1 | 0 |
| UM0118952 | 3947.00 | 87.18 | 44.57 | 26.34 | −2.29 | 1 | 0 |
| UM0119305 | 4469.00 | 88.83 | 40.01 | 31.39 | −2.77 | 1 | 0 |
| UM0119328 | 5523.00 | 52.56 | 34.37 | 14.82 | 1.28 | 1 | 0 |
| UM0125636 | 4781.00 | 58.53 | 21.27 | 27.99 | −2.19 | 1 | 0 |
| UM0119400 | 4869.00 | 97.56 | 20.75 | 31.48 | −19.72 | 1 | 0 |
| UM0119199 | 3816.00 | 72.63 | 9.44 | 1.19 | −36.05 | 1 | 0 |
| UM0118428 | 3324.00 | 52.70 | −10.11 | 49.50 | −11.95 | 1 | 0 |
| UM0119223 | 2609.00 | 79.57 | −22.20 | 30.00 | −43.81 | 1 | 0 |
| UM0124988 | 2135.00 | 82.53 | −23.25 | 63.66 | −31.16 | 1 | 0 |
| UM0119342 | 2321.00 | 62.33 | −40.00 | 48.71 | −44.85 | 1 | 0 |
| UM0119219 | 1997.00 | 68.93 | −44.01 | 27.40 | −57.86 | 1 | 0 |
| UM0120664 | 801.00 | 133.07 | −57.89 | 45.92 | −73.74 | 1 | 0 |
| UM0120835 | 4282.00 | 111.64 | 104.34 | 22.85 | 18.23 | 0 | NA |
| UM0120589 | 6355.00 | 76.68 | 98.62 | 34.02 | 50.99 | 0 | NA |
| UM0125540 | 6697.00 | 72.52 | 95.13 | 36.21 | 54.32 | 0 | NA |
| UM0121217 | 7412.00 | 74.92 | 94.61 | 23.46 | 37.27 | 0 | NA |
| UM0119289 | 7188.00 | 50.39 | 72.47 | 12.75 | 29.49 | 0 | NA |
| UM0125539 | 6688.00 | 51.54 | 71.03 | 36.38 | 54.29 | 0 | NA |
| UM0125453 | 7650.00 | 76.22 | 70.20 | 34.39 | 29.99 | 0 | NA |
| UM0118473 | 6880.00 | 83.29 | 69.64 | 15.71 | 6.69 | 0 | NA |
| UM0126675 | 4300.00 | 61.62 | 69.64 | 39.55 | 47.07 | 0 | NA |
| UM0126682 | 4668.00 | 46.78 | 67.22 | 37.65 | 57.48 | 0 | NA |
| UM0118614 | 6981.00 | 63.93 | 66.30 | 20.12 | 22.02 | 0 | NA |

TABLE 1-continued

Hit compounds identified in primary screen

| | | | | | | | |
|---|---|---|---|---|---|---|---|
| UM0121186 | 5612.00 | 66.25 | 65.21 | 48.93 | 48.11 | 0 | NA |
| UM0126741 | 4361.00 | 57.86 | 65.20 | 16.87 | 21.99 | 0 | NA |
| UM0120160 | 8056.00 | 42.50 | 62.34 | 26.62 | 44.34 | 0 | NA |
| UM0121826 | 8944.00 | 38.23 | 61.69 | 25.59 | 46.90 | 0 | NA |
| UM0119613 | 5800.00 | 83.42 | 61.33 | 30.06 | 14.28 | 0 | NA |
| UM0120851 | 4377.00 | 63.25 | 59.21 | 34.97 | 31.66 | 0 | NA |
| UM0121218 | 6864.00 | 53.68 | 58.63 | 21.91 | 25.53 | 0 | NA |
| UM0070201 | 4754.00 | 69.03 | 58.22 | 28.71 | 20.27 | 0 | NA |
| UM0119121 | 5887.00 | 37.29 | 58.17 | 15.38 | 33.14 | 0 | NA |
| UM0045562 | 6188.00 | 31.41 | 57.76 | 16.11 | 39.35 | 0 | NA |
| UM0120947 | 4658.00 | 60.33 | 56.71 | 18.10 | 15.58 | 0 | NA |
| UM0120143 | 6917.00 | 58.21 | 54.83 | 30.88 | 28.04 | 0 | NA |
| UM0120559 | 5670.00 | 40.47 | 54.50 | 27.34 | 39.89 | 0 | NA |
| UM0126533 | 4672.00 | 35.24 | 54.31 | 8.68 | 24.44 | 0 | NA |
| UM0121168 | 5465.00 | 58.96 | 53.85 | 29.05 | 24.97 | 0 | NA |
| UM0120987 | 4869.00 | 59.88 | 53.47 | 27.58 | 22.16 | 0 | NA |
| UM0121173 | 5883.00 | 46.97 | 53.11 | 29.43 | 34.90 | 0 | NA |
| UM0120789 | 4445.00 | 52.70 | 52.88 | 22.49 | 22.38 | 0 | NA |
| UM0121829 | 7706.00 | 51.03 | 52.26 | 16.30 | 17.23 | 0 | NA |
| UM0119416 | 7430.00 | 28.13 | 51.77 | 10.12 | 30.63 | 0 | NA |
| UM0118103 | 8550.00 | 31.10 | 50.97 | −3.69 | 10.21 | 0 | NA |
| UM0120923 | 5710.00 | 33.65 | 50.43 | 13.58 | 27.61 | 0 | NA |
| UM0121233 | 6855.00 | 45.77 | 50.24 | 15.01 | 18.21 | 0 | NA |
| UM0117304 | 5475.00 | 68.85 | 47.36 | 50.40 | 31.59 | 0 | NA |
| UM0118703 | 6352.00 | 54.52 | 42.76 | 42.39 | 31.67 | 0 | NA |
| UM0120960 | 4411.00 | 63.62 | 41.99 | 24.69 | 8.21 | 0 | NA |
| UM0118758 | 6649.00 | 57.85 | 41.15 | −0.82 | −11.68 | 0 | NA |
| UM0120964 | 4446.00 | 59.46 | 39.69 | 24.20 | 8.62 | 0 | NA |
| UM0118303 | 5689.00 | 81.33 | 38.52 | 8.79 | −17.08 | 0 | NA |
| UM0118699 | 6285.00 | 62.41 | 36.94 | 1.88 | −14.30 | 0 | NA |
| UM0126684 | 3488.00 | 59.98 | 36.16 | 42.30 | 21.49 | 0 | NA |
| UM0121171 | 4467.00 | 66.25 | 31.61 | 48.36 | 17.48 | 0 | NA |
| UM0118175 | 5849.00 | 70.76 | 27.50 | 40.48 | 4.97 | 0 | NA |
| UM0119448 | 6098.00 | 60.64 | 23.06 | 30.10 | −0.57 | 0 | NA |
| UM0119559 | 6224.00 | 53.81 | 20.14 | 1.57 | −20.76 | 0 | NA |
| UM0121497 | 3425.00 | 70.66 | 19.65 | 20.22 | −15.83 | 0 | NA |
| UM0118532 | 5228.00 | 60.46 | 12.57 | 22.62 | −14.19 | 0 | NA |
| UM0126692 | 2369.00 | 56.68 | −9.43 | 53.09 | −11.13 | 0 | NA |
| UM0119468 | 3728.00 | 64.06 | −23.14 | 25.29 | −41.47 | 0 | NA |
| UM0121512 | 2089.00 | 55.51 | −46.09 | 31.22 | −54.59 | 0 | NA |
| UM0120889 | 1507.00 | 52.62 | −48.79 | 47.72 | −50.44 | 0 | NA |

| Compound ID | optimal concentration in 2ndary screen | % increase CD34+CD15− (%) 2ndary screen | % increase CD34+CD15− (cell counts) 2ndary screen |
|---|---|---|---|
| UM0121179 | 3× | 218.84 | 199.22 |
| UM0125464 | 2× | 158.94 | 210.42 |
| UM0045609 | 3× | 204.83 | 198.60 |
| UM0118950 | 2× | 194.69 | 172.16 |
| UM0119840 | 2× | 172.95 | 252.10 |
| UM0119298 | 1× | 105.80 | 114.93 |
| UM0125729 | 1× | 205.07 | 206.53 |
| UM0113898 | 2× | 105.80 | 119.91 |

UdeM: University of Montreal
% increase compared to DMSO: ((compound − DMSO)/DMSO*100)
Primary Screen Criteria:
1. ≥50% increase of CD34+CD15− cells (%) compared to DMSO AND no loss (≥0%) in absolute CD34+CD15− cell counts OR
2. ≥50% increase in absolute CD34+CD15− cell counts compared to DMSO AND
3. ≥50% gated cells (viable cells)
Secondary Screen Criteria:
1. ≥50% increase of CD34+CD15− cells (%) compared to DMSO AND
2. ≥50% increase in absolute CD34+CD15− cell counts compared to DMSO AND
3. ≥50% gated cells (viable cells) in at least one of the tested doses (5 serial dilutions ranging from 3× to 1/9 of dose tested in primary screen)

EXAMPLE 3

The AhR Pathway is Rapidly Activated in AML Cells Ex Vivo

Figure 2A:
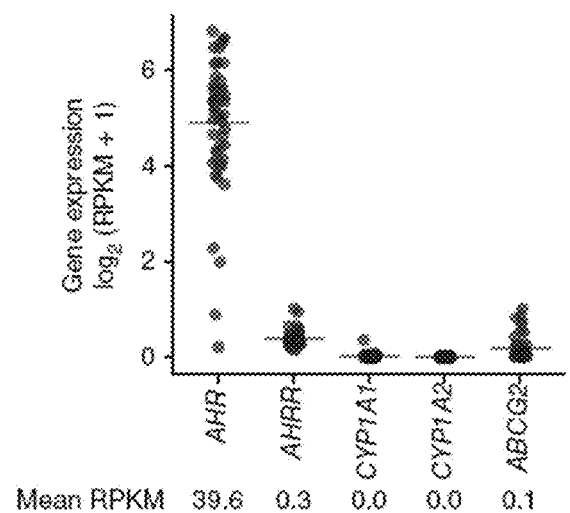
FIG. 2A shows the expression levels (RPKM) of the indicated genes in human AML specimens with normal karyotype, determined by RNA-Seq (Table 1). Bars indicate means of log 2-transformed values.
Figure 2B:
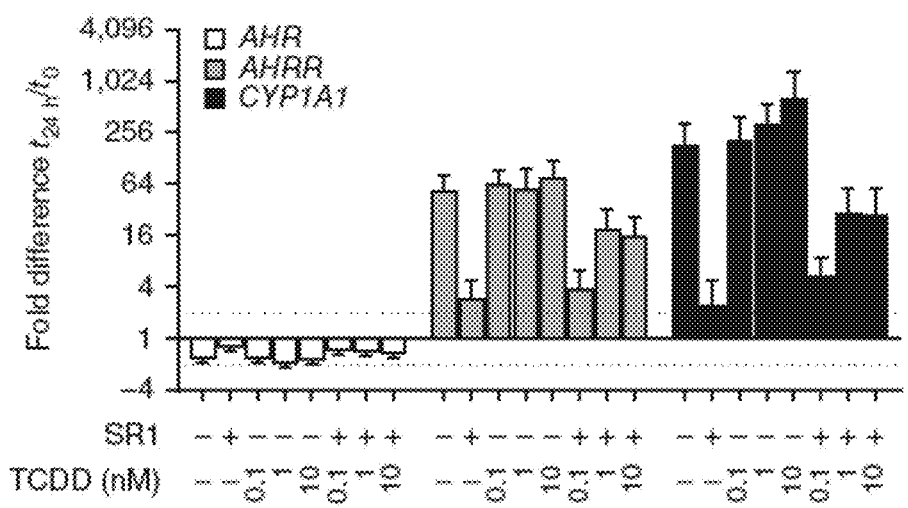
FIG. 2B Fold changes in gene expression levels (mean±SEM, n=13 samples), measured by q-RT-PCR with GAPDH as endogenous control, following 24 h exposure to the indicated compounds or combinations. TCDD, 2,3,7,8-Tetrachlorodibenzodioxin. _ no compound, SR1 was added at 500 nM, TCDD was added at 0.1 nM, 1 nM and 10 nM.
Figure 7C:
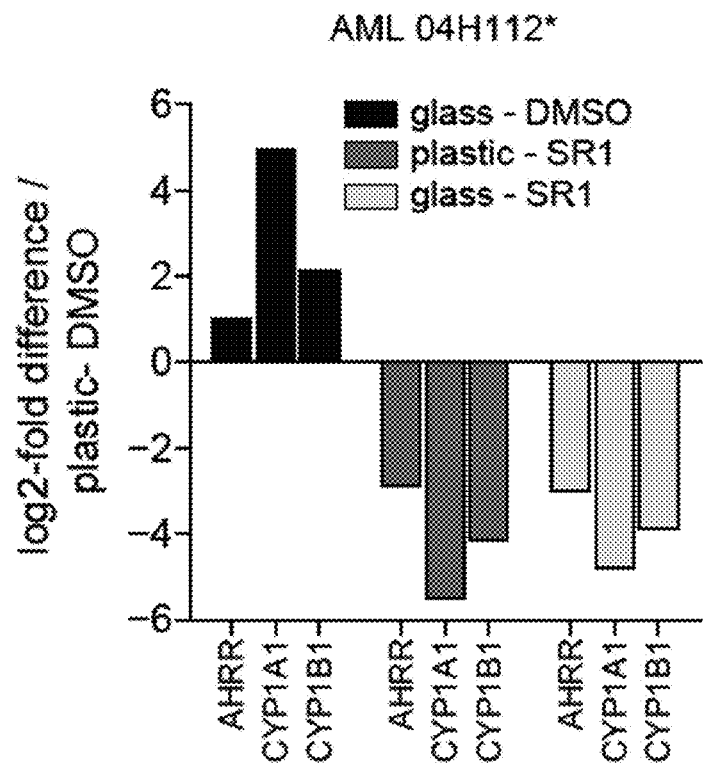
FIG. 7C shows the fold difference in AhR target gene expression after 24 h exposure to SR1 or DMSO in glass dishes, or SR1 in standard polystyrene culture dishes (plastic-SR1) compared to control DMSO and polystyrene dish (plastic-DMSO)
Figure 7D:
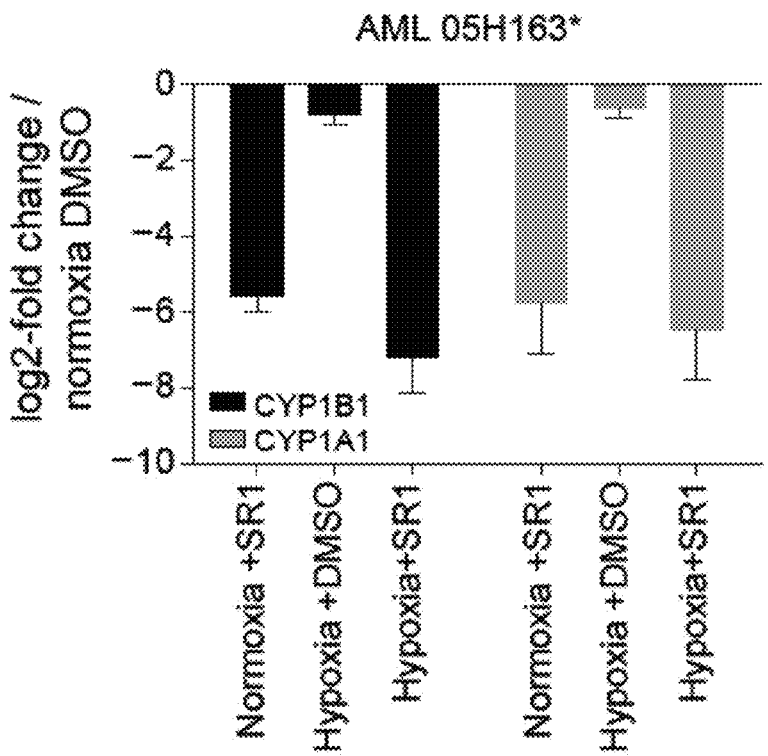
FIG. 7D shows the fold-change (mean±SEM) in AhR target gene expression after 24 h incubation under normoxic versus hypoxic (1% $O_2$) conditions, and in presence or absence of SR1 (500 nM) compared to expression levels in normoxic control conditions (Normoxia DMSO was used as reference)
Figure 7E:
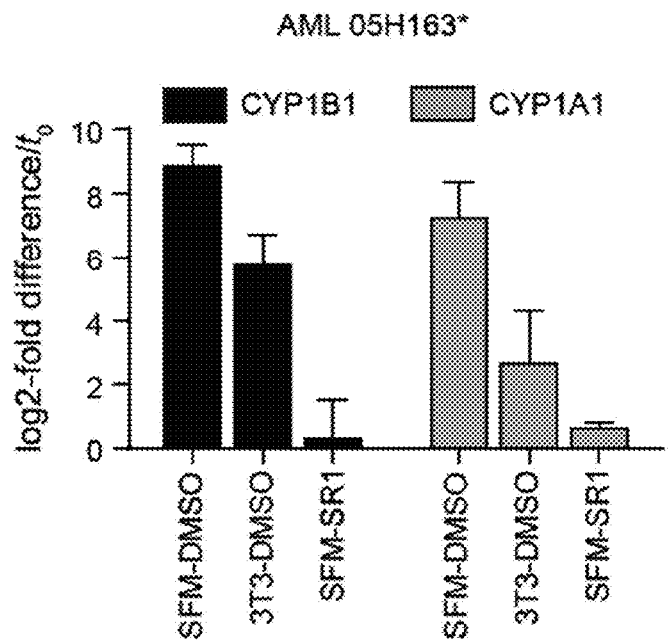
FIG. 7E shows the fold difference in AhR target gene expression after 24 h exposure to SR1 or DMSO in serum-free medium (SFM) or co-cultured on a confluent feeder layer of NIH-3T3 fibroblasts compared to $t_0$. Sample 05H163 expanded in NSG mice (05H163*) was used for experiments in FIGS. 7B, 7D and 7E, and sample 04H112 expanded in NSG mice (04H112*) for the experiment in FIG. 7D. GAPDH served as endogenous control in all experiments depicted in FIGS. 7A-7E.

Given the enrichment for AhR suppressors among hit compounds, it was assessed whether AhR suppression reflects the physiology of human AML cells in vivo and whether AhR activation was common to all AML specimens when exposed to in vitro conditions. RNA-Seq data of 50 AML specimens with normal karyotype (FIGS. 16A-16C) was examined and it was found that canonical AhR targets are not expressed, although the receptor itself is well expressed in nearly all samples analyzed (FIG. 2A). Upon 24 h in vitro culture, a marked upregulation of AhR target genes AHRR and CYP1A1 (53- and 180-fold, respectively) was observed in control conditions (DMSO). This upregulation was effectively antagonized by SR1 and could only be marginally further induced by the known AhR agonist 2,3,7,8-Tetrachlorodibenzodioxin (TCDD) indicating that the pathway is near maximally activated by in vitro culture conditions (FIG. 2B). The upregulation of AhR target genes was not transient, as their expression remained elevated during 6-day incubation (FIG. 7A). Different media lacking constituents such as the vehicle DMSO, phenol red, or antibiotics, and cultured AML cells in glass dishes and hypoxic conditions (1% $O_2$) were tested, but the same magnitude of target gene induction was observed in all conditions tested (FIGS. 7B-7D). Interestingly, when cells were cultured on a feeder layer of NIH-3T3-fibroblasts, induction of target genes was lower compared to cultures without feeders, but this suppression was not at the levels achieved by SR1 treatment (FIG. 7E).

EXAMPLE 4

Figure 3A:
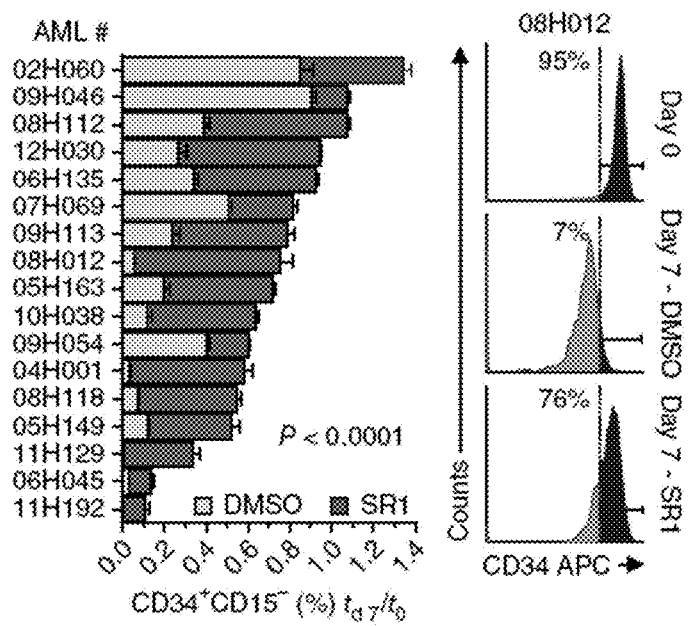
FIG. 3A shows the fractions of CD34$^+$CD15$^-$ cells (mean±SD, 3-8 replicates per sample) after 7-day culture with SR1 (0.75-1 µM), or vehicle (DMSO) normalized to fresh cells ($t_{d7}/t_0$). Wilcoxon matched-pairs signed rank test (left panel). Representative FACS profiles of AML 08H012 on day 0 and following 7-day culture with DMSO or SR1 are depicted in the right panel.
Figure 3B:
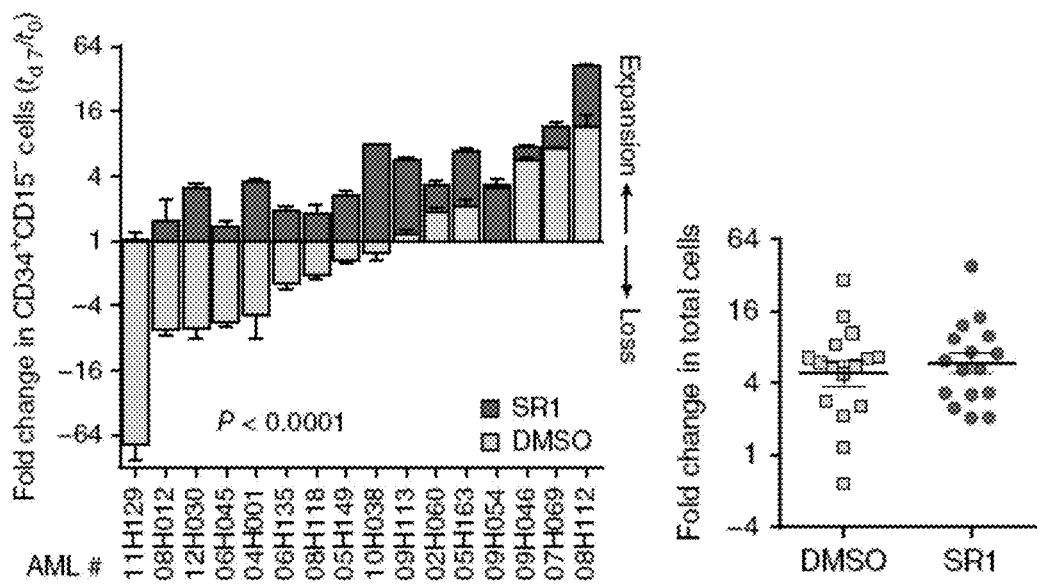
FIG. 3B shows the fold changes of CD34$^+$CD15$^-$ cell numbers (geometric mean±SD, 3-8 replicates per sample) after 7-day culture with SR1 (0.75-1 µM) or DMSO compared to input numbers ($t_{d7}/t_0$, log 2-transformed, P<0.0001, paired t-test) (right panel). The right panel shows fold changes of total cells (mean±SEM, n=16, P=0.2, paired t-test)
Figure 8A:
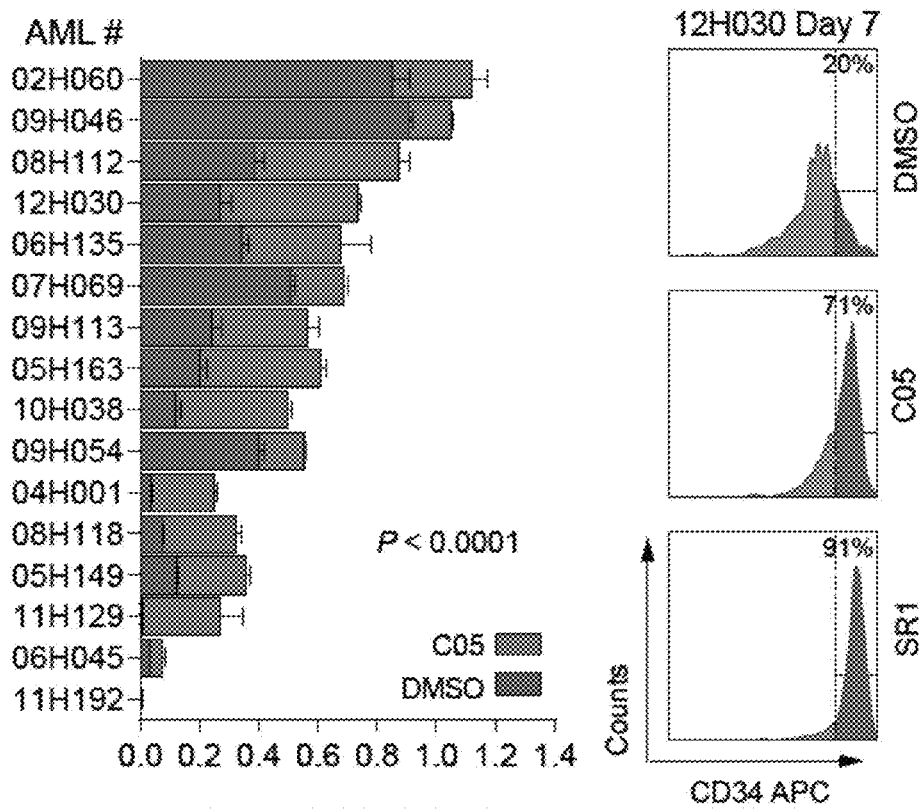
FIG. 8A shows (left panel) the proportions of $CD34^+$ $CD15^-$ cells (mean±SD) after 7-day culture with N-methyl-β-carboline-3-carboxamide (C05, 2 μM, n=16 AML samples, 3-8 technical replicates per sample), or vehicle (DMSO). Results were normalized to fresh cells ($t_{d7}/t_0$). The right panel shows FACS profiles of AML 12H030 (M0, 46,XY) after 7-day culture with DMSO, or C05 (2 μM), or SR1 (0.75 μM). On day 0, 94% of 12H030 cells were $CD34^+CD15^-$. P<0.0001, Wilcoxon matched-pairs signed rank test.
Figure 8B:
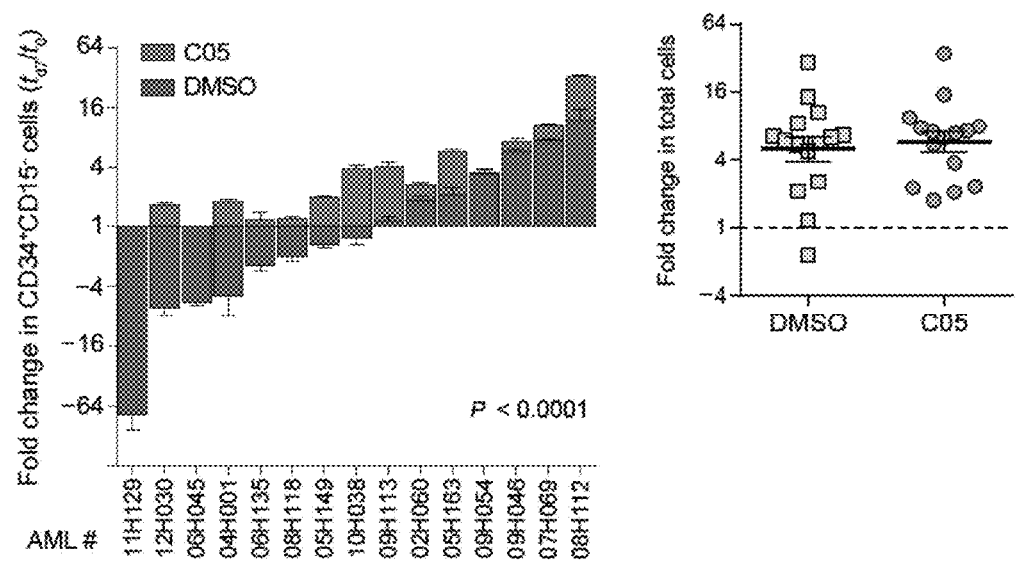
FIG. 8B shows (left panel) the fold changes of CD34+ CD15− AML cell numbers (geometric means±SD) following 7-day culture with C05 (2 μM, n=15 AML samples, 3-8 technical replicates per sample), or control DMSO compared to input numbers ($t_{d7}/t_0$, log 2-transformed). P<0.0001, paired t-test. The right panel shows the fold changes in total gated (viable) cell counts (geometric means±SEM, n=15) following 7 day culture with C05 or DMSO compared to input numbers ($t_{d7}/t_0$, log 2-transformed). P=0.2, paired t-test.

AhR Suppressors Expand Genetically Diverse $CD34^+$ AML Cells 17 genetically and morphologically diverse AML samples (Table 2) were selected and exposed to N-methyl-β-carboline-3-carboxamide (C05) and SR1 in optimized serum-free conditions. All AML specimens treated with SR1 showed higher percentages of $CD34^+CD15^-$ cells following a 7-day culture period compared to DMSO controls with a median $CD34^+CD15^-$ percentage relative to uncultured cells of 72% (SR1) versus 19% in control cultures (FIG. 3A). A similar but weaker effect was seen when AML cells were exposed to C05 (56% (C05) versus 22% (DMSO), FIG. 8A. In the absence of AhR suppression, absolute $CD34^+CD15^-$ cell numbers were reduced below input values in nine of the 16 samples with an up to 66-fold loss (FIG. 3B). In contrast, AhR suppression, whether through addition of SR1 (FIG. 3B) or C05 (FIG. 8B), had a significant impact on $CD34^+CD15^-$ cell numbers (P<0.0001, paired t-test) resulting in net expansion in almost all samples (15/16) in the presence of SR1 with up to 42-fold increase in $CD34^+CD15^-$ cell numbers (AML 08H112, 46,XY). The monocytic AML 11H192 could not be maintained in the tested culture conditions. Importantly, total cell counts in these short-term cultures were not significantly different (P=0.2) compared to control DMSO (FIGS. 3B and 8B), suggesting that AhR suppressors expand $CD34^+CD15^-$ cells by inhibiting differentiation rather than by promoting proliferation.

TABLE 2

| | 50 NK-AML | | | | RNA-Seq statistics | TruSeq |
| | | | | | | |
| Sample ID | FAB | Karyotype | RNASeq Leucegene Project | % blasts in sequenced tissue | Total reads | Mapped reads | Exon coverage (X) |
| --- | --- | --- | --- | --- | --- | --- | --- |
| 02H053 | M1 | 46,XY[20] | X | 96% | 254,354,904 | 165,800,182 | 221.213 |
| 02H066 | M1 | 46,XX[22] | X | 95% | 202,166,862 | 138,400,653 | 176.864 |
| 03H041 | M5 | 46,XX[22] | X | 83% | 139,456,674 | 98,879,311 | 132.944 |
| 03H116 | M1 | 46,XX[21] | X | 97% | 210,354,746 | 162,117,898 | 185.162 |
| 03H119 | M1 | 46,XY[20] | X | 92% | 240,466,732 | 170,488,400 | 216.359 |
| 04H024 | M1 | 46,XX[21] | X | 76% | 235,971,514 | 168,716,547 | 221.64 |
| 04H112 | M1 | 46,XX[21] | X | 91% | 314,407,390 | 211,062,439 | 279.763 |
| 04H133 | M1 | 46,XX[20] | X | 91% | 254,348,770 | 184,912,350 | 236.982 |
| 05H050 | M4 | 46,XY[20] | X | 94% | 244,252,476 | 162,065,400 | 209.772 |
| 05H094 | M5B | 46,XY[23] | X | 94% | 24,051,756 | 16,136,335 | 19.2821 |
| 05H149-R | M1 | 46,XY[20] | X | 80% | 134,708,214 | 89,494,406 | 101.48 |
| 05H163 | M1 | 46,XY[22] | X | 86% | 130,822,284 | 102,587,123 | 119.194 |
| 05H181 | M5B | 46,XX[11] | X | 80% | 157,482,558 | 117,851,283 | 150.301 |
| 06H028 | M1 | 46,XX[20] | X | 95% | 239,658,580 | 192,280,705 | 203.931 |
| 06H144 | M1 | 46,XX[20] | X | 90% | 275,126,550 | 209,487,397 | 214.754 |
| 07H062 | M1 | 46,XY[20] | X | 90% | 152,645,692 | 122,405,514 | 140.41 |
| 07H135 | M1 | 46,XY[20] | X | 97% | 238,032,296 | 179,457,947 | 210.412 |
| 08H112 | N.A. | 46,XY[20] | X | 85% | 246,299,096 | 165,427,777 | 199.009 |
| 09H043 | M1 | 46,XY[21] | X | 80% | 200,324,858 | 148,737,817 | 185.227 |
| 09H083 | M1 | 46,XX[20] | X | 94% | 272,928,142 | 210,486,994 | 193.356 |
| 09H111 | M5B | 46,XX[21] | X | 80% | 198,444,036 | 153,875,438 | 194.471 |
| 09H113 | M1 | 46,XY[22] | X | 95% | 202,205,718 | 154,075,327 | 150.744 |
| 09H115 | M1 | 46,XY[24] | X | 90% | 177,782,298 | 140,448,905 | 137.61 |
| 10H031 | M5B | 46,XX[27] | X | 73% | 294,445,232 | 227,741,140 | 258.608 |
| 10H038 | M0 | 46,XX[20] | X | 91% | 278,264,752 | 203,811,372 | 206.272 |
| 10H052 | N.A. | 46,XX[20] | X | 66% | 245,700,060 | 156,177,584 | 165.45 |
| 10H056 | M1 | 46,XX[18] | X | 83% | 149,407,924 | 109,576,242 | 133.201 |
| 10H072 | M5B | 46,XY[20] | X | 77% | 199,904,146 | 160,643,454 | 171.614 |
| 10H089 | N.A. | 46,XX[26] | X | 80% | 345,269,918 | 252,820,926 | 259.518 |
| 10H092 | M1 | 46,XX[21] | X | 90% | 132,441,898 | 86,464,545 | 101.569 |
| 10H095 | M1 | 46,XX[24] | X | 91% | 107,501,728 | 80,897,078 | 87.7174 |
| 10H101 | M1(Blood)/M2(Bone Marrow) | 46,XX[22] | X | 70% | 186,830,108 | 141,544,598 | 135.704 |
| 10H115 | M1 | 46,XY[23] | X | 88% | 232,634,008 | 175,901,037 | 168.647 |
| 10H166 | M4 | 46,XY[20] | X | 89% | 47,256,206 | 36,063,413 | 41.9361 |
| 11H006 | M5a | 46,XX[23] | X | 94% | 197,121,192 | 135,994,122 | 173.416 |
| 11H009 | M2 | 46,XY[20] | X | 70% | 125,574,140 | 97,540,825 | 92.1638 |
| 11H021 | M2 | 46,XX[20] | X | 70% | 98,971,350 | 72,044,458 | 80.2961 |
| 11H058 | M1 | 46,XY[20] | X | 90% | 213,247,132 | 158,880,141 | 195.422 |
| 11H072 | M2 | 46,XX[20] | X | 80% | 153,767,048 | 116,293,065 | 124.031 |
| 11H083 | M5A | 46,XY[20] | X | 80% | 147,602,940 | 109,415,102 | 126.551 |

TABLE 2-continued

| | 50 NK-AML | | | RNA-Seq statistics | | TruSeq |
| --- | --- | --- | --- | --- | --- | --- |
| Sample ID | FAB | Karyotype | RNASeq Leucegene Project | % blasts in sequenced tissue | Total reads | Mapped reads | Exon coverage (X) |
| 11H095 | M5A | 46,XY[20] | X | 87% | 84,723,668 | 63,993,606 | 81.0176 |
| 11H126 | M5B | 46,XY[21] | X | 68% | 115,843,254 | 90,815,288 | 113.408 |
| 11H142 | M1 | 46,XX[21] | X | 96% | 181,720,350 | 141,979,309 | 137.491 |
| 11H160 | M4 | 46,XX[22] | X | 65% | 315,611,422 | 248,270,460 | 307.426 |
| 06H045 | M2 | 46,XX[22] | X | 70% | 95,841,108 | 68,878,706 | 81.7275 |
| 07H042 | N.A. | 46,XY[20] | X | 83% | 140,483,762 | 106,332,188 | 126.59 |
| 08H048 | M1 | 46,XY[21] | X | 96% | 219,693,590 | 158,546,611 | 212.155 |
| 09H031 | M1 | 46,XX[20] | X | 85% | 238,696,800 | 165,191,997 | 211.304 |
| 11H151 | M1 | 46,XY[21] | X | 78% | 239,643,126 | 176,576,254 | 208.475 |
| 12H030 | M0 | 46,XY[20] | X | 93% | 236,172,776 | 176,340,449 | 207.64 |
| | | | mean | 85% | 195,413,236 | 143,678,602 | 166.20 |
| | | | stdev | 9% | 69,959,423.2 | 51,385,157.2 | 60.5 |

Figure 3C:
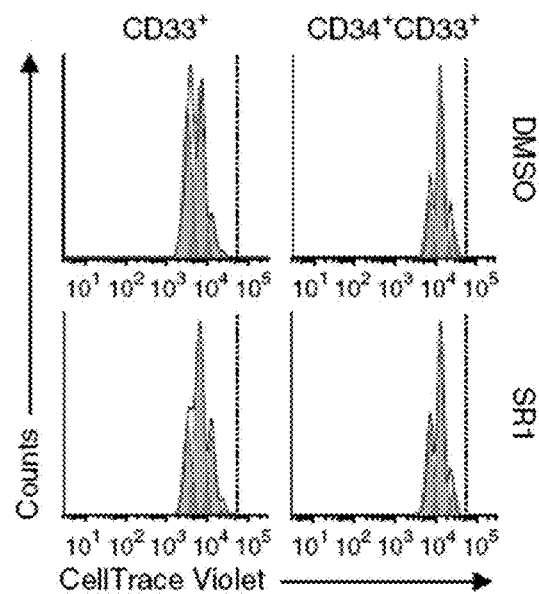
FIG. 3C shows CellTrace™ Violet profiles of CD33$^+$ and CD34$^+$CD33$^+$ AML cells (04H112 after 4-day culture with SR1 or DMSO. Dashed line indicates CellTrace™ Violet peak of fresh cells ($t_0$). Each individual peak represents one generation of cells.
Figure 3D:
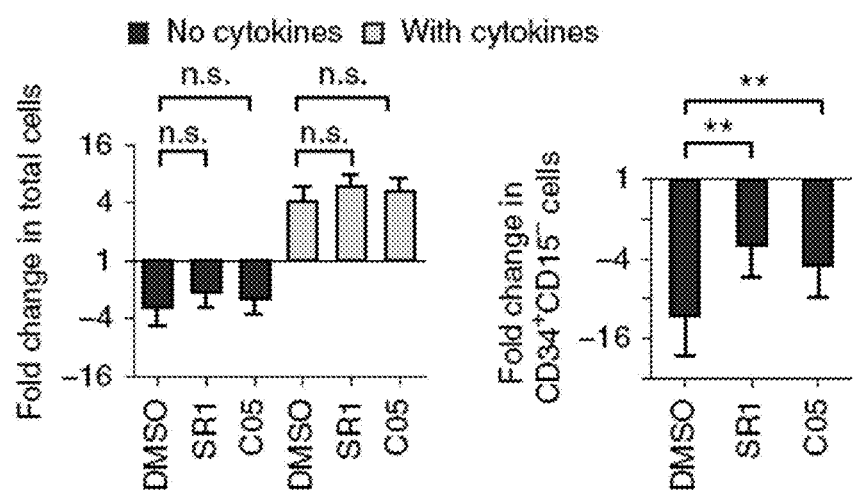
FIG. 3D shows fold changes (geometric mean±SEM, n=9) in total cells (left) and CD34$^+$CD15$^-$ AML cells (right) after 7-day culture in cytokine-supplemented or cytokine-free medium containing SR1 (0.75-1 µM), C05 (2 µM), or DMSO, compared to input numbers ($t_{d7}/t_0$), ** P<0.005, paired t-test.

R: relapse
N.A.: not applicable as not classifiable according to FAB classification To further test this hypothesis, population doublings were tracked using CellTrace™ Violet (Invitrogen®/Life Technologies®) labeled AML cells, in the presence and absence of SR1, and no difference in the distribution of cell generations was observed (FIG. 3C). Furthermore, cytokine withdrawal resulted in a net loss of total and CD34+CD15− cells in all conditions (FIG. 3D), indicating that both tested compounds were not mitogenic. Although total cell counts were similar compared to control also in the absence of cytokines (FIG. 3D), a significantly greater number of CD34+CD15− cells was maintained in cytokine-free conditions in the presence of AhR suppressors compared to controls (FIG. 3D). These results collectively suggest that the onset of differentiation observed following AhR activation might be independent from proliferation.

EXAMPLE 5

AhR Suppressors Support Maintenance of Leukemia Stem Cells

Figure 4A:
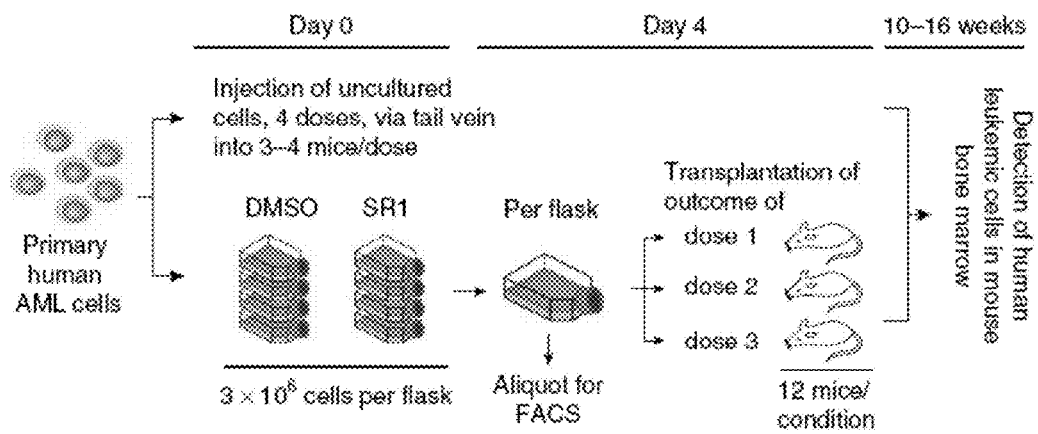
FIG. 4A shows an overview of the in vivo experiments. AML cells from 6 primary human AML samples were injected untreated into the tail vein of sublethally irradiated NSG mice at 4 different doses. On the same day, cell cultures were initiated in T25 culture flasks at a density of 3×10$^6$ cells in 6 ml serum-free medium per flask supplemented with DMSO (0.1%) or SR1 (500 nM). After 4 days in culture the equivalents of freshly injected cell doses were transplanted into NSG mice. Engraftment of human leukemic cells in mouse bone marrow was determined by flow cytometry 10-16 weeks after transplantation.
Figure 4B:
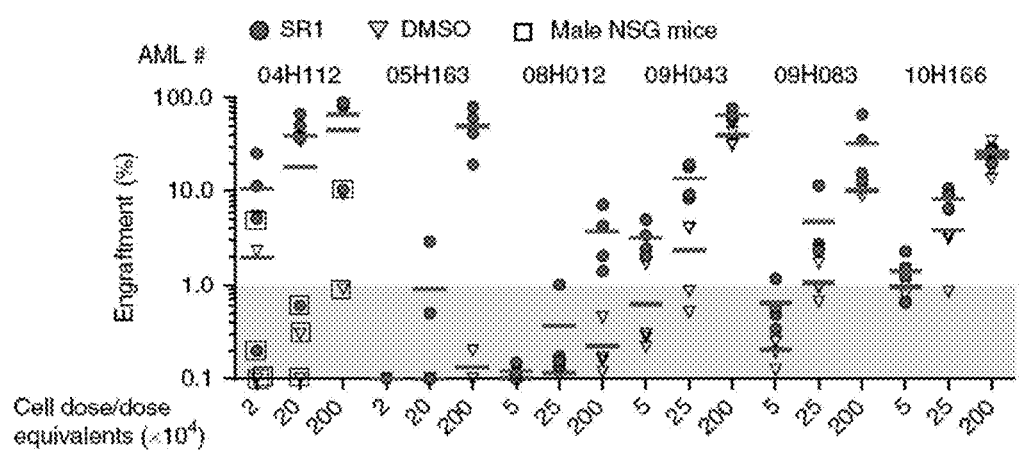
FIG. 4B shows the engraftment levels of AML cells cultured for 4 days in presence of SR1 (0.5-1 µM) or DMSO. Bars indicate means, grey-shaded area indicates <1% human cells in recipient bone marrow, or the absence of engraftment. Mice with <0.1% engraftment were positioned at 0.1%. Indicated transplantation doses represent input cell numbers.
Figure 9:
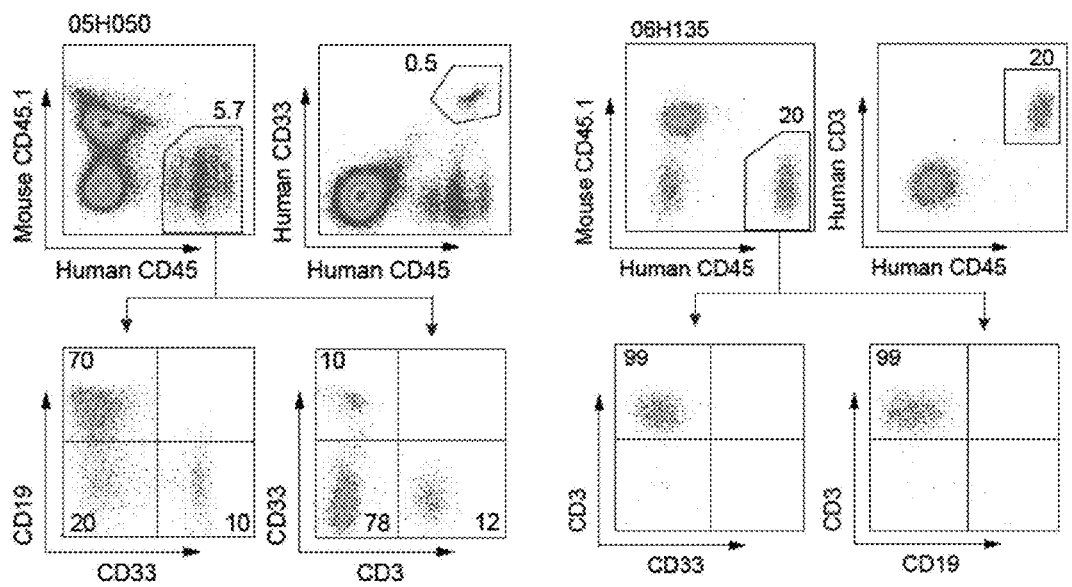
FIG. 9 shows the detection of human myeloid cells ($CD33^+$), B-cells ($CD19^+CD33^-$) and T-cells ($CD3^+CD33^-$) 10 weeks after injection of $2\times10^6$ unsorted patient cells (sample 05H050) (left panel). The right panel shows the detection of human $CD3^+CD45^+$ T-cells in NSG bone marrow after injection of $2\times10^6$ unsorted patient cells (sample 06H135). Numbers in upper panels represent percentages within mouse bone marrow. Percentages in lower panels are fractions of total human $CD45^+$ cells. In both cases the unsorted patient samples contained non-leukemic cells which successfully engrafted NSG mice which has to be distinguished from leukemic engraftment by using a comprehensive antibody cocktail.
Figure 16B:
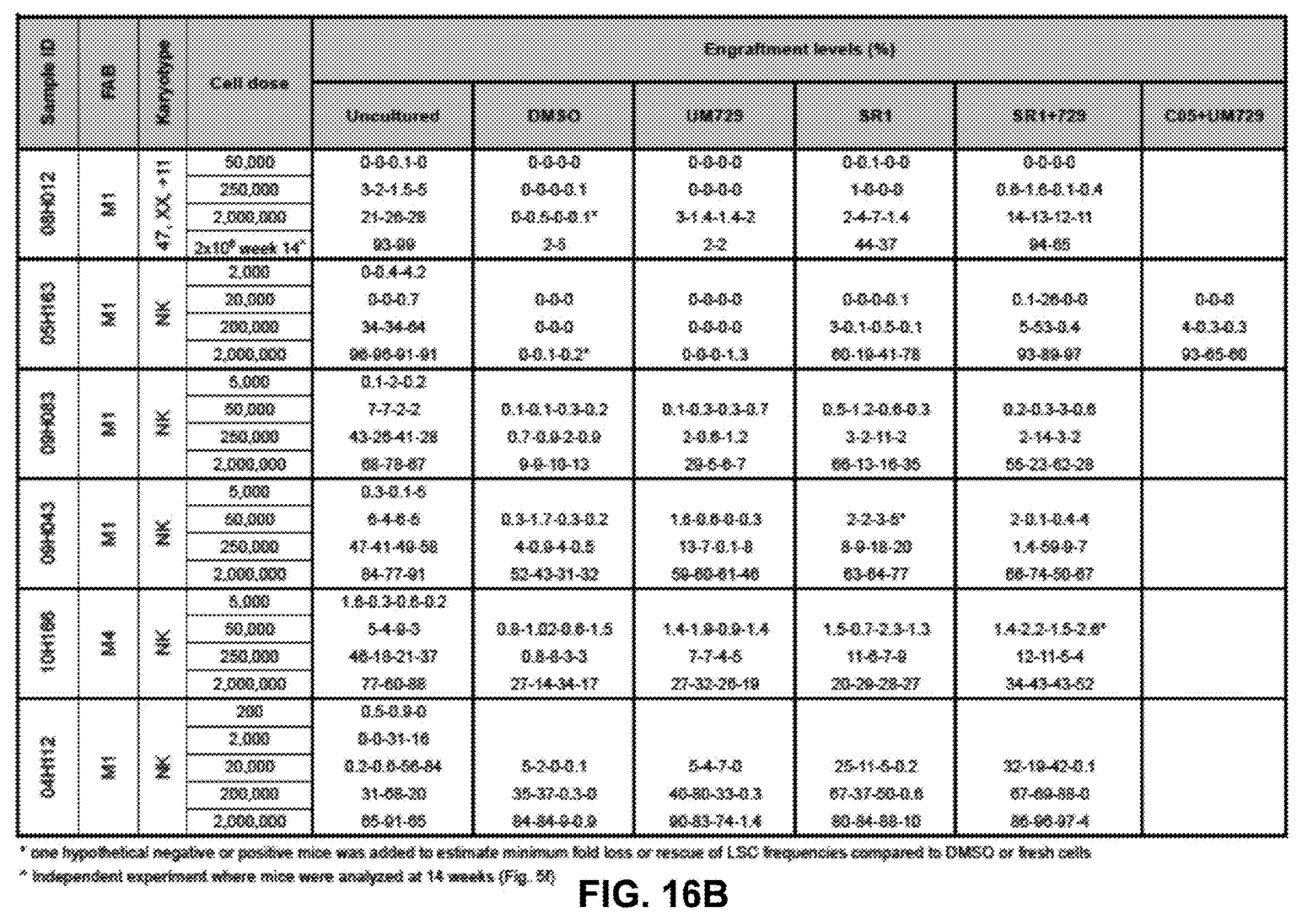

To determine whether functionally engrafting LSCs were supported under the culture conditions, fresh and cultured AML cells were transplanted into immunocompromised NSG mice (FIG. 4A). Unsorted AML specimens were used to avoid bias for certain LSC compartments (e.g., CD34+ versus CD34−). Human leukemic engraftment in mouse bone marrow was analyzed by flow cytometry and anti-human CD3 and CD19 antibodies were included to distinguish human cells of leukemic origin from engraftment of contaminating normal HSCs or lymphocytes potentially contained in unsorted AML samples (FIG. 9). Six samples with proven leukemic engraftment capacity were selected to quantify the impact of SR1 on LSC activity (FIGS. 16A-16C). SR1 was chosen over C05 for in vivo studies, as it had shown better results in vitro. All six samples yielded higher engraftment levels when cultured in the presence of SR1 compared to control DMSO (FIG. 4B). Of note, the numbers of total cells injected into NSG mice on day 4 were similar in the presence and absence of SR1 (total viable cells per flask (median±SD) following 4-day culture 6.2±3×10$^6$ (DMSO) versus 4.8±2×10$^6$ (SR1)) indicating that the control cultures contained living, but more differentiated cells. The impact of SR1 treatment was very strong for sample 05H163, where transplantation of cells recovered from SR1-supplemented cultures, representing the progeny of 2×10$^6$ input cells, yielded on average 50% engraftment, whereas the same dose of DMSO-exposed cells did not reach the threshold for positive engraftment, which was 1% in these studies (FIG. 4C). The CD34+ phenotype (>80% of human CD45+) was maintained independently of the overall engraftment level and irrespective of whether fresh cells, or cells derived from 4-day cultures were transplanted (FIG. 4C). In the absence of SR1 treatment, LSC frequencies were markedly reduced by 10- to 146-fold (average 59-fold) within 4 days in culture (FIG. 4D). LSC frequencies were significantly higher (~10-fold, with a range of 3.7-15.4, Chi-Square test) in SR1-compared to DMSO-supplemented cultures in five of six samples (FIG. 4D). This rescue was partial since LSC numbers in SR1-supplemented cultures remained below that in uncultured cells (FIGS. 4D and 17A-B). Together, these results suggest that AhR activation predominantly impacts the leukemia stem and progenitor cell containing compartment.

EXAMPLE 6

Compound UM729 Collaborates with AhR Suppressors

Figure 5A:
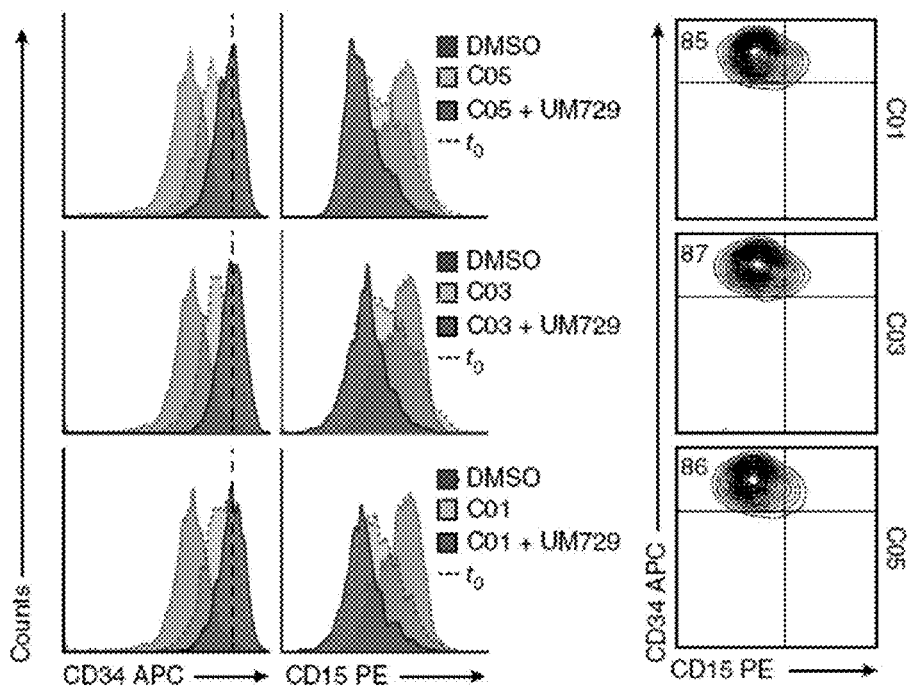
FIG. 5A shows the impact of UM729 on CD34 and CD15 expression of sample 05H163 following 5 days in culture as indicated. Dashed line indicates CD34 peak on day 0.
Figure 5B:
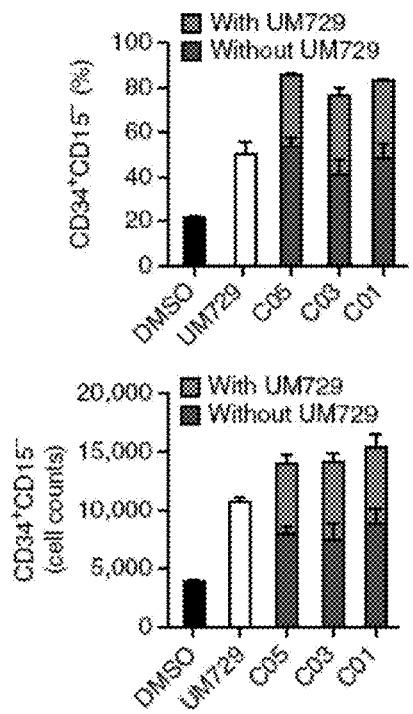
FIG. 5B shows the relative and absolute CD34$^+$CD15$^-$ cell numbers (means±SD, n=3) of AML 05H163 following 5 day culture in the indicated conditions.
Figure 5C:
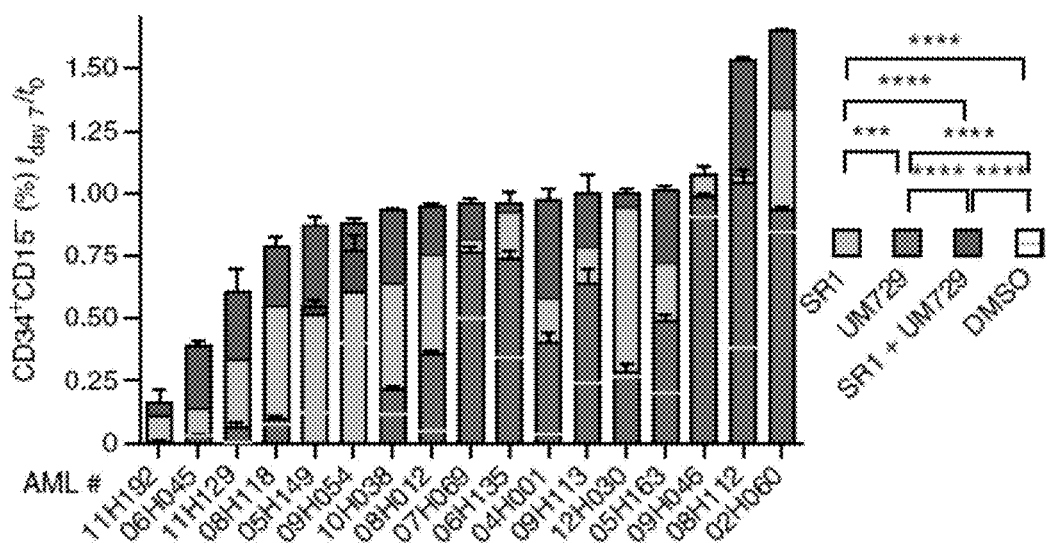
FIG. 5C shows the percentages of CD34$^+$CD15$^-$ cells (mean±SD, 3-8 replicates per sample) normalized to fresh cells ($t_{d7}/t_0$) after 7-day culture with UM729 (1 µM), or vehicle (DMSO). SR1 and DMSO values (means) are shown again for direct comparison (see FIG. 3A for error bars). Wilcoxon matched-pairs test. *P<0.001, **P<0.0001.
Figure 5D:
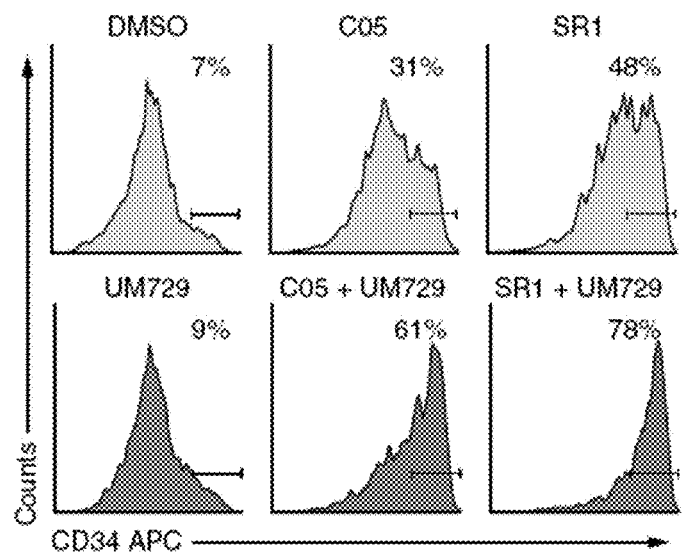
FIG. 5D depicts plots showing the impact of the indicated compounds on CD34 expression of sample 08H118.
Figure 10:
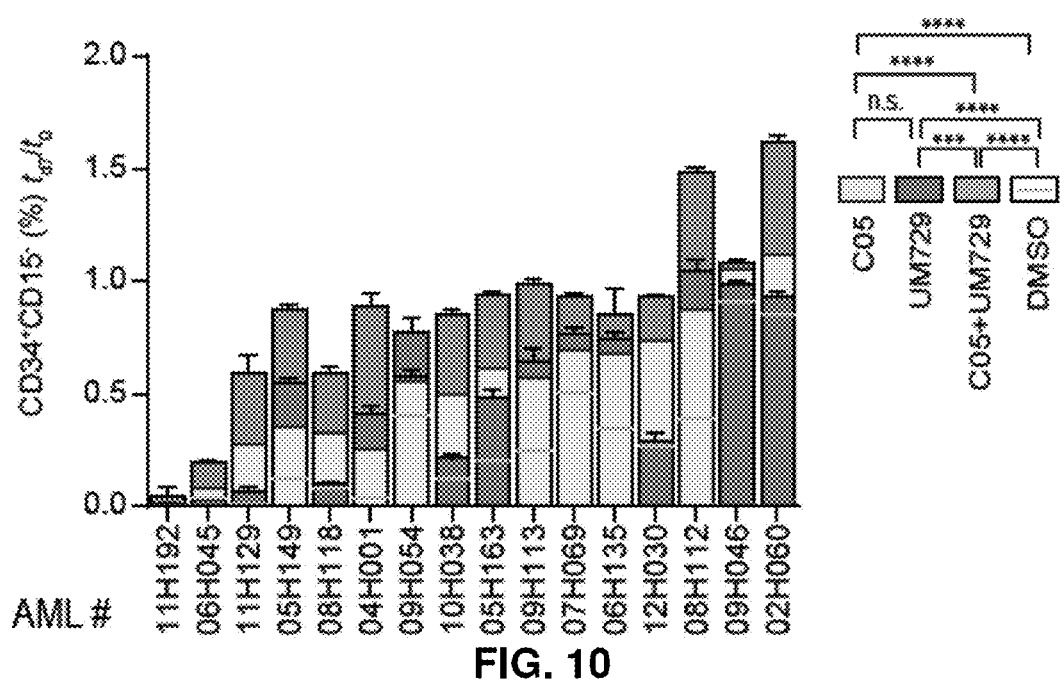
FIG. 10 shows the percentage of $CD34^+CD15^-$ cells (mean±SD) after 7 days in culture with C05 (2 μM), UM729 (1 μM) or both compounds relative to the percentage at $t_0$. Wilcoxon matched pairs signed rank test, *P<0.001, **P<0.0001.
Figure 11:
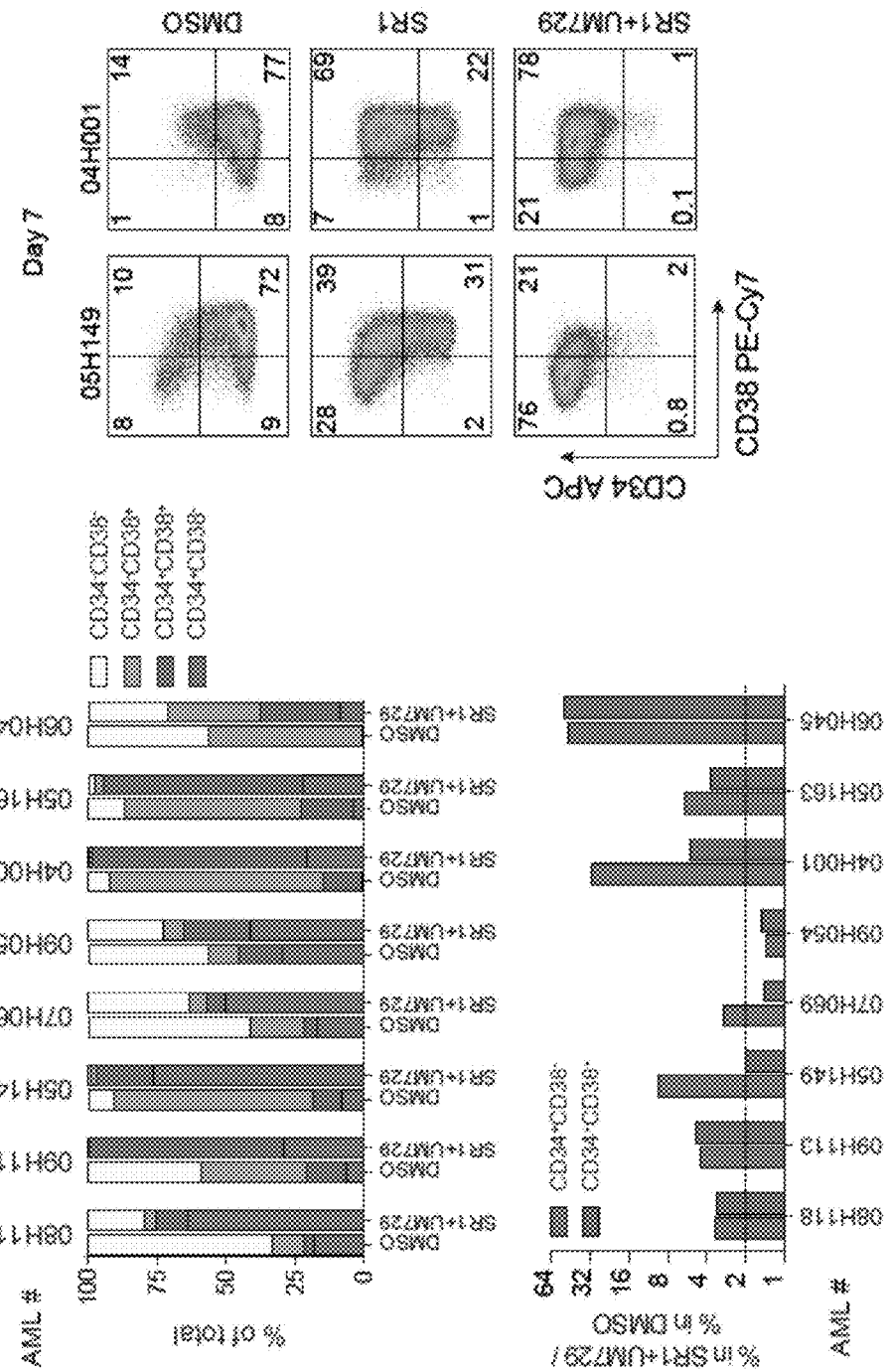
FIG. 11 shows the distribution of $CD34^+CD38^-$, $CD34^+$ $CD38^+$, $CD34^-CD38^+$, and $CD34^-CD38^-$ compartments after 7 days in culture with either DMSO or SR1+UM729 (upper left panel); fold difference in the percentages of $CD34^+CD38^-$ and $CD34^+CD38^+$ cells in presence of SR1+ UM729 compared to DMSO (lower left panel). The right panel is a representative FACS plots of samples 05H149 and 04H001 comparing DMSO, SR1 alone and SR1+UM729. Note the shift towards the more primitive cell compartments.

The Pyrimido indole UM729 was recently identified to expand normal HSPCs in an AhR-independent manner (see WO2013/110198). It was next assessed whether UM729 would have an additive effect with AhR suppressors on the ex vivo culture of primary human AML cells. The addition of UM729 to the screen compounds C01 (Flavonoid), C03 (Benzothiophene), and C05 (β-Carboline) resulted in maintenance of the CD34+CD15− phenotype in ≥85% of cultured 05H163 cells (86% on day 0, see FIG. 1B), a noticeable improvement over maintenance achieved with AhR suppression alone (FIGS. 5A, 5B). Absolute numbers of CD34+CD15− cells were also higher when UM729 was added compared to AhR suppressors alone (FIG. 5B). Next, 17 AML specimens were exposed to UM729 alone and in combination with SR1. Although most samples responded to UM729 (FIG. 5C), SR1 was shown to be superior to UM729, when either compound was added alone, in preventing AML cell differentiation in vitro (FIG. 5C). However, the addition of UM729 to SR1-supplemented cultures enhanced the effect of SR1 in all specimens (FIG. 5C). This was particularly significant in samples that did not respond to UM729 alone (FIG. 5D), indicating that the AhR pathway might be dominant over the pathway targeted by UM729 in these samples. A similar trend was seen when UM729 was combined with C05 (FIGS. 5D and 10). It has been shown that LSCs reside mostly in the CD34$^+$CD38$^-$ compartment, at a lower frequency in the CD34$^+$CD38$^+$ fraction, and occasionally in the CD34$^-$CD38$^+$ and CD34$^-$CD38$^-$ compartments[7]. CD38 expression was thus monitored as an additional surface marker, as it was noticed that not all samples upregulated CD15 in serum-free conditions. It was found that both CD34$^+$ compartments (CD38$^-$ and CD38$^+$) benefitted from the presence of SR1 and UM729 compared to DMSO (FIG. 11), with the impact more consistent on CD34$^+$CD38$^-$ compared to CD34$^+$CD38$^+$ cells.

Figure 5E:
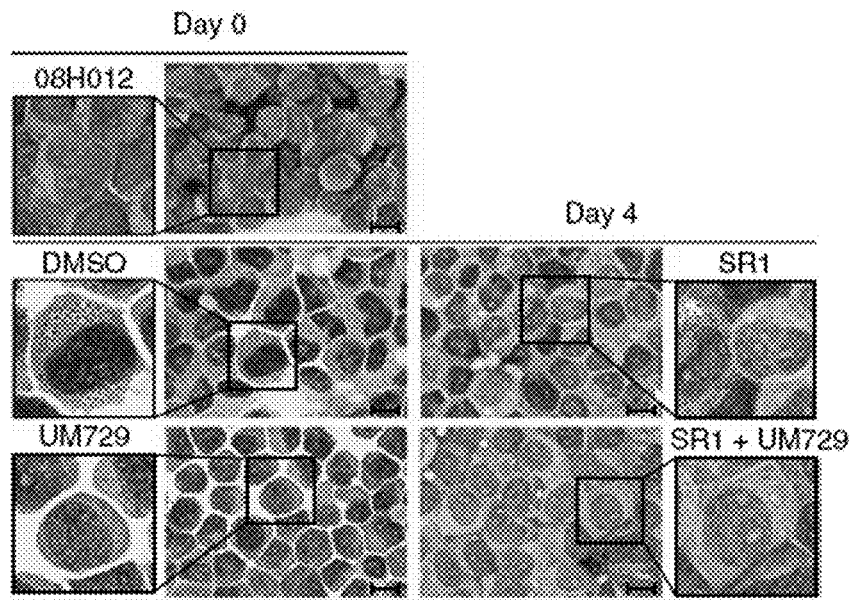
FIG. 5E shows cytospins of fresh AML cells and after 4-day culture as indicated. SR1 is at 500 nM, UM729 at 1 µM. Scale bar indicates 20 µM.
Figure 12:
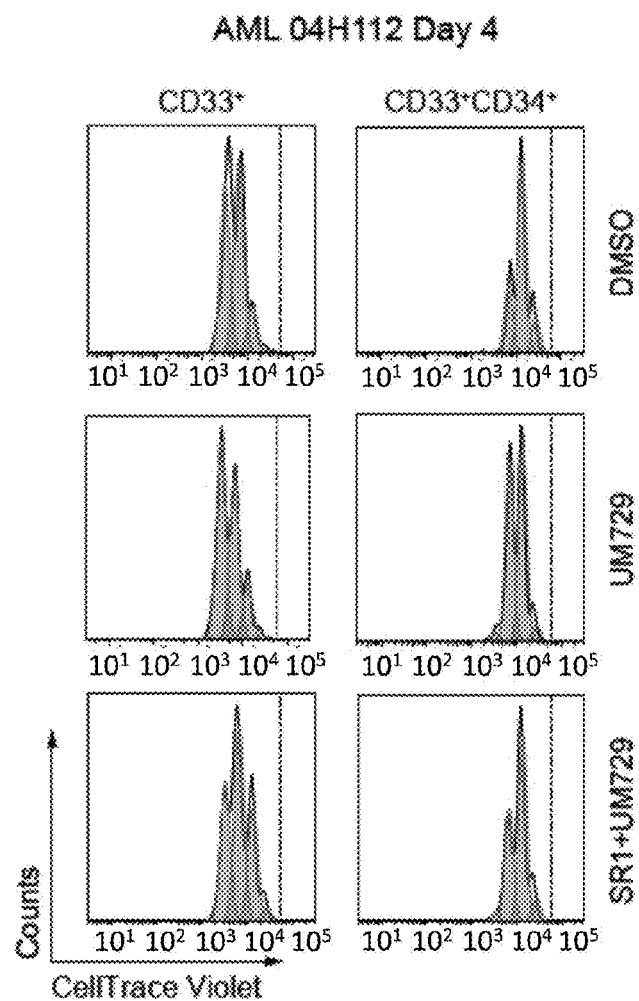
FIG. 12 shows a CellTrace™ Violet profiles of $CD33^+$ and $CD34^+CD33^+$ AML cells (04H112, M1,46,XY) following 4-day culture with UM729 (1 μM) or UM729 (1 μM)+SR1 (0.5 μM), or vehicle DMSO. Dashed line indicates Cell-Trace™ Violet peak for fresh cells (t0), and each individual peak represents one generation of cells.
Figure 13:
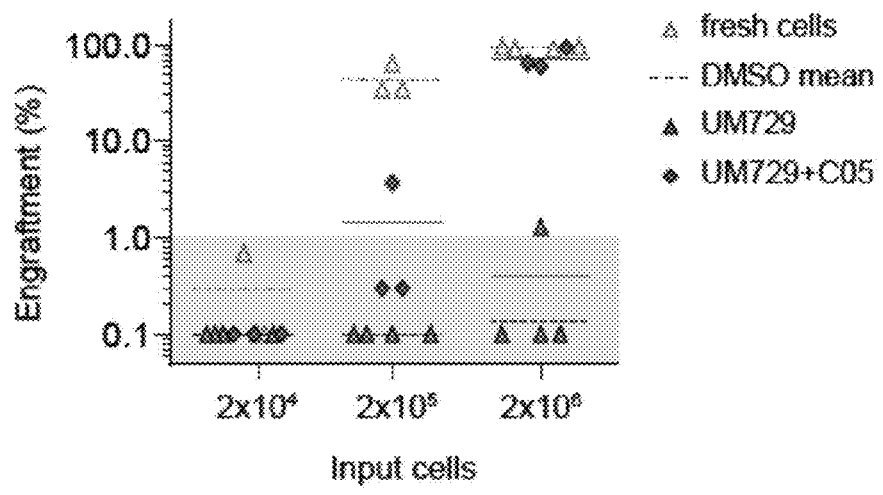
FIG. 13 shows engraftment of AML sample 05H163 16 weeks after injection of $2\times10^4$, $2\times10^5$, or $2\times10^6$ uncultured cells or cultured input cell equivalents. Cultures were supplemented with UM729 (1 μM), UM729 and C05 (2 μM), or DMSO. For DMSO only the mean engraftment level is shown for direct comparison (see FIG. 4B for engraftment levels of individual recipients)

As demonstrated with SR1, UM729 did not affect the number of early cell divisions (FIG. 12). Whereas typical morphologic signs of differentiation (decreased nucleus-cytoplasm-ratio, basophilic granulation) were observed on cytospins from 4-day DMSO and SR1 cultures, these were rarely seen in cells cultured with UM729 alone or in combination with SR1 further demonstrating the additional benefit of UM729 in combination with SR1 (FIG. 5E).

Figure 5F:
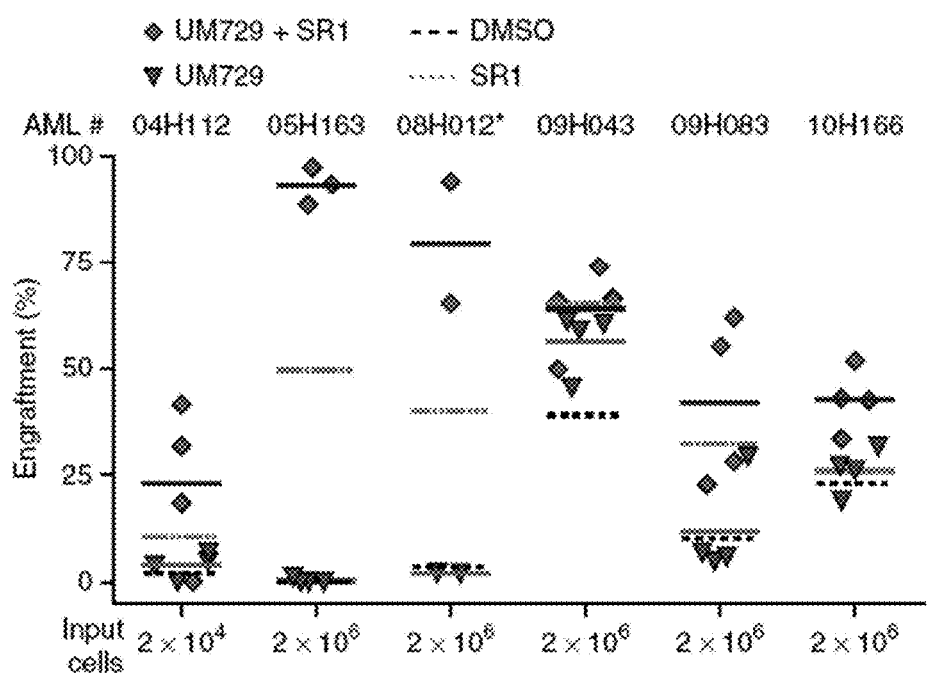
FIG. 5F shows the engraftment levels of AML samples after 4-day cultures in UM729 and UM729+SR1, compared to SR1 alone. DMSO and SR1 values (means) are shown for direct comparison (see FIG. 4B for single recipients). * Mice injected with sample 08H012 were analyzed 14 weeks after transplantation in this experiment.
Figure 5G:
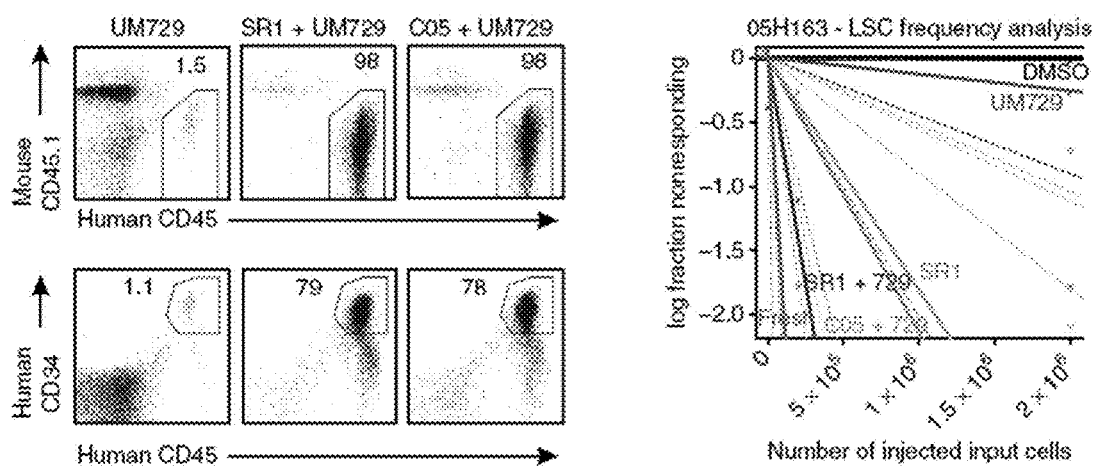
FIG. 5G shows leukemic engraftment (05H163) following injection of 2×10$^6$ input cells exposed for 4 days to the indicated compounds (left panel). LSC frequency analysis of AML 05H163 cultured in different compounds (right panel). One-sided 95% CI shown for DMSO as no engraftment was detected at highest dose.

The impact of UM729 alone and in combination with SR1 on LSC activity was next evaluated by assessing engraftment levels in NSG mice. When administered alone, SR1 was superior to UM729 in supporting LSC functional activity in four of six samples, and was equally efficacious in two samples (FIGS. 5F and 16A-B). Importantly, the addition of UM729 to SR1- (or C05-) supplemented cultures increased engraftment levels, but not LSC frequency, in most samples (FIGS. 5F, 5G, 16A, 16B and 13). Taking into consideration the inter-specimen variation, it may be concluded from the in vitro and in vivo studies that there is an additive effect of UM729 and SR1 on the maintenance of AML stem and progenitor cells in vitro.

Thus, the experiments described herein show improved culture conditions for primary human AML cells, in which serum-free medium supplemented with the small molecules SR1 (an AhR suppressor) and UM729 was used. These conditions yielded improved relative and absolute numbers of phenotypically undifferentiated CD34$^+$ AML progenitors from many specimens and supported the ex vivo maintenance of functionally engrafting human LSCa that are otherwise rapidly lost in culture.

Although the present invention has been described hereinabove by way of specific embodiments thereof, it can be modified, without departing from the spirit and nature of the subject invention as defined in the appended claims. The scope of the claims should not be limited by the preferred embodiments set forth in the examples, but should be given the broadest interpretation consistent with the description as a whole. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Burnett, A., Wetzler, M. & Lowenberg, B. Therapeutic advances in acute myeloid leukemia. Journal of clinical oncology: official journal of the American Society of Clinical Oncology 29, 487-494 (2011).

2. Dick, J. & Lapidot, T. Biology of normal and acute myeloid leukemia stem cells. International journal of hematology 82, 389-396 (2005).

3. Hope, K., Jin, L. & Dick, J. Acute myeloid leukemia originates from a hierarchy of leukemic stem cell classes that differ in self-renewal capacity. Nature immunology 5, 738-743 (2004).

4. Lapidot, T. et al. A cell initiating human acute myeloid leukaemia after transplantation into SCID mice. Nature 367, 645-648 (1994).

5. Pearce, D. et al. AML engraftment in the NOD/SCID assay reflects the outcome of AML: implications for our understanding of the heterogeneity of AML. Blood 107, 1166-1173 (2006).

6. Woiterski, J. et al. Engraftment of low numbers of pediatric acute lymphoid and myeloid leukemias into NOD/SCID/IL2Rγnull mice reflects individual leukemogenecity and highly correlates with clinical outcome. International Journal of Cancer 133, 1547-1556 (2013).

7. Eppert, K. et al. Stem cell gene expression programs influence clinical outcome in human leukemia. Nature medicine 17, 1086-1093 (2011).

8. Gentles, A., Plevritis, S., Majeti, R. & Alizadeh, A. Association of a leukemic stem cell gene expression signature with clinical outcomes in acute myeloid leukemia. JAMA: the journal of the American Medical Association 304, 2706-2715 (2010).

9. Csaszar, E. et al. Rapid expansion of human hematopoietic stem cells by automated control of inhibitory feedback signaling. Cell stem cell 10, 218-229 (2012).

10. Boitano, A. E. et al. Aryl hydrocarbon receptor antagonists promote the expansion of human hematopoietic stem cells. Science 329, 1345-1348 (2010).

11. Mayani, H., Flores-Figueroa, E. & Chavez-Gonzalez, A. In vitro biology of human myeloid leukemia. Leukemia research 33, 624-637 (2009).

12. Barabe, F., Kennedy, J. A., Hope, K. J. & Dick, J. E. Modeling the initiation and progression of human acute leukemia in mice. Science 316, 600-604 (2007).

13. Heuser, M. et al. MN1 overexpression induces acute myeloid leukemia in mice and predicts ATRA resistance in patients with AML. Blood 110, 1639-1647 (2007).

14. Choi, J.-S., Braymer, J., Nanga, R., Ramamoorthy, A. & Lim, M. Design of small molecules that target metal-A{beta} species and regulate metal-induced A{beta} aggregation and neurotoxicity. Proceedings of the National Academy of Sciences of the United States of America 107, 21990-21995 (2010).

15. Borowiak, M. et al. Small molecules efficiently direct endodermal differentiation of mouse and human embryonic stem cells. Cell stem cell 4, 348-358 (2009).

16. Feng, B., Ng, J.-H., Heng, J.-C.D. & Ng, H.-H. Molecules that promote or enhance reprogramming of somatic cells to induced pluripotent stem cells. Cell stem cell 4, 301-312 (2009).

17. Bone, H., Nelson, A., Goldring, C., Tosh, D. & Welham, M. A novel chemically directed route for the generation of definitive endoderm from human embryonic stem cells based on inhibition of GSK-3. Journal of cell science 124, 1992-2000 (2011).

18. Sauvageau, G. Pyrimido[4,5-b]indole derivatives and use thereof in the expansion of hematopoietic stem cells. PCT application No. PCT/CA2013/050052, published under PCT publication No. WO/2013/110198 (2013).

19. Denison, M. & Nagy, S. Activation of the aryl hydrocarbon receptor by structurally diverse exogenous and endogenous chemicals. Annual review of pharmacology and toxicology 43, 309-334 (2003).

20. Henry, E. et al. Flavone antagonists bind competitively with 2,3,7,8-tetrachlorodibenzo-p-dioxin (TCDD) to 21. Bouchez, L. C. et al. Small-molecule regulators of human stem cell self-renewal. Chembiochem: a European journal of chemical biology 12, 854-857 (2011).
22. Knockaert, M. et al. Independent actions on cyclin-dependent kinases and aryl hydrocarbon receptor mediate the antiproliferative effects of indirubins. Oncogene 23, 4400-4412 (2004).
23. Opitz, C. A. et al. An endogenous tumour-promoting ligand of the human aryl hydrocarbon receptor. Nature 478, 197-203 (2011).
24. Swanson, H. DNA binding and protein interactions of the AHR/ARNT heterodimer that facilitate gene activation. Chemico-biological interactions 141, 63-76 (2002).
25. Denison, M., Soshilov, A., He, G., DeGroot, D. & Zhao, B. Exactly the same but different: promiscuity and diversity in the molecular mechanisms of action of the aryl hydrocarbon (dioxin) receptor. Toxicological sciences: an official journal of the Society of Toxicology 124, 1-22 (2011).
26. Krüger, T., Long, M. & Bonefeld-Jørgensen, E. Plastic components affect the activation of the aryl hydrocarbon and the androgen receptor. Toxicology 246, 112-123 (2008).
27. Bhakta, K. et al. Regulation of cytochrome P4501A1 expression by hyperoxia in human lung cell lines: Implications for hyperoxic lung injury. Toxicology and applied pharmacology 233, 169-178 (2008).
28. Magnusson, M. et al. Expansion on stromal cells preserves the undifferentiated state of human hematopoietic stem cells despite compromised reconstitution ability. PLoS One 8, e53912 (2013).
29. Taussig, D. et al. Leukemia-initiating cells from some acute myeloid leukemia patients with mutated nucleophosmin reside in the CD34(−) fraction. Blood 115, 1976-1984 (2010).
30. NTP. Report on Carcinogens, Twelfth Edition. Research Triangle Park, N.C.: U.S. Department of Health and Human Services, Public Health Service, National Toxicology Program. 499 pp. (2011).
31. Prud'homme, G. J. et al. Breast cancer stem-like cells are inhibited by a non-toxic aryl hydrocarbon receptor agonist. PLoS One 5, e13831 (2010).
32. Xiao, Z., Hao, Y., Liu, B. & Qian, L. Indirubin and meisoindigo in the treatment of chronic myelogenous leukemia in China. Leukemia & lymphoma 43, 1763-1768 (2002).

The invention claimed is:

1. An ex vivo cell culture comprising: (a) a cell population comprising acute myeloid leukemia (AML) initiating cells; and (b) a compound of formula II

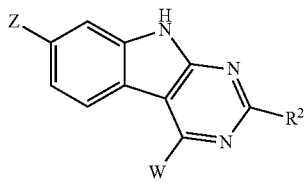

or a salt thereof,
wherein:
Z is
1) —C(O)OR¹,
2) —C(O)NHR¹,
3) —C(O)N(R1)R¹,
4) —CN, or
5) -heterocyclyl optionally substituted with one or more $R^A$ or $R^1$ substituents,
and wherein, when (R¹) and R¹ are attached to a nitrogen atom, optionally they join together with the nitrogen atom to form a 3 to 7-membered ring which optionally includes one or more other heteroatom selected from N, O and S, optionally the ring is substituted with one or more $R^1$ or $R^A$;
W is
1) —OR¹,
2) —NHR¹,
3) —N(R¹)R¹,
4) -L-N(R¹)R¹,
5) -L-heterocyclyl optionally substituted with one or more $R^A$ or $R^1$ substituents attached on either or both the L and the heterocyclyl groups,
6) —O-L-heterocyclyl optionally substituted with one or more $R^A$ or $R^1$ substituents attached on either or both the L and heterocyclyl groups,
7) —N(R¹)-L)ₙ-N(R¹)R¹, wherein n=1, or
8) —(N(R¹)-L)n-heterocyclyl optionally substituted with one or more $R^A$ or $R^1$ substituents, wherein n=1,
and wherein each substituent is optionally attached to the L group if it is not already present,
and wherein when two $R^1$ substituents are present on the same nitrogen atom, then each $R^1$ substituent is independently selected from the list of $R^1$ values described thereafter,
and wherein, when (R¹) and R¹ are attached to a nitrogen atom, optionally they join together with the nitrogen atom to form a 3 to 7-membered ring which optionally includes one or more other heteroatom selected from N, O and S, optionally the ring is substituted with one or more $R^1$ or $R^A$;
L is
1) —C₁₋₆ alkyl,
2) —C₃₋₇ cycloalkyl, or
3) heterocyclyl,
and wherein the alkyl, the cycloalkyl, and the heterocyclyl, groups are each independently optionally substituted with one or two $R^A$ substituent;
$R^1$ is
1) —H,
2) —C₁₋₆ alkyl,
3) —C₂₋₆ alkynyl,
4) —C₁₋₅ perfluorinated alkyl,
5) -heterocyclyl,
6) -aryl, or
7) 5-[(3aS,4S,6aR)-2-oxohexahydro-1H-thieno[3,4-d]imidazol-4-yl]pentanoyl,
and wherein the alkyl, the perfluorinated alkyl, the heterocyclyl, and the aryl, groups are each independently optionally substituted with 1, 2 or 3 $R^A$ or $R^1$ substituents;
$R^2$ is
1) —H,
2) —C₁₋₆ alkyl,
3) —C(O)R¹,
4) -benzyl optionally substituted with 1, 2 or 3 $R^A$ or $R^1$ substituents,
5) -L-heteroaryl optionally substituted with one or more $R^A$ or $R^1$ substituents attached on either one or both the L and the heteroaryl groups, or
6) -L-aryl optionally substituted with one or more $R^A$ or $R^1$ substituents attached on either one or both the L and the aryl groups,
and wherein each substituent is optionally attached to the L group if it is not already present;
$R^A$ is
1) -halogen,
2) —CF₃,
3) —OH,
4) —OR¹,
5) —NH₂,
6) —NHR¹,
7) —NR¹R¹,
8) -L-NH₂,
9) -L-NHR¹,
10) —C(O)R¹,
11) —C(—N=N—)(CF₃).

2. The ex vivo cell culture of claim 1, further comprising a suppressor of the Aryl hydrocarbon Receptor (AhR).

3. The ex vivo cell culture of claim 1, wherein the compound of (b) is a compound of general formula IIA:

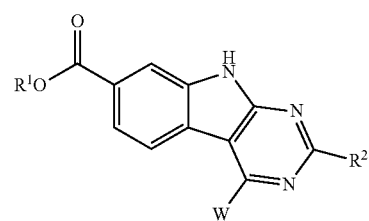

or a salt thereof.

4. The ex vivo cell culture of claim 1, wherein the compound of item (b) is a compound of general formula IIC:

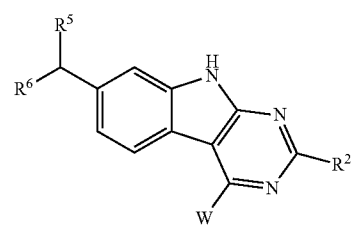

or a salt thereof,
wherein $R^5$ and $R^6$ join together with the carbon atom to which they are attached to form a 5 to 7-membered ring which optionally includes one or more heteroatom selected from N, O and S, optionally the ring is substituted with one or more $R^1$ or $R^4$.

5. The ex vivo cell culture of claim 4, wherein the ring is a 5-membered ring, and the heteroatom is N.

6. The ex vivo cell culture of claim 1, wherein the compound of (b) is a compound of general formula:

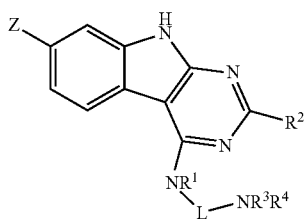

or a salt thereof,
wherein $R^3$ and $R^4$ are the same or different and are each independently H, $R^1$, or $R^3$ and $R^4$ join together with N to which they are attached to form a 3 to 7-membered ring which optionally includes one or more other heteroatom selected from N, O and S, optionally the ring is substituted with one or more $R^1$ or $R^4$.

7. The ex vivo cell culture of claim 1, wherein in said compound of (b), Z is $CO_2Me$ or 2-methyl-2H-tetrazol-5-yl; $R^2$ is benzyl or H, 3-thienylmethyl or 3-pyridinyl methyl; and W is NH-L-N($R^1$)$R^1$ wherein L is $C_{2-4}$ alkyl or $C_{3-7}$ cycloalkyl and $R^1$ and ($R^1$) is C1-4 alkyl or ($R^1$) and $R^1$ join together with the nitrogen atom to which they are attached to form a 3to 7-membered ring, which optionally includes one or more other heteroatom selected from N, O and S, optionally the ring is substituted with one or more $R^1$ or $R^4$.

8. An ex vivo cell culture comprising: (a) a cell population comprising acute myeloid leukemia (AML) initiating cells; and (b) any of compounds 1 to 55 depicted below, or a salt thereof:

| Compound number | Structure |
|---|---|
| 1 | 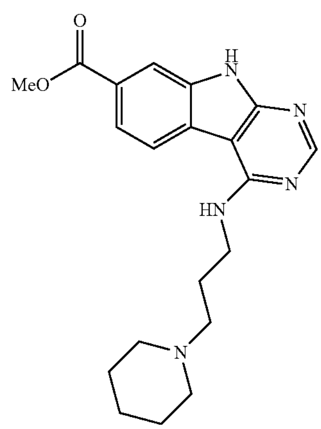 |
| 2 | 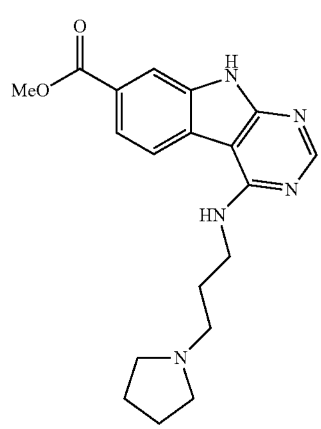 [SMILES: COC(=O)c1ccc2c(c1)[nH]c1ncnc(NCCCN3CCCC3)c12] |

-continued
| Compound number | Structure |
|---|---|
| 3 | 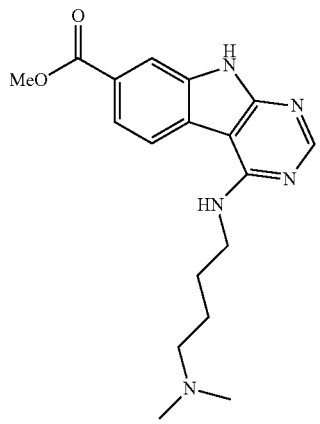 [SMILES: COC(=O)c1ccc2c(c1)[nH]c1ncnc(NCCCCN(C)C)c12] |
| 4 | 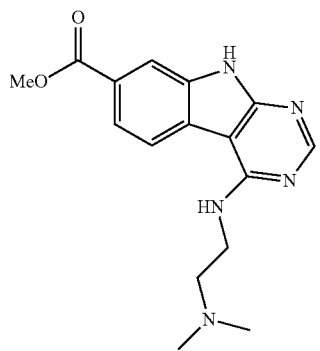 [SMILES: COC(=O)c1ccc2c(c1)[nH]c1ncnc(NCCN(C)C)c12] |
| 5 | 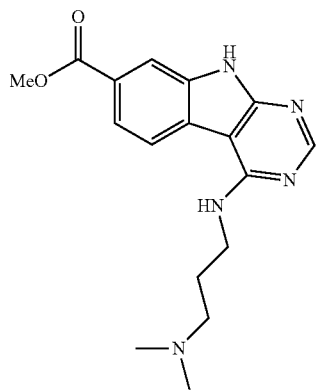 [SMILES: COC(=O)c1ccc2c(c1)[nH]c1ncnc(NCCCN(C)C)c12] |

-continued
| Compound number | Structure |
|---|---|
| 6 | 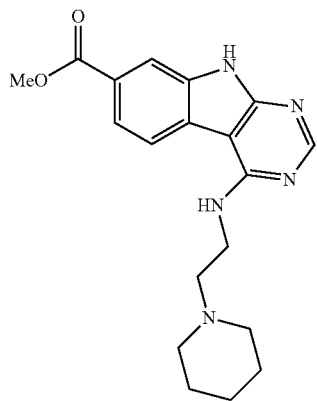 [SMILES: COC(=O)c1ccc2c(c1)[nH]c1ncnc(NCCN3CCCCC3)c12] |
| 7 | 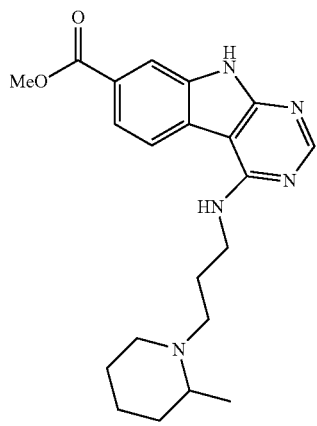 [SMILES: COC(=O)c1ccc2c(c1)[nH]c1ncnc(NCCCN3CCCCC3C)c12] |
| 8 | 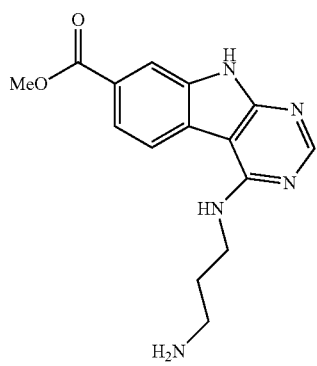 [SMILES: COC(=O)c1ccc2c(c1)[nH]c1ncnc(NCCCN)c12] |

| Compound number | Structure |
|---|---|
| 9 | 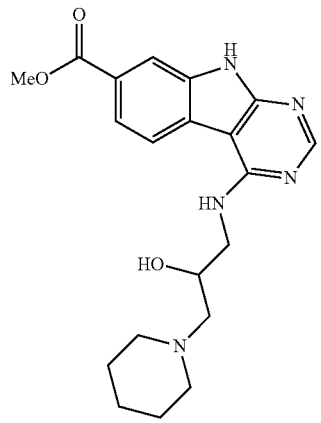 [SMILES: COC(=O)c1ccc2c(c1)[nH]c1ncnc(NCC(O)CN3CCCCC3)c12] |
| 10 | 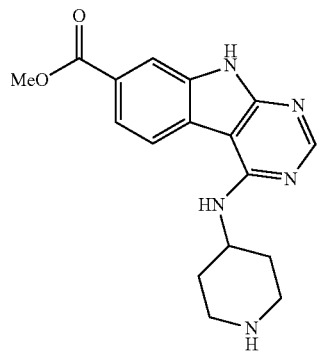 [SMILES: COC(=O)c1ccc2c(c1)[nH]c1ncnc(NC3CCNCC3)c12] |
| 11 | 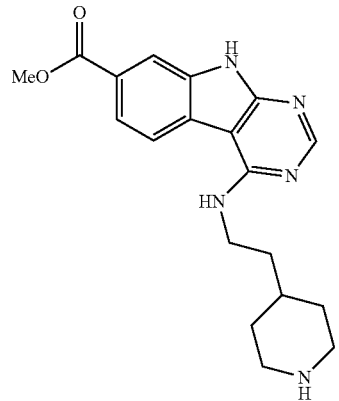 [SMILES: COC(=O)c1ccc2c(c1)[nH]c1ncnc(NCCC3CCNCC3)c12] |

-continued
| Compound number | Structure |
|---|---|
| 12 | 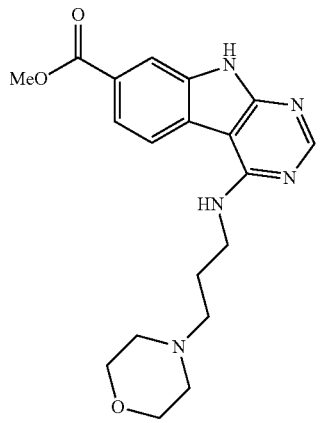 |
| 13 | 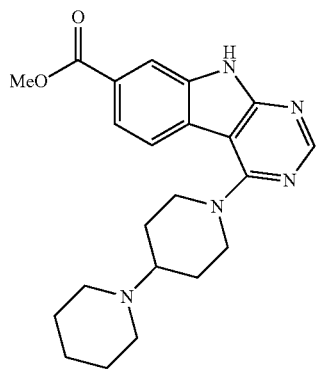 [SMILES: COC(=O)c1ccc2c(c1)[nH]c1ncnc(N3CCC(N4CCCCC4)CC3)c12] |
| 14 | 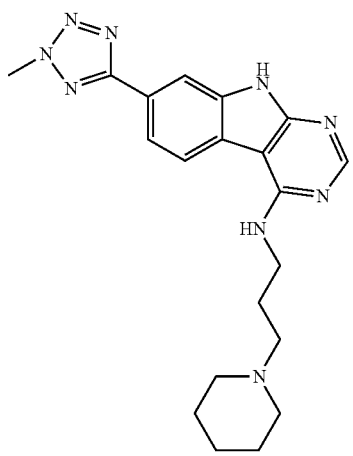 [SMILES: Cn1nnc(-c2ccc3c(c2)[nH]c2ncnc(NCCCN4CCCCC4)c23)n1] |
| 15 | 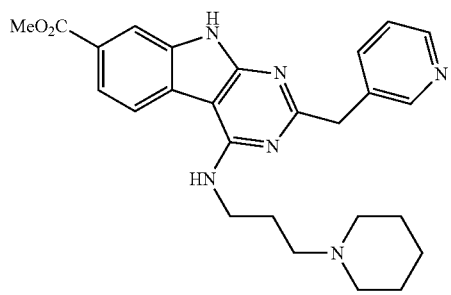 [SMILES: COC(=O)c1ccc2c(c1)[nH]c1nc(Cc3cccnc3)nc(NCCCN3CCCCC3)c12] |

-continued
| Compound number | Structure |
|---|---|
| 16 | 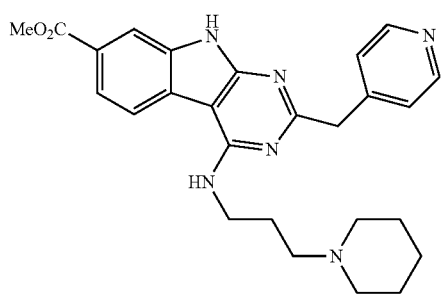 [SMILES: COC(=O)c1ccc2c(c1)[nH]c1nc(Cc3ccncc3)nc(NCCCN3CCCCC3)c12] |
| 17 | 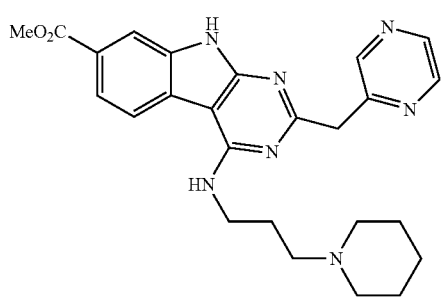 [SMILES: COC(=O)c1ccc2c(c1)[nH]c1nc(Cc3cnccn3)nc(NCCCN3CCCCC3)c12] |
| 18 | 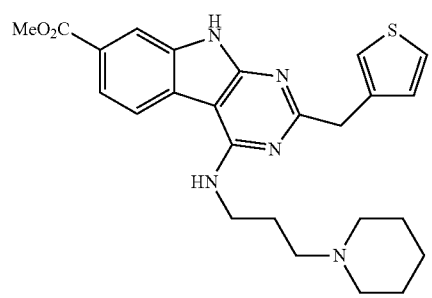 [SMILES: COC(=O)c1ccc2c(c1)[nH]c1nc(Cc3ccsc3)nc(NCCCN3CCCCC3)c12] |
| 19 | 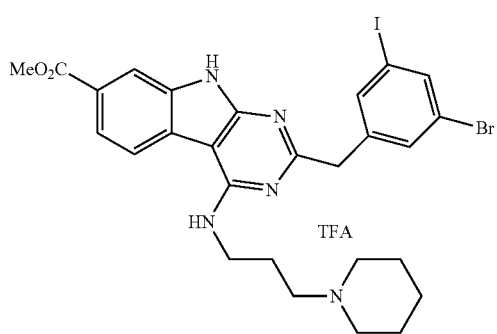 [SMILES: COC(=O)c1ccc2c(c1)[nH]c1nc(Cc3cc(Br)cc(I)c3)nc(NCCCN3CCCCC3)c12] |

-continued
| Compound number | Structure |
|---|---|
| 20 | 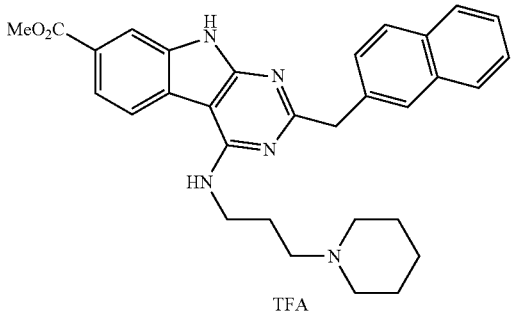 TFA |
| 21 | 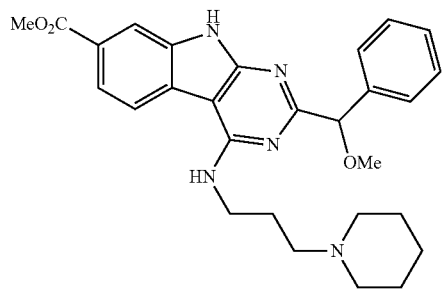 |
| 22 | 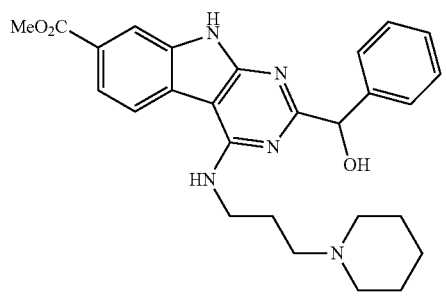 |
| 23 | 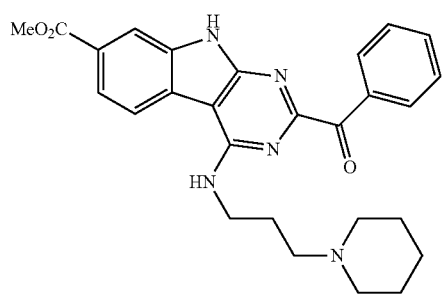 |
| 24 | 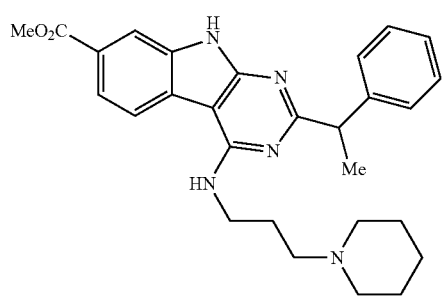 |

| Compound number | Structure |
|---|---|
| 25 | (structure) |
| 26 | (structure) |
| 27 | (structure) |
| 28 | (structure) |
| 29 | (structure) |

-continued
| Compound number | Structure |
|---|---|
| 30 | 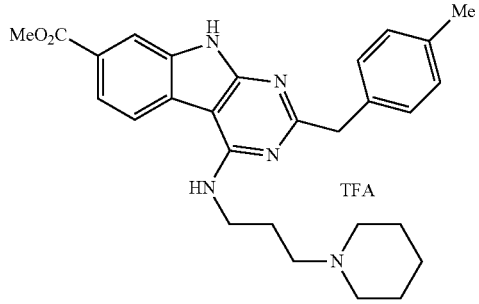 TFA |
| 31 | 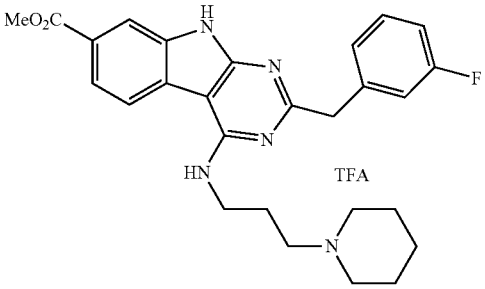 TFA |
| 32 | 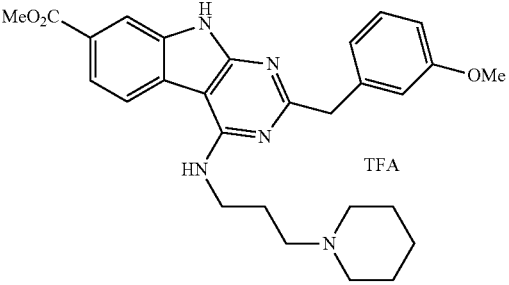 TFA |
| 33 | 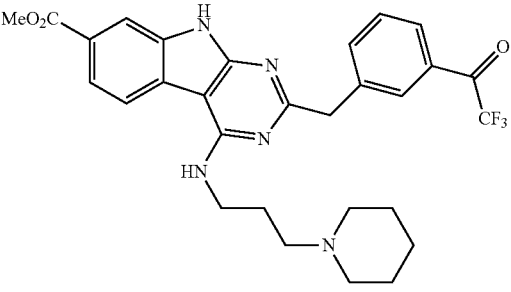 |
| 34 | 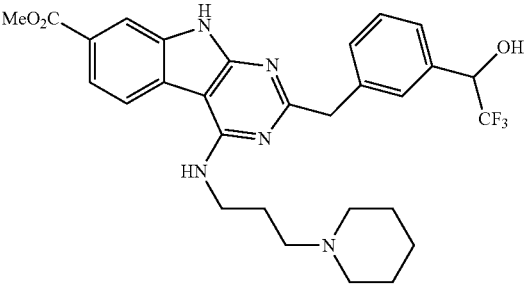 |

-continued
| Compound number | Structure |
|---|---|
| 35 | 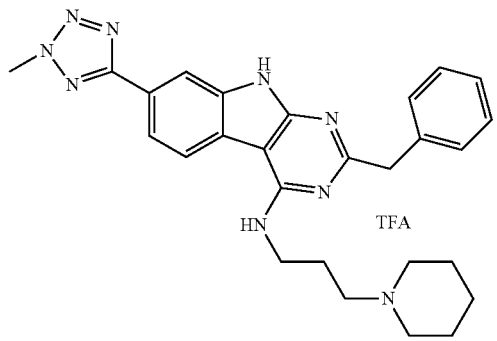 TFA |
| 36 | 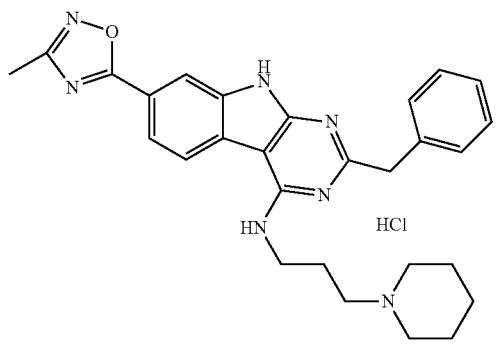 HCl |
| 37 | 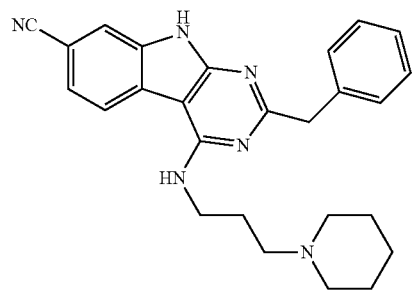 |
| 38 | 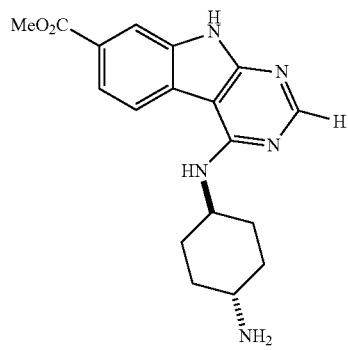 |

-continued
| Compound number | Structure |
|---|---|
| 39 | 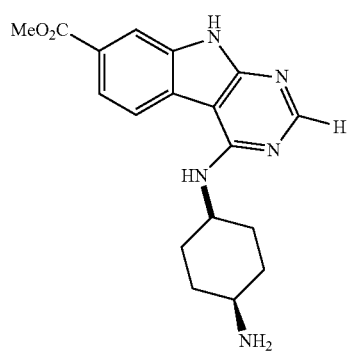 |
| 40 | 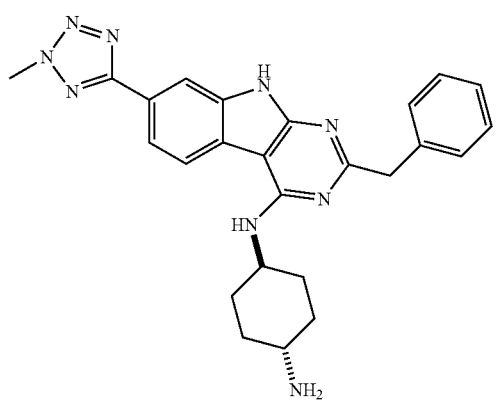 |
| 41 | 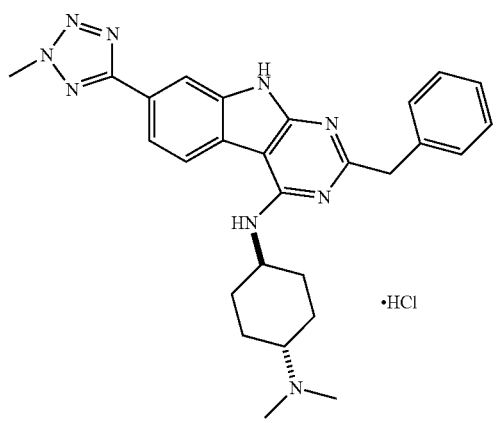 |
| 42 | 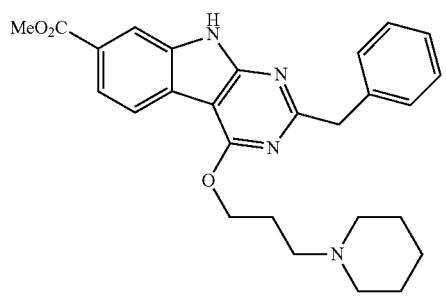 [SMILES: COC(=O)c1ccc2c(c1)[nH]c1nc(Cc3ccccc3)nc(OCCCN3CCCCC3)c12] |

-continued
| Compound number | Structure |
|---|---|
| 43 | 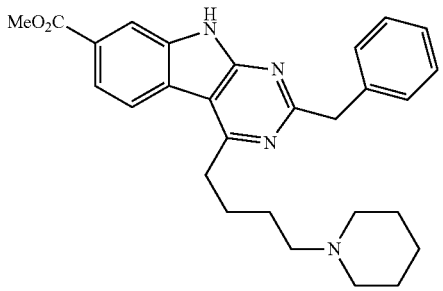 [SMILES: COC(=O)c1ccc2c(c1)[nH]c1nc(Cc3ccccc3)nc(CCCCN3CCCCC3)c12] |
| 44 | 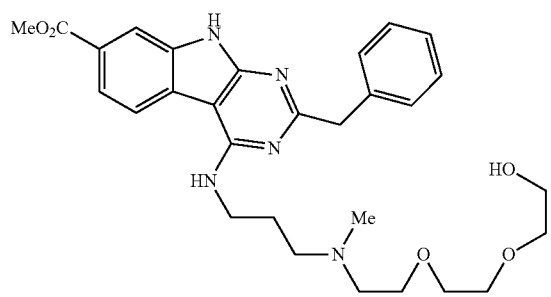 [SMILES: COC(=O)c1ccc2c(c1)[nH]c1nc(Cc3ccccc3)nc(NCCCN(C)CCOCCOCCO)c12] |
| 45 | 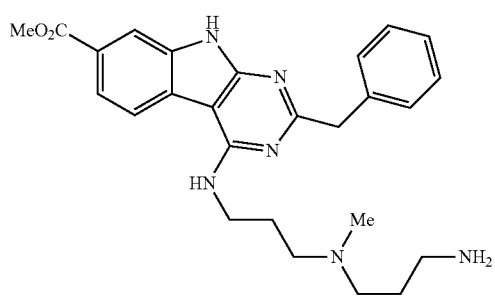 [SMILES: COC(=O)c1ccc2c(c1)[nH]c1nc(Cc3ccccc3)nc(NCCCN(C)CCCN)c12] |
| 46 | 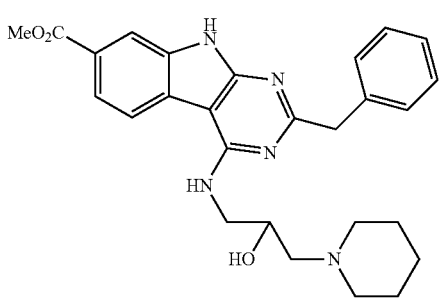 [SMILES: COC(=O)c1ccc2c(c1)[nH]c1nc(Cc3ccccc3)nc(NCC(O)CN3CCCCC3)c12] |
| 47 | 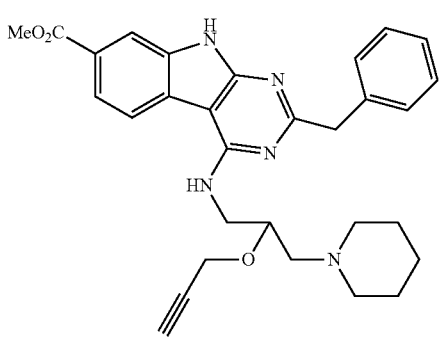 [SMILES: C#CCOC(CNc1nc(Cc2ccccc2)nc2[nH]c3cc(C(=O)OC)ccc3c12)CN1CCCCC1] |

-continued
| Compound number | Structure |
|---|---|
| 48 | 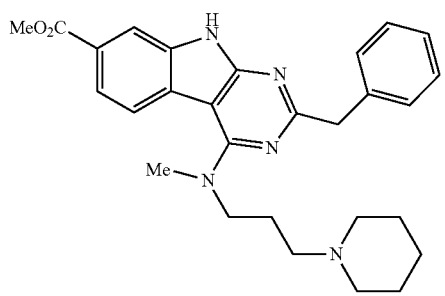 [SMILES: COC(=O)c1ccc2c(c1)[nH]c1nc(Cc3ccccc3)nc(N(C)CCCN3CCCCC3)c12] |
| 49 | 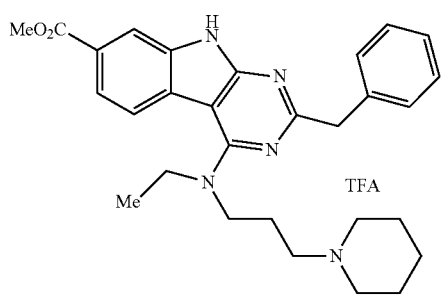 [SMILES: CCN(CCCN1CCCCC1)c1nc(Cc2ccccc2)nc2[nH]c3cc(C(=O)OC)ccc3c12] |
| 50 | 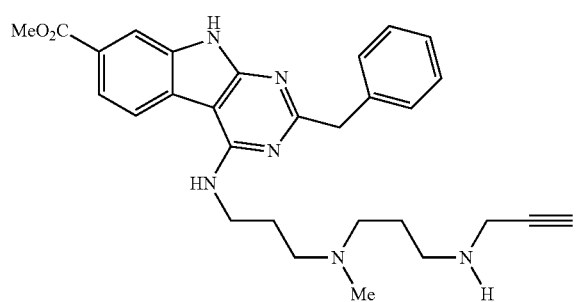 [SMILES: C#CCNCCCN(C)CCCNc1nc(Cc2ccccc2)nc2[nH]c3cc(C(=O)OC)ccc3c12] |
| 51 | 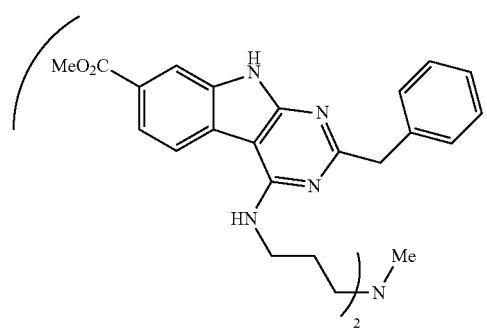 |

-continued
| Compound number | Structure |
|---|---|
| 52 | 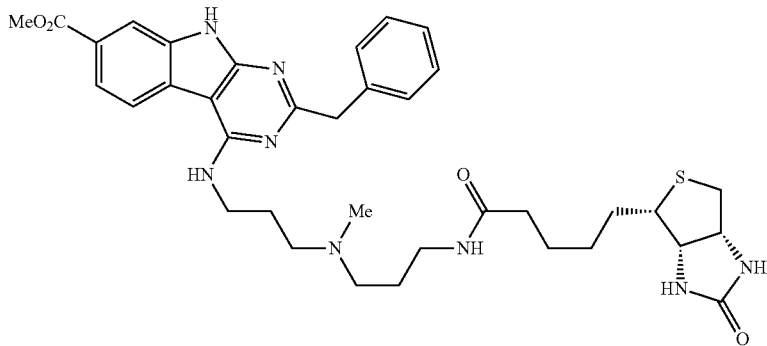 [SMILES: COC(=O)c1ccc2c(c1)[nH]c1nc(Cc3ccccc3)nc(NCCCN(C)CCCNC(=O)CCCC[C@@H]3SC[C@@H]4NC(=O)N[C@@H]43)c12] |
| 53 | 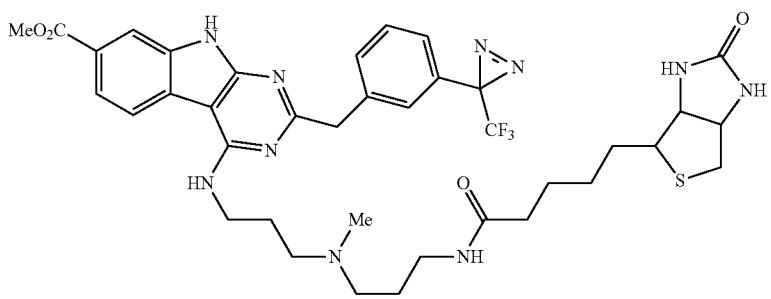 [SMILES: COC(=O)c1ccc2c(c1)[nH]c1nc(Cc3cccc(C4(C(F)(F)F)N=N4)c3)nc(NCCCN(C)CCCNC(=O)CCCCC3SCC4NC(=O)NC43)c12] |
| 54 | 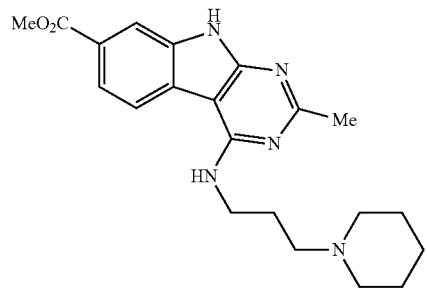 [SMILES: COC(=O)c1ccc2c(c1)[nH]c1nc(C)nc(NCCCN3CCCCC3)c12] |
| 55 | 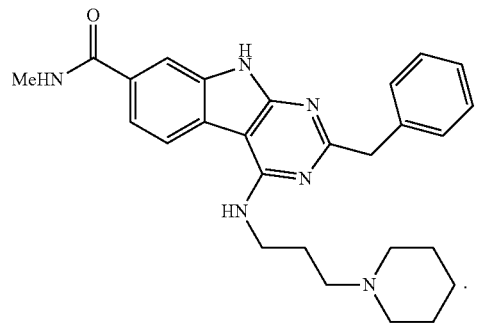 [SMILES: CNC(=O)c1ccc2c(c1)[nH]c1nc(Cc3ccccc3)nc(NCCCN3CCCCC3)c12] |

9. The ex vivo cell culture of claim 1, wherein the compound of (b) is compound 1:
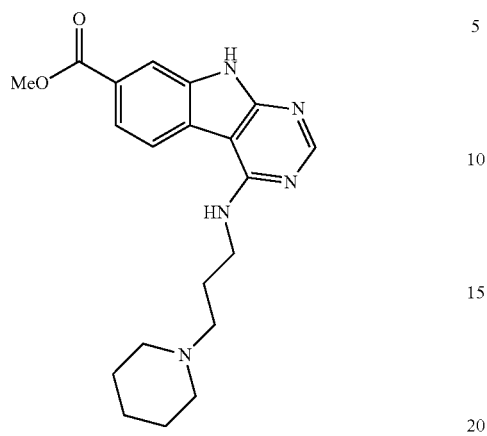
or a salt thereof.
10. The ex vivo cell culture of claim 2, wherein said suppressor of AhR is StemRegenin 1 (SR1), retusin-7-methylether, UM0125464, chrysin, kaempferide, xanthone, 3-chloro-N-(2,3-dihydro-1,4-benzodioxin-6-yl)-1-benzithiophene-2-carboxamide, 5-methoxyflavone, or N-methyl-β-carboline-3-carboxamide.
* * * * *